United States Patent
Ariaans et al.

(10) Patent No.: US 9,573,996 B2
(45) Date of Patent: Feb. 21, 2017

(54) MONOCLONAL ANTIBODIES TO HUMAN PROINFLAMMATORY CYTOKINES AND METHODS FOR TREATING INFLAMMATORY DISEASES

(71) Applicant: Synthon Biopharmaceuticals B.V., Nijmegen (NL)

(72) Inventors: Gerardus Joseph Andreas Ariaans, Nijmegen (NL); Frans van Dalen, Nijmegen (NL); Declan Thomas Nolan, Nijmegen (NL)

(73) Assignee: Synthon Biopharmaceuticals B.V., Nijmegen (NL)

( * ) Notice: Subject to any disclaimer, the term of this patent is extended or adjusted under 35 U.S.C. 154(b) by 0 days.

(21) Appl. No.: 14/365,940

(22) PCT Filed: Dec. 14, 2012

(86) PCT No.: PCT/EP2012/075670
§ 371 (c)(1),
(2) Date: Jun. 16, 2014

(87) PCT Pub. No.: WO2013/087911
PCT Pub. Date: Jun. 20, 2013

(65) Prior Publication Data
US 2015/0166649 A1  Jun. 18, 2015

Related U.S. Application Data

(60) Provisional application No. 61/576,727, filed on Dec. 16, 2011, provisional application No. 61/576,922, filed on Dec. 16, 2011.

(51) Int. Cl.
| | | |
|---|---|---|
| *C07K 16/24* | (2006.01) | |
| *C12N 15/82* | (2006.01) | |
| *A61K 9/00* | (2006.01) | |
| *A61K 39/00* | (2006.01) | |

(52) U.S. Cl.
CPC .......... *C07K 16/241* (2013.01); *A61K 9/0053* (2013.01); *C07K 16/244* (2013.01); *C12N 15/8258* (2013.01); *A61K 39/00* (2013.01); *A61K 2039/505* (2013.01); *A61K 2039/54* (2013.01); *C07K 2317/13* (2013.01); *C07K 2317/24* (2013.01); *C07K 2317/41* (2013.01); *C07K 2317/565* (2013.01); *C07K 2317/76* (2013.01)

(58) Field of Classification Search
CPC .......... A61K 9/0053; A61K 39/00; A61K 2309/505; A61K 2309/54; C07K 16/241; C07K 2317/13; C07K 2317/24; C07K 2317/41; C07K 2317/76; C07K 2317/565
See application file for complete search history.

(56) References Cited

U.S. PATENT DOCUMENTS

| | | |
|---|---|---|
| 4,771,002 A | 9/1988 | Gelvin |
| 5,075,236 A | 12/1991 | Yone et al. |
| 5,428,147 A | 6/1995 | Barker et al. |
| 5,605,690 A | 2/1997 | Jacobs et al. |
| 5,656,272 A | 8/1997 | Le et al. |
| 5,919,452 A | 7/1999 | Le et al. |
| 6,040,498 A | 3/2000 | Stomp et al. |
| 6,090,382 A | 7/2000 | Salfeld et al. |
| 6,451,982 B1 | 9/2002 | Chou et al. |
| 6,790,444 B2 | 9/2004 | Le et al. |
| 6,902,724 B1 | 6/2005 | Parekh et al. |
| 6,902,734 B2 | 6/2005 | Giles-Komar et al. |
| 6,914,128 B1 | 7/2005 | Salfeld et al. |
| 7,012,135 B2 | 3/2006 | Athwal et al. |
| 7,147,854 B2 | 12/2006 | Ye |
| 7,161,064 B2 | 1/2007 | Stomp et al. |
| 7,176,024 B2 | 2/2007 | Branson et al. |
| 7,186,820 B2 | 3/2007 | Athwal et al. |
| 7,622,573 B2 | 11/2009 | Dickey et al. |
| 7,632,983 B2 | 12/2009 | Dickey et al. |
| 7,883,704 B2 | 2/2011 | Salfeld et al. |
| 7,884,264 B2 | 2/2011 | Dickey et al. |
| 8,034,916 B2 | 10/2011 | Dickey et al. |
| 2009/0060921 A1 | 3/2009 | Dickey et al. |
| 2009/0214528 A1 | 8/2009 | Dorai et al. |
| 2010/0209966 A1 | 8/2010 | Everett et al. |
| 2012/0190004 A1 | 7/2012 | Parsons et al. |
| 2014/0356357 A1 | 12/2014 | Ariaans et al. |
| 2014/0359902 A1 | 12/2014 | Ariaans et al. |
| 2015/0010544 A1 | 1/2015 | Ariaans et al. |

FOREIGN PATENT DOCUMENTS

| | | |
|---|---|---|
| EP | 0449769 B1 | 12/1993 |
| EP | 0932415 A1 | 8/1999 |
| EP | 0602126 B1 | 3/2003 |

(Continued)

OTHER PUBLICATIONS

Chan AC, et al. Nature Reviews Immunology. 10(5):301-316, May 5, 2010.*
Worledge KL, et al. Digestive Diseases and Sciences. 45(12):2298-2305, Dec. 1, 2000.*
Berdoz J, et al. Proc. Natl. Acad. Sci. 96(6):3029-3034, Mar. 16, 1999.*
Ma J K-C et al. Science. 268:716-719, May 5, 1995.*
Paul, WE. Fundamental Immunology, 3rd ed. Raven Press, NY, Chap. 9, pp. 292-295, 1993.*
Rudikoff S. et al. Proc. Natl. Acad. Sci. USA, 79:1979-1983, 1982.*
Colman, PM. Research in Immunology, Elsevier, NY, 145(1):33-36, 1994.*

(Continued)

*Primary Examiner* — Robert Landsman
(74) *Attorney, Agent, or Firm* — Sterne Kessler Goldstein & Fox

(57) ABSTRACT

A monoclonal secretory IgA antibody, which binds to and neutralizes a human proinflammatory cytokine or which binds to and blocks a human proinflammatory cytokine receptor. The secretory IgA antibody is useful in treating a variety of inflammatory diseases in humans.

24 Claims, 29 Drawing Sheets

(56) References Cited

FOREIGN PATENT DOCUMENTS

| | | | |
|---|---|---|---|
| EP | 1309692 B1 | 5/2009 | |
| EP | 1313769 B2 | 11/2011 | |
| EP | 0783893 B1 | 4/2012 | |
| EP | 1776142 B3 | 6/2015 | |
| WO | WO-8907452 A1 | 8/1989 | |
| WO | WO-9216553 A1 | 10/1992 | |
| WO | WO-9222653 A1 | 12/1992 | |
| WO | WO-9729131 A1 | 8/1997 | |
| WO | WO-9949024 A2 | 9/1999 | |
| WO | WO-2005007699 A2 | 1/2005 | |
| WO | WO-2005035768 A1 | 4/2005 | |
| WO | WO-2007028106 A2 | 3/2007 | |
| WO | WO-2007084672 A2 | 7/2007 | |
| WO | WO-2007084922 A2 | 7/2007 | |
| WO | WO-2007084926 A2 | 7/2007 | |
| WO | WO-2007124186 A2 | 11/2007 | |
| WO | WO-2009086003 A1 | 7/2009 | |
| WO | WO-2011/047238 A1 | 4/2011 | |
| WO | WO 2011/047328 | * | 4/2011 |
| WO | WO-2012162367 A1 | 11/2012 | |
| WO | WO-2013087912 A1 | 6/2013 | |
| WO | WO-2013087913 A1 | 6/2013 | |
| WO | WO-2013087914 A1 | 6/2013 | |

OTHER PUBLICATIONS

Akdis, C.A., "Therapies for Allergic Inflammation: Refining Strategies to Induce Tolerance," Nature Medicine 18(5):736-749, Nature Publishing Company, United States (2012).

Bakker, H., et al, "An Antibody Produced in Tobacco Expressing Hybrid β-1,4-galactosyltransferase is Essentially Devoid of Plant Carbohydrate Epitopes," Proceedings of the National Academy of Sciences USA 103(20):7577-7582, National Academy of Sciences, United States (2006).

Berdoz, J., et al., "In Vitro Comparison of the Antigen-binding and Stability Properties of the Various Molecular Forms of IgA Antibodies Assembled and Produced in CHO Cells," Proceedings of the National Academy of Sciences USA 96(6):3029-3034, National Academy of Sciences, United States (1999).

Berdoz, J. and Corthesy, B., "Human Polymeric IgA is Superior to IgG and Single-chain Fv of the Same Monoclonal Specificity to Inhibit Urease Activity Associated with *Helicobacter Pylori*," Molecular Immunology 41(10):1013-1022, Elsevier, Netherlands (2004).

Beyer, T., et al., "Serum-free Production and Purification of Chimeric IgA Antibodies," Journal of Immunological Methods 346(1-2):26-37, Elsevier, Netherlands (2009).

Brooks, D., et al., "Phase Ia Trial of Murine Immunoglobulin A Antitransferrin Receptor Antibody 42/6," Clinical Cancer Research 1(11):1259-1265, American Association for Cancer Research, United States (1995).

Brown, M., et al., "Tolerance to Single, but Not Multiple, Amino Acid Replacements in AntibodyV$_H$ CDR2: A Means of Minimizing B Cell Wastage from Somatic Hyperinutation?," Journal of Immunology 156(9):3285-3291, American Association of Immunologists, United States (1996).

Carter, P, et al., "Humanization of an Anti-p185$^{HER2}$ Antibody for Human Cancer Therapy," Proceedings of the National Academy of Sciences USA 89(10):4285-4289, National Academy of Sciences, United States (1992).

Chan, A.C. and Carter, P.J., "Therapeutic Antibodies for Autoimmunity and Inflammation," Nature Reviews Immunology 10(5):301-316, Macmillan Publishers Limited, England (2010).

Chintalacharuvu, K.R. and Morrison, S.L., "Production of Secretory Immunoglobulin A by a Single Mammalian Cell," Proceedings of the National Academy of Sciences USA 94(12):6364-6368, National Academy of Sciences, United States (1997).

Chintalacharuvu, K.R., et al., "Divergence of Human α-chain Constant Region Gene Sequences: A Novel Recombinant α2 Gene," Journal of Immunology 152(11):5299-5304, American Association of Immunologists, United States (1994).

Corthesy, B., "Recombinant Immunoglobulin A: Powerful Tools for Fundamental and Applied Research," Trends in Biotechnology 20(2):65-71, Elsevier Science Publishers, England (2002).

Cox, K.M., et al., "Glycan Optimization of a Human Monoclonal Antibody in the Aquatic Plant Lemna Minor," Nature Biotechnology 24(12):1591-1597, Nature America Publishing, United States (2006).

Dechant, M. and Valerius, T., "IgA Antibodies for Cancer Therapy," Critical Reviews in Oncology/Hematology 39(1-2):69-77, Elsevier Science Ireland, Ireland (2001).

Dechant, M., et al., "Chimeric IgA Antibodies Against Hla Class II Effectively Trigger Lymphoma Cell Killing," Blood 100(13):4574-4580, American Society of Hematology, United States (2002).

Dechant, M., et al., "Effector Mechanisms of Recombinant IgA Antibodies Against Epidermal Growth Factor Receptor," Journal of Immunology 179(5):2936-2943, American Association of Immunologists, United States (2007).

Durocher, Y., et al., "High-level and High-throughput Recombinant Protein Production by Transient Transfection of Suspension-growing Human 293-EBNA1 Cells," Nucleic Acids Research 30(2):E9, Oxford University Press, England (2002).

Favre, L.I., et al., "Simplified Procedure to Recover Recombinant Antigenized Secretory IgA to be Used as a Vaccine Vector," Journal of Chromatography. B 786(1-2):143-151, Elsevier, Netherlands (2003).

Fernandes, D., "Demonstrating Comparability of Antibody Glycosylation During Biomanufacturing," European Pharmaceutical Review 106-110, Samedan Ltd., Germany (2005).

Garber, K., "Anti-IL-17 mAbs Herald New Options in Psoriasis," Nature Biotechnology 30(6):475-477, Nature America Publishing, United States (2012).

Gasdaska, J.R., et al., "Advantages of Therapeutic Protein Production in the Aquatic Plant Lemna," Bioprocessing Journal 2(2):49-56, Williamsburg Bioprocessing Foundation, United States (2003).

GenBank, "Rice alpha-amylase mRNA, complete cds, clone pOS103" Accession No. M24286.1, accessed at http://www.ncbi.nlm.nih.gov/nuccore/M24286, accessed on Dec. 12, 2015, 2 pages.

GenBank, "Lemna minor alpha-1,3-fucosyltransferase (Fuct1) mRNA, complete cds" Accession No. DQ789145.1, accessed at http://www.ncbi.nlm.nih.gov/nuccore/DQ789145, accessed on Dec. 12, 2015, 2 pages.

GenBank, "Lemna minor beta-1,2-xylosyltransferase isoform 1 (Xylt1) mRNA, partial cds" Accession No. DQ789146.1, accessed at http://www.ncbi.nlm.nih.gov/nuccore/DQ789146, accessed on Dec. 12, 2015, 2 pages.

Graf, H., et al., "Ion Exchange Resins for the Purification of Monoclonal Antibodies from Animal Cell Culture," Bioseparation 4(1):7-20, Kluwer Academic Publishers, Netherlands (1994).

Hepburn, A.G., et al., "The Use of pNJ5000 as an intermediate Vector for the Genetic Manipulation of Agrobacterium Ti-plasmids," Journal of General Microbiology 131(11):2961-2969, Society for General Microbiology, England (1985).

Huls, G., et al., "Antitumor Immune Effector Mechanisms Recruited by Phage Display-derived Fully Human IgG1 and IgA1 Monoclonal Antibodies," Cancer Research 59(22):5778-5784, American Association for Cancer Research, United States (1999).

Iansante, V., et al., "Biotechnological Approaches for the Treatment of Inflammatory Diseases," Anti-Inflammatory and Anti-Allergy Agents in Medicinal Chemistry 8(1);51-71 (2009).

International Search Report and Written Opinion for International Application No. PCT/EP2012/075670, European Patent Office, Netherlands, mailed on Apr. 12, 2013, 14 pages.

International Search Report and Written Opinion for International Application No. PCT/EP2012/075671, European Patent Office, Netherlands, mailed on May 7, 2013, 14 pages.

International Search Report and Written Opinion for International Application No. PCT/EP2012/075672, European Patent Office, Netherlands, mailed on Mar. 21, 2013, 14 pages.

International Search Report and Written Opinion for International Application No. PCT/EP2012/075673, European Patent Office, Netherlands, mailed on Apr. 5, 2013, 13 pages.

(56) References Cited

OTHER PUBLICATIONS

Jefferis, R., "Glycosylation as a Strategy to Improve Antibody-based Therapeutics," Nature Reviews, Drug Discovery 8(3):226-234, Macmillan Publishers Ltd., England (2009).
Kalliolias, G.D. and Ivashkiv, L.B., "Targeting Cytokines in Inflammatory Diseases: Focus on Interleukin-1-mediated Autoinflammation," F1000 Biology Reports 1:70, Faculty of 1000, England (2009).
Karnoup, A.S., et al., "O-linked Glycosylation in Maize-expressed Human IgA1," Glycobiology 15(10):965-981, Oxford University Press, England (2005).
Knight, D.M., et al., "Construction and Initial Characterization of a Mouse-human Chimeric Anti-TNF Antibody," Molecular Immunology 30(16):1443-1453, Pergamon Press, England (1993).
Lash, A., "Making the Case for Antibody-Drug Conjugates," In Vivo: The Business and Medicine Report 28(11):32-38, Informa Business Information, Inc., England(2010).
Lohse, S., et al., "Recombinant Dimeric IgA Antibodies Against the Epidermal Growth Factor Receptor Mediate Effective Tumor Cell Killing," Journal of Immunology 186(6):3770-3778, American Association of Immunologists, United States (2011).
MA, J.K-C., et al., "Characterization of a Recombinant Plant Monoclonal Secretory Antibody and Preventive Immunotherapy in Humans," Nature Medicine 4(5):601-606, Nature Publishing Company, United States (1998).
MA, J.K.-C, et al., "Generation and Assembly of Secretory Antibodies in Plants," Science 268(5211):716-719, American Association for the Advancement of Science, United States (1995).
MA, J.K.-C., et al., "The Production of Recombinant Pharmaceutical Proteins in Plants," Nature Reviews Genetics 4(10):794-805, Nature Publishing Group, England (2003).
Maddox, D.E., et al., "Elevated Serum Levels in Human Pregnancy of a Molecule Immunochemically Similar to Eosinophil Granule Major Basic Protein," Journal of Experimental Medicine 158(4):1211-1226, Rockefeller University Press, United States (1983).
Morelle, W. and Michalski, J.C., "The Mass Spectrometric Analysis of Glycoproteins and their Glycan Structures," Current Analytical Chemistry 1(1):29-57, Bentham Science Publishers, United Arab Emirates (2005).
Morlot, C., et al., "Cloning, Expression, Crystallization and Preliminary X-ray Analysis of the First Two Ig Domains from Human Roundabout 1 (Robo1)," Acta Crystallographica. Section F 63:689-691, Wiley-Blackwell, England (2007).
Negrouk, V., et al., "Highly Efficient Transient Expression of Functional Recombinant Antibodies in Lettuce," Plant Science 169(2):433-438, Elsevier Ireland Ltd., Ireland (2005).
Nguyen, L.V., et al, "Genetic Engineering of a Lemna Isoleucine Auxotroph," Transgenic Research 21(5):1071-1083, Springer Science and Business Media B.V., Netherlands (2012).
Ni, M., et al., "Strength and Tissue Specificity of Chimeric Promoters Derived from the Octopine and Mannopine Synthase Genes," The Plant Journal 7(4):661-676, John Wiley and Sons, United States (1995).
Pabst, O., "New Concepts in the Generation and Functions of IgA," Nature Reviews Immunology 12(12):821-832, Macmillan Publishers Limited, England (2012).
Pleass, R.J., et al., "Novel Antimalarial Antibodies Highlight the Importance of the Antibody Fc Region in Mediating Protection," Blood 102(13):4424-4430, American Society of Hematology, United States (2003).
Preston, M.J., et al., "Production and Characterization of a Set of Mouse-human Chimeric Immunoglobulin G (IgG) Subclass and IgA Monoclonal Antibodies with Identical Variable Regions Specific for Pseudomonas Aeruginosa Serogroup O6 Lipopolysaccharide," Infection and Immunity 66(9):4137-4142, American Society for Microbiology, United States (1998).
Reichert, J.M, "Antibody-based Therapeutics to Watch in 2011," mAbs 3(1):76-99, Landes Bioscience, United States (2011).

Reichert, J.M., "Which are the Antibodies to Watch in 2012?," mAbs 4(1):1-3, Landes Biosciences, United States (2012).
Reimund, J.M., et al., "Anti-Tumor Necrosis Factor-alpha (TNF-α) Treatment Strategies in Crohn's Disease," Recent Patents on Inflammation and Allergy Drug Discovery 1(1):21-34, Bentham Science Publishers, United Arab Emirates (2007).
Schenk, R.U. and Hildebrandt, A.C., "Medium and Techniques for Induction and Growth of Monocotyledonous and Dicotyledonous Plant Cell Cultures," Canadian Journal of Botany 50(1):199-204, Canadian Science Publishers, Canada (1972).
Senior, B.W. and Woof, J.M., "The Influences of Hinge Length and Composition on the Susceptibility of Human IgA to Cleavage by Diverse Bacterial IgA1 Proteases," Journal of Immunology 174(12):7792-7799, American Association of Immunologists, United States (2005).
Snoeck, V., et al., "The IgA System: A Comparison of Structure and Function in Different Species," Veterinary Research 37(3):455-467, IRA/EDP Sciences, France (2006).
Stubbe, H., et al., "Polymeric IgA is Superior to Monomeric IgA and IgG Carrying the Same Variable Domain in Preventing Clostridium Difficile Toxin A Damaging of T84 Monolayers," Journal of Immunology 164(4):1952-1960, American Association of Immunologists, United States (2000).
Sun, L.K., et al, "Human IgA Monoclonal Antibodies Specific for a Major Ragweed Pollen Antigen," Biotechnology 13(8):779-786, Nature Publishing Company, United States (1995).
Synthon: LEX System Overview, Sep. 2012, Retrieved from the Internet: URL:http://www.molecularfarming.org/FA0804_Dickey_Warsaw_2012.pdf, retrieved on Feb. 26, 2013, 34 pages.
Vajdos, F.F., et al., "Comprehensive Functional Maps of the Antigen-Binding Site of an Anti-ErbB2 Antibody obtained with Shotgun Scanning Mutagenesis," Journal of Molecular Biology 320(2):415-428, Elsevier Science, United States (2002).
Van Der Vossen, E.A., et al., "Role of the 5' Leader Sequence of Alfalfa Mosaic Virus RNA 3 in Replication and Translation of the Viral RNA," Nucleic Acids Research 21(6):1361-1367, Oxford University Press, England (1993).
Van Engelen, F.A., et al., "Coordinate Expression of Antibody Subunit Genes Yields High Levels of Functional Antibodies in Roots of Transgenic Tobacco," Plant Molecular Biology 26(6):1701-1710, Kluwer Academic, Netherlands (1994).
Van Engelen, F.A., et al., "pBINPLUS: An Improved Plant Transformation Vector Based on pBIN19," Transgenic Research 4(4):288-290, Chapman & Hall, England (1995).
Vidarsson, G., et al., "Activity of Human IgG and IgA Subclasses in Immune Defense Against Neisseria Meningitidis Serogroup B," Journal of Immunology 166(10):6250-6256, American Association of Immunologists, United States (2001).
Wang, L. and Roossinck, M.J., "Comparative Analysis of Expressed Sequences Reveals a Conserved Pattern of Optimal Codon Usage in Plants," Plant Molecular Biology 61(4-5):699-710, Springer Science and Business Media B.V., Netherlands (2006).
Worledge, K.L., et al., "Oral Administration of Avian Tumor Necrosis Factor Antibodies Effectively Treats Experimental Colitis in Rats," Digestive Diseases and Sciences 45(12):2298-2305, Plenam Publishing Corporation, United States (2000).
Wycoff, K.L., "Secretory IgA Antibodies from Plants," Current Pharmaceutical Design 11(19):2429-2437, Bentham Science Publishers, United Arab Emirates (2005).
Yamashita, M., et al., "Recent Advances in the Generation of Human Monoclonal Antibody," Cytotechnology 55(2-3):55-60, Springer Science and Business Media B.V., Netherlands (2007).
Ye, D., et al., "Molecular Mechanism of Tumor Necrosis Factor-alpha Modulation of Intestinal Epithelial Tight Junction Barrier," American Journal of Physiology. Gastrointestinal and Liver Physiology 290(3):G496-G504, American Physiological Society, United States (2006).
Non-final Office Action in U.S. Appl. No. 14/365,867, mailed Nov. 6, 2015, Gerardus et al., filed Jun. 16, 2014.
Non-final Office Action in U.S. Appl. No. 14/365,839, mailed Jan. 8, 2016, Gerardus et al., filed Jun. 16, 2014.

* cited by examiner

FIGURE 1

```
                |                           Cα1
α1       ASPTSPKVFPLSLCSTQPDGNVVIACLVQGFFPQEPLSVTWSESGQGVTARNFPPSQDAS
α2m(1)   ASPTSPKVFPLSLDSTPQDGNVVVACLVQGFFPQEPLSVTWSESGQNVTARNFPPSQDAS
α2m(2)   ASPTSPKVFPLSLDSTPQDGNVVVACLVQGFFPQEPLSVTWSESGQNVTARNFPPSQDAS
α2(n)    ASPTSPKVFPLSLDSTPQDGNVVVACLVQGFFPQEPLSVTWSESGQNVTARNFPPSQDAS
         .........|...^..^^.|...^.....|..........|..........^..|..........|
         1        10        20        30        40        50        60
                                                        | |  Hinge
α1       GDLYTTSSQLTLPATQCLAGKSVTCHVKHYTNPSQDVTVPCPVPSTPPTPSPSTPPTPSP
α2m(1)   GDLYTTSSQLTLPATQCPDGKSVTCHVKHYTNPSQDVTVPCPVP              PPP
α2m(2)   GDLYTTSSQLTLPATQCPDGKSVTCHVKHYTNSSQDVTVPCRVP              PPP
α2(n)    GDLYTTSSQLTLPATQCPDGKSVTCHVKHYTNSSQDVTVPCRVP              PPP
         .........|.......^^|..........|.^......|.^........|..........|
                  70        80        90       100       110       120
         /|                             Cα2
α1       SCCHPRLSLHRPALEDLLLGSEANLTCTLTGLRDASGVTFTWTPSSGKSAVQGPPERDLC
α2m(1)   PCCHPRLSLHRPALEDLLLGSEANLTCTLTGLRDASGATFTWTPSSGKSAVQGPPERDLC
α2m(2)   PCCHPRLSLHRPALEDLLLGSEANLTCTLTGLRDASGATFTWTPSSGKSAVQGPPERDLC
α2(n)    PCCHPRLSLHRPALEDLLLGSEANLTCTLTGLRDASGATFTWTPSSGKSAVQGPPERDLC
         .........|..........|..........|.......^.|..........|..........|
                  130       140       150       160       170       180
                                                        | |
α1       GCYSVSSVLPGCAEPWNHGKIFTCTAAYPESKTPLTATLSKSGNTFRPEVHLLPPPSEEL
α2m(1)   GCYSVSSVLPGCAQPWNHGETFTCTAAHPELKTPLTANITKSGNTFRPEVHLLPPPSEEL
α2m(2)   GCYSVSSVLPGCAQPWNHGETFTCTAAHPELKTPLTANITKSGNTFRPEVHLLPPPSEEL
α2(n)    GCYSVSSVLPGCAQPWNHGETFTCTAAHPELKTPLTANITKSGNTFRPEVHLLPPPSEEL
         .........|...^......^.....|.^|.^......^^^..........|..........|
                  190       200       210       220       230       240
                                   Cα3
α1       ALNELVTLTCLARGFSPKDVLVRWLQGSQELPREKYLTWASRQEPSQGTTTFAVTSILRV
α2m(1)   ALNELVTLTCLARGFSPKDVLVRWLQGSQELPREKYLTWASRQEPSQGTTTFAVTSILRV
α2m(2)   ALNELVTLTCLARGFSPKDVLVRWLQGSQELPREKYLTWASRQEPSQGTTTYAVTSILRV
α2(n)    ALNELVTLTCLARGFSPKDVLVRWLQGSQELPREKYLTWASRQEPSQGTTTFAVTSILRV
         .........|..........|..........|..........|..........|.^........|
                  250       260       270       280       290       300
                                                   | |  Tailpiece
α1       AAEDWKKGDTFSCMVGHEALPLAFTQKTIDRLAGKPTHVNVSVVMAEVDGTCY
α2m(1)   AAEDWKKGDTFSCMVGHEALPLAFTQKTIDRLAGKPTHVNVSVVMAEVDGTCY
α2m(2)   AAEDWKKGETFSCMVGHEALPLAFTQKTIDRLAGKPTHINVSVVMAEADGTCY
α2(n)    AAEDWKKGDTFSCMVGHEALPLAFTQKTIDRLAGKPTHVNVSVVMAEVDGTCY
         .........^|..........|..........|.........^|........^.|...
                   310       320       330       340       353
```

FIGURE 2A
```
LPAQVAFTPYAPEPGSTCRLREYYDQTAQMCCSKCSPGQHAKVFCTKTSDTVCDSCEDST
....|....|....|....|....|....|....|....|....|....|....|....|
    10        20        30        40        50        60

YTQLWNWVPECLSCGSRCSSDQVETQACTREQNRICTCRPGWYCALSKQEGCRLCAPLRK
....|....|....|....|....|....|....|....|....|....|....|....|
    70        80        90       100       110       120

CRPGFGVARPGTETSDVVCKPCAPGTFSNTTSSTDICRPHQICNVVAIPGNASMDAVCTS
....|....|....|....|....|....|....|....|....|....|....|....|
   130       140       150       160       170       180

TSPTRSMAPGAVHLPQPVSTRSQHTQPTPEPSTAPSTSFLLPMGPSPPAEGSTGD
....|....|....|....|....|....|....|....|....|....|....|
   190       200       210       220       230
```

FIGURE 2B
```
        FR1                |--CDR1--|    FR2         |----CDR2--
EVKLEESGGGLVQPGGSMKLSCVASGFIFSNHWMNWVRQSPEKGLEWVAEIRSKSINSAT
....|....|....|....|....|....|....|....|....|....|....|....|
1        10        20        30        40        50        60

-------|           FR3                 |-CDR3--|    FR4
HYAESVKGRFTISRDDSKSAVYLQMTDLRTEDTGVYYCSRNYYGSTYDYWGQGTILTVSS
....|....|....|....|....|....|....|....|....|....|....|....|
         70        80        90       100       110       120
```

FIGURE 2C
```
        FR1              |--CDR1---|    FR2          |-CDR2|
DILLTQSPAILSVSPGERVSFSCRASQFVGSSIHWYQQRTNGSPRLLIKYASESMSGIPS
....|....|....|....|....|....|....|....|....|....|....|....|
1        10        20        30        40        50        60

FR3                   |--CDR3-|   FR4
RFSGSGSGTDFTLSINTVESEDIADYYCQQSHSWPFTFGSGTNLEVK
....|....|....|....|....|....|....|
         70        80        90       100    107
```

FIGURE 2D
```
        FR1                |--CDR1--|    FR2         |----CDR2--
EVQLVESGGGLVQPGRSLRLSCAASGFTFDDYAMHWVRQAPGKGLEWVSAITWNSGHIDY
....|....|....|....|....|....|....|....|....|....|....|....|
1        10        20        30        40        50        60

-----|            FR3                  |-CDR3--|    FR4
ADSVEGRFTISRDNAKNSLYLQMNSLRAEDTAVYYCAKVSYLSTASSLDYWGQGTLVTVSS
....|....|....|....|....|....|....|....|....|....|....|....|.
         70        80        90       100       110       121

```

FIGURE 2E
```
        FR1              |--CDR1---|    FR2          |-CDR2|
DIQMTQSPSSLSASVGDRVTITCRASQGIRNYLAWYQQKPGKAPKLLIYAASTLQSGVPS
....|....|....|....|....|....|....|....|....|....|....|....|
1        10        20        30        40        50        60

FR3              |--CDR3-|   FR4
RFSGSGSGTDFTLTISSLQPEDVATYYCQRYNRAPYTFGQGTKVEIK
....|....|....|....|....|
         70        80        90       100    107
```

FIGURE 2F

```
          FR1                  |--CDR1--|      FR2           |----CDR2--
QVQLVESGGGVVQPGRSLRLSCAASGFIFSSYAMHWVRQAPGNGLEWVAFMSYDGSNKKY
.........|.........|.........|.........|.........|.........|
1        10        20        30        40        50        60

-----|            FR3                         |------CDR3-----|    FR4
ADSVKGRFTISRDNSKNTLYLQMNSLRAEDTAVYYCARDRGIAAGGNYYYYGMDVWGQGTTVTVSS
.........|.........|.........|.........|.........|.........|.........|...
         70        80        90        100       110       120     126
```

FIGURE 2G

```
          FR1                 |--CDR1---|      FR2           |-CDR2|
EIVLTQSPATLSLSPGERATLSCRASQSVYSYLAWYQQKPGQAPRLLIYDASNRATGIPA
.........|.........|.........|.........|.........|.........|
1        10        20        30        40        50        60
         FR3                       |--CDR3--|   FR4
RFSGSGSGTDFTLTISSLEPEDFAVYYCQQRSNWPPFTFGPGTKVDIK
.........|.........|.........|.........|........
         70        80        90        100      108
```

FIGURE 2H

```
          FR1                  |--CDR1--|      FR2           |----CDR2--
EVQLVESGGGLVQPGGSLRLSCAASGYVFTDYGMNWVRQAPGKGLEWMGWINTYIGEPIY
.........|.........|.........|.........|.........|.........|
1        10        20        30        40        50        60

-----|            FR3                       |--CDR3-|    FR4
ADSVKGRFTFSLDTSKSTAYLQMNSLRAEDTAVYYCARGYRSYAMDYWGQGTLVTVSS
.........|.........|.........|.........|.........|.........|
         70        80        90        100       110      118
```

FIGURE 2I

```
          FR1                 |--CDR1---|      FR2           |-CDR2|
DIQMTQSPSSLSASVGDRVTITCKASQNVGTNVAWYQQKPGKAPKALIYSASFLYSGVPY
.........|.........|.........|.........|.........|.........|
1        10        20        30        40        50        60
         FR3                       |--CDR3-|   FR4
RFSGSGSGTDFTLTISSLQPEDFATYYCQQYNIYPLTFGQGTKVEIK
.........|.........|.........|.........|.......
         70        80        90        100     107
```

FIGURE 3A

```
            |                          CL
κ    RTVAAPSVFIFPPSDEQLKSGTASVVCLLNNFYPREAKVQWKVDNALQSGNSQESVTEQD
     .........|.........|.........|.........|.........|.........|
     1        10        20        30        40        50        60

|
     SKDSTYSLSSTLTLSKADYEKHKVYACEVTHQGLSSPVTKSFNRGEC
     .........|.........|.........|.........|.......
              70        80        90        100   107
```

FIGURE 3B

```
            |                          CL
λ1   GQPKANPTVTLFPPSSEELQANKATLVCLISDFYPGAVTVAWKADGSPVKAGVETTKPSK
λ2   GQPKAAPSVTLFPPSSEELQANKATLVCLISDFYPGAVTVAWKADSSPVKAGVETTTPSK
λ3   GQPKAAPSVTLFPPSSEELQANKATLVCLISDFYPGAVTVAWKADSSPVKAGVETTTPSK
λ6   GQPKAAPSVTLFPPSSEELQANKATLVCLISDFYPGAVKVAWKADGSPVNTGVETTTPSK
λ7   GQPKAAPSVTLFPPSSEELQANKATLVCLVSDFYPGAVTVAWKADGSPVKVGVETTKPSK
     .........|.........|.........|.........|.........|.........|
     1        10        20        30        40        50        60

|
     QSNNKYAASSYLSLTPEQWKSHRSYSCQVTHEGSTVEKTVAPTECS
     QSNNKYAASSYLSLTPEQWKSHRSYSCQVTHEGSTVEKTVAPTECS
     QSNNKYAASSYLSLTPEQWKSHKSYSCQVTHEGSTVEKTVAPTECS
     QSNNKYAASSYLSLTPEQWKSHRSYSCQVTHEGSTVEKTVAPAECS
     QSNNKYAASSYLSLTPEQWKSHRSYSCRVTHEGSTVEKTVAPAECS
     .........|.........|.........|.........|......
              70        80        90        100   106
```

FIGURE 4

```
QEDERIVLVDNKCKCARITSRIIRSSEDPNEDIVERNIRIIVPLNNRENISDPTSPLRTR
.........|.........|.........|.........|.........|.........|
1        10        20        30        40        50        60

FVYHLSDLCKKCDPTEVELDNQIVTATQSNICDEDSATETCYTDRNKCYTAVVPLVYGG
.........|.........|.........|.........|.........|.........|
         70        80        90        100       110       120

ETKMVETALTPDACYPD
.........|.......
         130   137
```

FIGURE 5

```
KSPIFGPEEVNSVEGNSVSITCYYPPTSVNRHTRKYWCRQGARGGCITLISSEGYVSSKY
..........|..........|..........|..........|..........|..........|
1         10         20         30         40         50         60

AGRANLTNFPENGTFVVNIAQLSQDDSGRYKCGLGINSRGLSFDVSLEVSQGPGLLNDTK
..........|..........|..........|..........|..........|..........|
          70         80         90        100        110        120

VYTVDLGRTVTINCPFKTENAQKRKSLYKQIGLYPVLVIDSSGYVNPNYTGRIRLDIQGT
..........|..........|..........|..........|..........|..........|
         130        140        150        160        170        180

GQLLFSVVINQLRLSDAGQYLCQAGDDSNSNKKNADLQVLKPEPELVYEDLRGSVTFHCA
..........|..........|..........|..........|..........|..........|
         190        200        210        220        230        240

LGPEVANVAKFLCRQSSGENCDVVVNTLGKRAPAFEGRILLNPQDKDGSFSVVITGLRKE
..........|..........|..........|..........|..........|..........|
         250        260        270        280        290        300

DAGRYLCGAHSDGQLQEGSPIQAWQLFVNEESTIPRSPTVVKGVAGSSVAVLCPYNRKES
..........|..........|..........|..........|..........|..........|
         310        320        330        340        350        360

KSIKYWCLWEGAQNGRCPLLVDSEGWVKAQYEGRLSLLEEPGNGTFTVILNQLTSRDAGF
..........|..........|..........|..........|..........|..........|
         370        380        390        400        410        420

YWCLTNGDTLWRTTVEIKIIEGEPNLKVPGNVTAVLGETLKVPCHFPCKFSSYEKYWCKW
..........|..........|..........|..........|..........|..........|
         430        440        450        460        470        480

NNTGCQALPSQDEGPSKAFVNCDENSRLVSLTLNLVTRADEGWYWCGVKQGHFYGETAAV
..........|..........|..........|..........|..........|..........|
         490        500        510        520        530        540

YVAVEERKAAGSRDVSLAKADAAPDEKVLDSGFREIENKAIQDPR
..........|..........|..........|..........|.....
         550        560        570        580  585
```

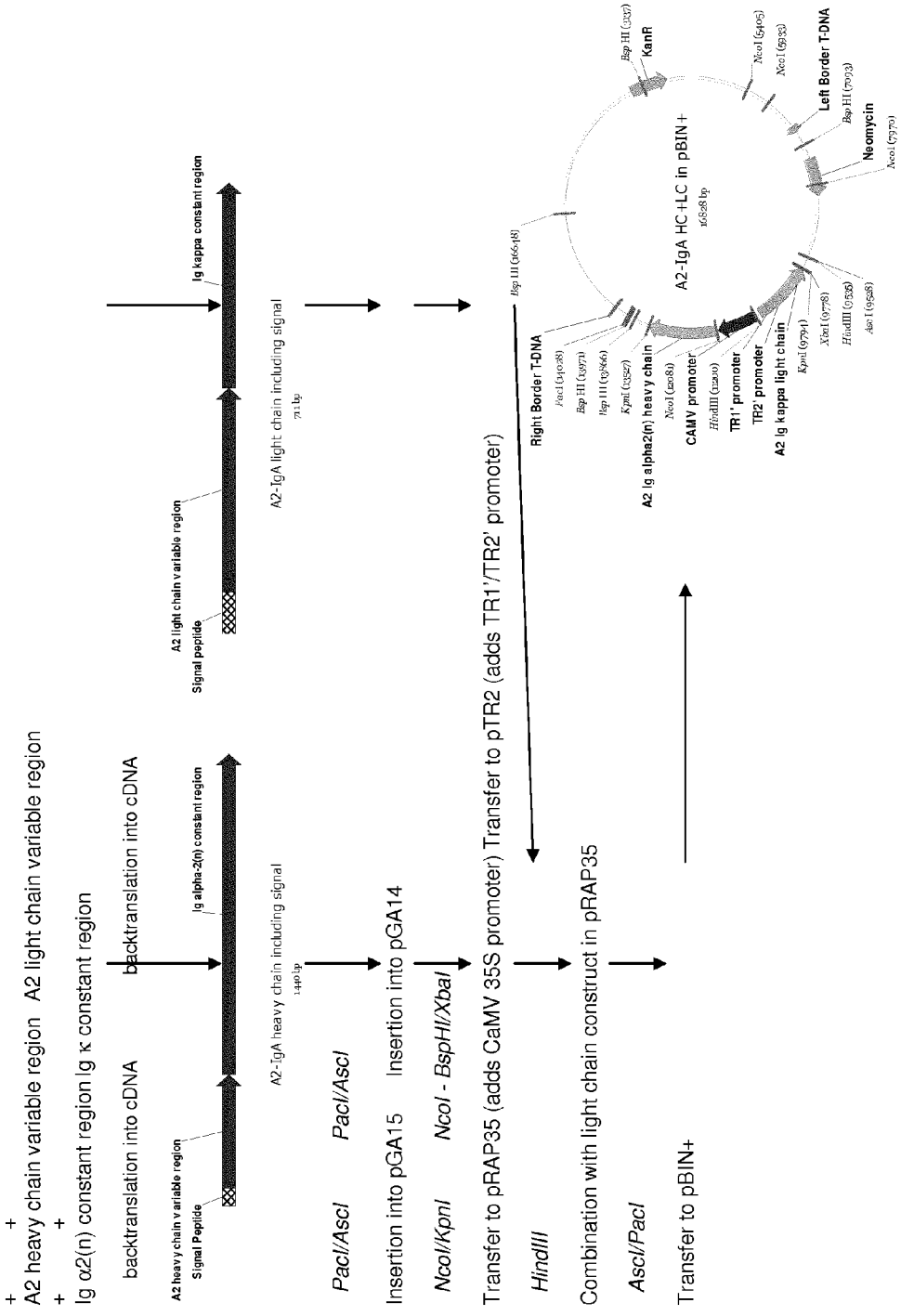

FIGURE 17A

```
         FR1                  |--CDR1--|      FR2           |----CDR2--
EVQLVQSGAEVKKPGESLKISCKGSGYSFTTYWLGWVRQMPGKGLDWIGIMSPVDSDIRY
.........|.........|.........|.........|.........|.........|
1        10        20        30        40        50        60

-----|           FR3                  |--CDR3--|    FR4
SPSFQGQVTMSVDKSITTAYLQWNSLKASDTAMYYCARRRPGQGYFDFWGQGTLVTVSS
.........|.........|.........|.........|.........|........
         70        80        90        100       110      119
```

FIGURE 17B

```
         FR1             |--CDR1---|     FR2          |-CDR2|
DIQMTQSPSSLSASVGDRVTITCRASQGISSWLAWYQQKPEKAPKSLIYAASSLQSGVPS
.........|.........|.........|.........|.........|.........|
1        10        20        30        40        50        60

FR3               |--CDR3-|    FR4
RFSGSGSGTDFTLTISSLQPEDFATYYCQQYNIYPYTFGQGTKLEIK
.........|.........|.........|.........|.......
         70        80        90        100  107
```

FIGURE 17C

```
         FR1                    |CDR1|      FR2          |----CDR2--
QVQLVESGGGVVQPGRSLRLSCAASGFTFSSYGMHWVRQAPGKGLEWVAFIRYDGSNKYY
.........|.........|.........|.........|.........|.........|
1        10        20        30        40        50        60

-----|          FR3                  |CDR3|     FR4
ADSVKGRFTISRDNSKNTLYLQMNSLRAEDTAVYYCKTHGSHDNWGQGTMVTVSS
.........|.........|.........|.........|.........|.....
         70        80        90        100       110 115
```

FIGURE 17D

```
         FR1         |----CDR1----|      FR2         |-CDR2|
QSVLTQPPSVSGAPGQRVTISCSGSRSNIGSNTVKWYQQLPGTAPKLLIYYNDQRPSGVP
.........|.........|.........|.........|.........|.........|
1        10        20        30        40        50        60

FR3               |---CDR3---|   FR4
DRFSGSKSGTSASLAITGLQAEDEADYYCQSYDRYTHPALLFGTGTKVTVL
.........|.........|.........|.........|.......
         70        80        90        100    111
```

FIGURE 20
A
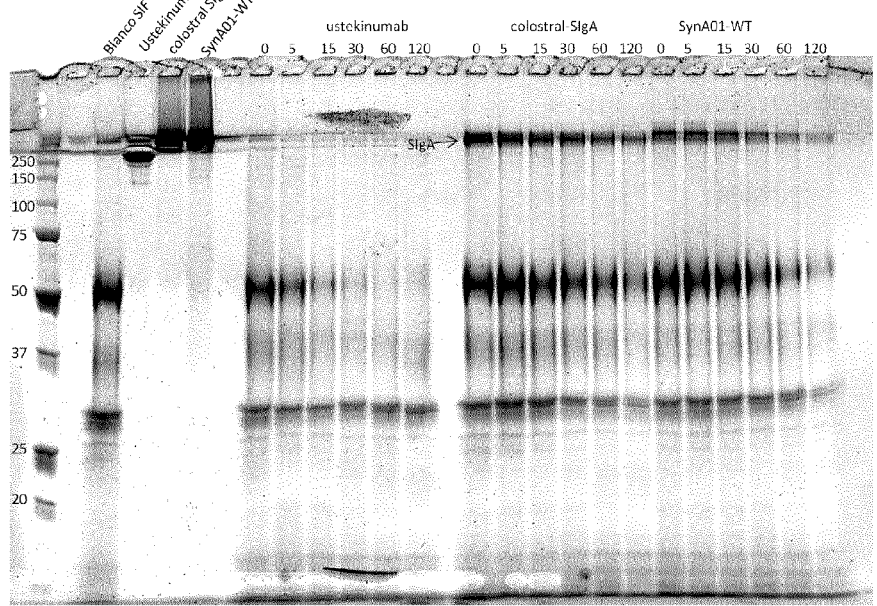
B
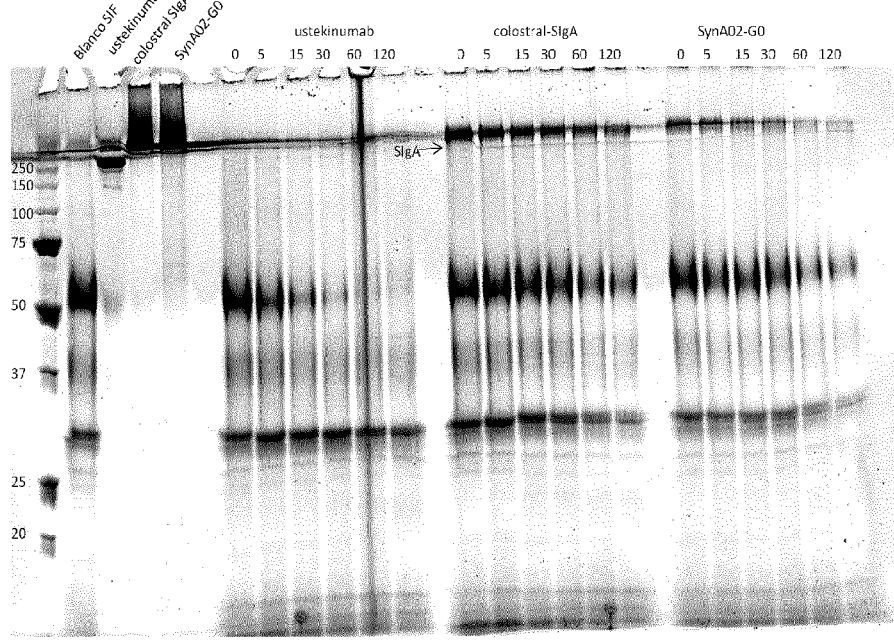

MONOCLONAL ANTIBODIES TO HUMAN PROINFLAMMATORY CYTOKINES AND METHODS FOR TREATING INFLAMMATORY DISEASES

This application claims the benefit of priority under 35 U.S.C. §119(e) from U.S. provisional patent application Ser. No. 61/576,727, filed Dec. 16, 2011, and Ser. No. 61/576,922, filed Dec. 16, 2011; the entire contents of each provisional application being incorporated herein by reference.

FIELD OF THE INVENTION

The present invention relates to monoclonal secretory IgA antibodies that bind to and neutralize one or more human proinflammatory cytokines, or bind to and block a human receptor of a human proinflammatory cytokine. The antibodies are useful in treating inflammatory diseases in humans.

BACKGROUND OF THE INVENTION

Inflammation represents a key event of many diseases, such as psoriasis, inflammatory bowel diseases, rheumatoid arthritis, asthma, multiple sclerosis, atherosclerosis, cystic fibrosis, and sepsis. Inflammatory cells, such as neutrophils, eosinophils, basophils, mast cells, macrophages, endothelial cells, and platelets, respond to inflammatory stimuli and foreign substances by producing bioactive mediators. These mediators act as autocrines and paracrines by interacting with many cell types to promote the inflammatory response. There are many mediators that can promote inflammation, such as cytokines and their receptors, adhesion molecules and their receptors, antigens involved in lymphocyte activation, and IgE and its receptors.

Cytokines, for example, are soluble proteins that allow for communication between cells and the external environment. The term cytokines includes a wide range of proteins, such as lymphokines, monokines, interleukins, colony stimulating factors, interferons, tumor necrosis factors, and chemokines. Cytokines serve many functions, including controlling cell growth, migration, development, and differentiation, and mediating and regulating immunity, inflammation, and hematopoiesis. Even within a given function, cytokines can have diverse roles. For example, in the context of mediating and regulating inflammation, some cytokines inhibit the inflammatory response (anti-inflammatory cytokines), others promote the inflammatory response (pro-inflammatory cytokines). And certain cytokines fall into both categories, i.e., can inhibit or promote inflammation, depending on the situation. The targeting of proinflammatory cytokines to suppress their natural function, such as with antibodies, is a well-established strategy for treating various inflammatory diseases.

Many inflammatory diseases are treated by targeting proinflammatory cytokines with antibodies. Most (if not all) of the anti-proinflammatory cytokine antibodies currently on the market, and those currently in clinical trials, are of the IgG class. See, for example, *Nature Reviews*, vol. 10, pp. 301-316 (2010); *Nature Medicine*, vol. 18, pp. 736-749 (2012); *Nature Biotechnology*, vol. 30, pp. 475-477 (2012); *Anti-Inflammatory & Anti-Allergy Agents in Medicinal Chemistry*, vol. 8, pp. 51-71 (2009); F1000.com/Reports/Biology/content/1/70, *F1000 Biology Reports*, 1:70 (2009); *mAbs* 4:1, pp. 1-3 (2012); *mAbs* 3:1, pp. 76-99 (2011); clinicaltrials.gov (generally), and clinicaltrialsregister.eu/ (generally). These IgG antibodies are administered systemically and thus are often associated with unwanted side effects, which can include one or more of, for example, infusion reactions and immunogenicity, hypersensitivity reactions, immunosuppression and infections, heart problems, liver problems, and others. Additionally the suppression of the target cytokines at non-diseased parts of the body can lead to unwanted effects.

In an attempt to reduce side effects associated with systemic treatment and to eliminate the inconvenience and expense of infusions, an article proposed an oral anti-TNF therapy that could be useful in treating Crohn's disease. Worledge et al. "Oral Administration of Avian Tumor Necrosis Factor Antibodies Effectively Treats Experimental Colitis in Rats." *Digestive Diseases and Sciences* 45(12); 2298-2305 (December 2000). This article describes immunizing hens with recombinant human TNF and an adjuvant, fractionating polyclonal yolk antibody (IgY, which in chickens is the functional equivalent to IgG), and administering the unformulated polyclonal IgY (diluted in a carbonate buffer to minimize IgY acid hydrolysis in the stomach) to rats in an experimental rodent model of colitis. The rats were treated with 600 mg/kg/day of the polyclonal IgY. The uses of animal antibodies and polyclonal antibodies, however, are undesirable.

In a similar attempt to avoid adverse events associated with systemic administration, another group, Avaxia Biologics Inc., describes a topical (e.g., oral or rectal) animal-derived polyclonal anti-TNF composition that could be useful in treating inflammation of the digestive tract, such as inflammatory bowel disease. WO2011047328. The application generally states that preferably the polyclonal antibody composition is prepared by immunizing an animal with a target antigen, and the preferably the polyclonal antibody composition is derived from milk or colostrum with bovine colostrums being preferred (e.g., p. 14). The application also generally states that the animal derived polyclonal antibodies could be specific for (among other targets) other inflammatory cytokines (e.g., pp. 6-7). This application describes working examples in which cows were immunized with murine TNF and the colostrum was collected post-parturition to generate bovine polyclonal anti-TNF antibodies (designated as AVX-470). The uses of animal-derived antibodies and polyclonal antibodies, however, are undesirable.

IgA molecular forms have been proposed as treatments for various diseases, most notably as treatments for pollen allergies, as treatments against pathogens, and as treatments for cancer.

For example, one article describes anti-AmbαI (a ragweed pollen antigen) humanized monomeric IgA and dimeric IgA antibodies made in murine cells (NS0 and Sp2/0 cells). The dimeric IgA contains a mouse J-chain. The article proposes that the antibodies may be applied to a mucosal surface or the lower airway to inhibit entry of allergenic molecules across the mucosal epithelium and therefore to prevent the development of allergic response. Sun et al. "Human IgA Monoclonal Antibodies Specific for a Major Ragweed Pollen Antigen." *Nature Biotechnology* 13, 779-786 (1995).

Several other articles propose the use of IgA antibodies as a defense against pathogens.

Two articles proposed the use of an anti-streptococcal antigen I/II secretory IgA-G hybrid antibody. Ma et al. "Generation and Assembly of Secretory Antibodies in Plants." *Science* 268(5211), 716-719 (May 1995); Ma et al. "Characterization of a Recombinant Plant Monoclonal Secretory Antibody and Preventive Immunotherapy in Humans." *Nature Medicine* 4(5); 601-606 (May 1998). The hybrid antibody contains murine monoclonal kappa light chain, hybrid Ig A-G heavy chain, murine J-Chain, and rabbit secretory component. The antibody was made by successive sexual crossing between four transgenic *N. tabacum* plants and filial recombinants to form plant cells that expressed all four protein chains simultaneously. The parent antibody (the source of the antigen binding regions, is identified as the IgG antibody Guy's 13. The group proposes that although sIgA may provide an advantage over IgG in the mucosal environment, such is not always the case (1998 Ma at p. 604, right column).

A related article identifies the anti-streptococcal antigen I/II secretory IgA-G hybrid antibody, which was derived from Guy's 13 IgA, as CaroRx. Wycoff. "Secretory IgA Antibodies from Plants." *Current Pharmaceutical Design* 10(00); 1-9 (2004). Planet Biotechnology Inc. This related article states that the CaroRx antibody was designed to block adherence to teeth of the bacteria that causes cavities. Apparently, the CaroRx antibody was difficult to purify; the affinity of Protein A for the murine Ig domain was too low and protein G was necessary for sufficient affinity chromatography. Furthermore, the article states that several other chromatographic media had shown little potential as purification steps for the hybrid sIgA-G from tobacco leaf extracts. The article also indicates that the authors were unable to control for human-like glycosylation in tobacco, but that such was not a problem because people are exposed to plant glycans every day in food without ill effect.

WO9949024, which lists Wycoff as an inventor, Planet Biotechnology Inc. as the applicant, describes the use of the variable regions of Guy's 13 to make a secretory antibody from tobacco. The application contains only two examples—the first a working example and the second a prophetic example. Working Example 1 describes the transient production of an anti-*S. mutans* SA I/III (variable region from Guy's 13) in tobacco. The tobacco plant was transformed using particle bombardment of tobacco leaf disks. Transgenic plants were then screened by Western blot "to identify individual transformants expressing assembled human sIgA" (p. 25). Prophetic Example 2 states that in a transformation system for *Lemna gibba* (a monocot), bombardment of surface-sterilized leaf tissue with DNA-coated particles "is much the same as with" tobacco (a dicot). The prophetic example also stops at screening by immunoblot analysis for antibody chains and assembled sIgA, and states that the inventors "expect to find fully assembled sIgA."

Another article proposed the use of an anti-RSV glycoprotein F IgA antibodies (mIgA, dIgA, and sIgA). Berdoz et al. "In vitro Comparison of the Antigen-Binding and Stability Properties of the Various Molecular Forms of IgA antibodies Assembled and Produced in CHO Cells." *Proc. Natl. Acad. Sci. USA* 96; 3029-3034 (March 1999). The sIgA antibody was made in CHO cells sequentially transfected with chimeric heavy and light chains, human J-Chain, and human secretory component, respectively. Single clones were generated to express the mIgA (clone 22), the dIgA (clone F), and the sIgA (clone 6) (p. 3031).

Still other articles proposed, for example: (1) anti-HSV mIgA made in maize (Karnoup et al. *Glycobiology* 15(10); 965-981 (May 2005)) (which states that at that time there had been little success in the application of IgA class antibodies to therapeutic use because of the difficulty in producing the dimeric form in mammalian cells at economic levels); (2) anti-*C. difficile* toxin A chimeric mouse-human monomeric and dimeric IgA made in CHO cells (Stubbe et al. *Journal of Immunology* 164; 1952-1960 (2000)); (3) anti-*N. meningitidis* chimeric IgA antibodies were produced in BHK cells cotransfected with human J-Chain and/or human secretory component (Vidarsson et al., *Journal of Immunology* 166; 6250-6256 (2001)); (4) anti-*Pseudomonas aeruginosa* O6 lipopolysaccharide chimeric mouse/human mIgA1 made in CHO cells (Preston et al. Infection and Immunity 66(9); 4137-4142 (September 1998)); (5) anti-*Plasmodium* mIgA made in CHO cells (Pleass et al. *Blood* 102(13); 4424-4429 (December 2003)) (which states that unlike their parental mouse IgG antibodies, the mIgA antibodies failed to protect against parasitic challenge in vivo); and (5) anti-*Helicobacter pylori* urease subunit A sIgA and dIgA (Berdoz et al. Molecular Immunology 41(10); 1013-1022 (August 2004)).

For a review article discussing passive and active protection against pathogens at mucosal surfaces, see Corthésy. "Recombinant Immunoglobulin A: Powerful Tools for Fundamental and Applied Research." *Trends in Biotechnology* 20(2); 65-71 (February 2002).

Still other articles propose the use of IgA antibodies as a treatment for cancer.

For example, one article describes a Phase Ia trial of a muring anti-transferrin receptor IgA antibody (Brooks et al. "Phase Ia Trial of Murine Immunoglobulin A Antitransferrin Receptor Antibody 42/6." *Clinical Cancer Research* 1(11); 1259-1265 (November 1995)). Another article describes a human anti-Ep-CAM mIgA made in BHK (baby hamster kidney) cells (Huls et al. "Antitumor Immune Effector Mechanisms Recruited by Phase Display-Derived Fully Human IgG1 and IgA1 Monoclonal Antibodies." *Cancer Research* 59; 5778-5784 (November 1999)). Still another article describes an anti-HLA Class II chimeric mIgA antibody made in BHK cells (Dechant et al. "Chimeric IgA Antibodies Against HLA Class II Effectively Trigger Lymphoma Cell Killing." *Blood* 100(13); 4574-4580 (December 2002)). Yet other articles describe anti-EGFR mIgA or dIgA antibodies made in CHO, including Dechant et al. "Effector Mechanisms of Recombinant IgA Antibodies Against Epidermal Growth Factor Receptor." *Journal of Immunology* 179; 2936-2943 (2007), Beyer et al. "Serum-Free Production and Purification of Chimeric IgA Antibodies." *Journal of Immunology* 346; 26-37 (2009) (stating that as of 2009, IgA antibodies have not been commercially explored for problems including lack of production and purification methods), and Lohse et al. "Recombinant Dimeric IgA Antibodies Against the Epidermal Growth Factor Receptor Mediate Effective Tumor Cell Killing" *Journal of Immunology* 186; 3770-3778 (February 2011).

For a review article on anti-cancer IgA antibodies, see Dechant et al. "IgA antibodies for Cancer Therapy."*Critical Reviews in Oncology/Hematology* 39; 69-77 (2001); states that compared with infectious diseases, the role of IgA in cancer immunotherapy is even less investigated).

It is desirable to have alternative antibody treatments for inflammatory diseases that preferably avoid the disadvantages of current systemic and previously-proposed topical treatments of inflammation.

SUMMARY OF THE INVENTION

The present invention relates to monoclonal secretory IgA antibodies that bind to and neutralize a human proinflammatory cytokine, or bind to and block a human receptor of a human proinflammatory cytokine, and the use of such secretory IgA antibodies in treating inflammatory diseases in humans.

An aspect of the present invention relates to a monoclonal secretory IgA antibody that binds to and neutralizes a human proinflammatory cytokine.

In embodiments, the antibody can be, for example a chimeric antibody, a humanized antibody, or a human antibody. The antibody can contain a human secretory chain and a human J-chain. The antibody can be a human secretory IgA1 antibody. The human proinflammatory cytokine can be selected from, for example, TNFα (soluble), interferon gamma, interferon alpha, GM-CSF, CXCL10/IP-10, IL-1β, IL-1α, IL-4, IL-5, IL-6, IL-12; IL-13, IL-17A, IL-18, IL-20, IL-22, and IL-23. The antibody can contain CDR sequences that are identical to the CDR sequences of an antibody selected from adalimumab, infliximab, golimumab, certolizumab pegol, ozoralizumab, sifalimumab, canakinumab, gevokizumab, pascolizumab, reslizumab, mepolizumab, sirukumab, olokizumab, ustekinumab, briakinumab, tralokinumab, anrukinzumab, lebrikizumab, secukinumab, ixekizumab, and fezakinumab.

Another aspect of the present invention relates to a composition containing a plurality of the secretory IgA antibodies. In embodiments, substantially all N-glycans in the plurality of antibodies lack fucose and xylose residues. In embodiments, the plurality of antibodies contains at least about 30% G0 glycans (preferably G0 glycans lacking Fuc and Xyl residues) relative to the total amount of N-glycans in the population. In embodiments, the a plurality of antibodies ac contains at least about 25% high-mannose glycans (e.g., Man5, Man6, Man7, Man8, and/or Man9 glycans) relative to the total amount of N-glycans in the population. In embodiments, the G0 glycans (preferably G0 glycans lacking Fuc and Xyl residues) and high-mannose glycans (e.g., Man5, Man6, Man7, Man8, and/or Man9 glycans) together are the majority of glycans present in said plurality of antibodies, such as at least 70% of the total amount of N-glycans in said plurality of antibodies.

Another aspect of the present invention relates to pharmaceutical compositions containing the secretory IgA antibodies, which can be adapted for oral administration and can be used to treat an inflammatory disease in a human.

Another aspect of the present invention relates to methods for treating an inflammatory disease in a human, which includes administering an anti-inflammatory effective amount of the secretory IgA antibodies (or compositions) to a human in need thereof, preferably orally administering the antibodies (compositions). The inflammatory disease can be selected from rheumatoid arthritis, inflammatory bowel disease (including Crohn's disease and ulcerative colitis), psoriasis, psoriatic arthritis, ankylosing spondylitis, juvenile idiopathic arthritis, uveitis, asthma, Alzheimer's disease, multiple sclerosis, type II diabetes, systemic sclerosis, lupus nephritis, and allergic rhinitis.

Another aspect of the present invention relates to a monoclonal secretory IgA antibody that binds to and blocks a human proinflammatory cytokine receptor selected from IL-1R, IL-2R, IL-4R, IL-5R, IL-6R, and IL-17R.

BRIEF DESCRIPTION OF THE SEQUENCES

SEQ ID NO:1 provides the amino acid sequence of the soluble TNF-α receptor of etanercept (extracellular part of tumor necrosis factor receptor 2: amino acids 23-257 of UniProtKB/Swiss-Prot database entry P20333 (TNR1B_HUMAN)).

SEQ ID NO:2 provides the amino acid sequence of the heavy chain variable region of infliximab (cA2).

SEQ ID NO:3 provides the amino acid sequence of the light chain variable region of infliximab (cA2).

SEQ ID NO:4 provides the amino acid sequence of the heavy chain variable region of adalimumab (D2E7).

SEQ ID NO:5 provides the amino acid sequence of the light chain variable region of adalimumab (D2E7).

SEQ ID NO:6 provides the amino acid sequence of the heavy chain variable region of golimumab.

SEQ ID NO:7 provides the amino acid sequence of the light chain variable region of golimumab.

SEQ ID NO:8 provides the amino acid sequence of the heavy chain variable region of certolizumab pegol.

SEQ ID NO:9 provides the amino acid sequence of the light chain variable region of certolizumab pegol.

SEQ ID NO:10 provides the amino acid sequence of a human IgA α-1 heavy chain constant region (Cα1-Cα2-Cα3) (UniProtKB/Swiss-Prot database entry P01876 (IGHA1_HUMAN)).

SEQ ID NO:11 provides the amino acid sequence of a human IgA α-2 m(1)-allotype heavy chain constant region (Cα1-Cα2-Cα3) (UniProtKB/Swiss-Prot database entry P01877 (IGHA2_HUMAN)).

SEQ ID NO:12 provides the amino acid sequence of a human IgA α-2 m(2)-allotype heavy chain constant region (Cα1-Cα2-Cα3). (UniProtKB/Swiss-Prot database entry P01877 (IGHA2_HUMAN) with indicated modifications for allotype 2 variant).

SEQ ID NO:13 provides the amino acid sequence of a human IgA α-2 (n)-allotype.

SEQ ID NO:14 provides the amino acid sequence of a human κ light chain constant region ($C_L$) (UniProtKB/Swiss-Prot database entry P01834 (IGKC_HUMAN)).

SEQ ID NO:15 provides the amino acid sequence of a human λ1 light chain constant region ($C_L$) (UniProtKB/Swiss-Prot database entry P0CG04 (LAC1_HUMAN)).

SEQ ID NO:16 provides the amino acid sequence of a human λ2 light chain constant region ($C_L$) (UniProtKB/Swiss-Prot database entry P0CG05 (LAC2_HUMAN)).

SEQ ID NO:17 provides the amino acid sequence of a human λ3 light chain constant region ($C_L$) (UniProtKB/Swiss-Prot database entry P0CG06 (LAC3_HUMAN)).

SEQ ID NO:18 provides the amino acid sequence of a human λ6 light chain constant region ($C_L$) (UniProtKB/Swiss-Prot database entry P0CF74 (LAC6_HUMAN)).

SEQ ID NO:19 provides the amino acid sequence of a human λ7 light chain constant region ($C_L$) (UniProtKB/Swiss-Prot database entry A0M8Q6 (LAC7_HUMAN)).

SEQ ID NO:20 provides the amino acid sequence of a human J-chain (amino acids 23-159 UniProtKB/Swiss-Prot database entry P01591).

SEQ ID NO:21 provides the amino acid sequence of a human secretory component (amino acids 19-603 of UniProtKB/Swiss-Prot database entry P01833 (PIGR_HUMAN), RCSB Protein Data Bank structure 2OCW).

SEQ ID NO:22 provides the amino acid sequence of a natural signal peptide (secretion signal) for a human J-chain (amino acids 1-22 UniProtKB/Swiss-Prot database entry P01591).

SEQ ID NO:23 provides the amino acid sequence for a signal peptide (heavy chain secretion signal).

SEQ ID NO:24 provides the amino acid sequence for a signal peptide (light chain secretion signal).

SEQ ID NO:25 provides the amino acid sequence for a signal peptide (SC-chain secretion signal).

SEQ ID NO:26 provides the amino acid sequence for a rice α-amylase signal peptide (secretion signal).

SEQ ID NO:27 provides the DNA sequence for the infliximab heavy chain IgA2m(n) optimized for maize.

SEQ ID NO:28 provides the DNA sequence for the infliximab heavy chain IgA1 and light chain κ optimized for HEK.

SEQ ID NO:29 provides the DNA sequence for the infliximab light chain optimized for maize.

SEQ ID NO:30 provides the DNA sequence for SC- and J-chains optimized for HEK.

SEQ ID NO:31 provides the DNA sequence for the adalimumab heavy chain IgA1 optimized for *Lemna*.

SEQ ID NO:32 provides the DNA sequence for the adalimumab light chain κ optimized for *Lemna*.

SEQ ID NO:33 provides the DNA sequence for a J-chain optimized for maize.

SEQ ID NO:34 provides the DNA sequence for a J-chain optimized for *Lemna*.

SEQ ID NO:35 provides the DNA sequence for an SC-chain optimized for maize.

SEQ ID NO:36 provides the DNA sequence for an SC-chain optimized for *Lemna*.

SEQ ID NO:37 provides the amino acid sequence of the heavy chain variable region of ustekinumab (CTNO-1275).

SEQ ID NO:38 provides the amino acid sequence of the light chain variable region of ustekinumab (CTNO-1275).

SEQ ID NO:39 provides the amino acid sequence of the heavy chain variable region of briakinumab (J-695, ABT-874).

SEQ ID NO:40 provides the amino acid sequence of the light chain variable region of briakinumab (J-695, ABT-874).

SEQ ID NO:41 provides a complete *lemna*-optimized UKB-SA1 heavy chain IgA1 DNA (including DNA encoding signal peptide SEQ ID NO:26).

SEQ ID NO:42 provides a complete *lemna*-optimized UKB-SA1 light chain DNA (including DNA encoding signal peptide SEQ ID NO:26).

BRIEF DESCRIPTION OF THE DRAWINGS

FIG. 1 shows the amino acid sequences of the constant regions of human IgA1 (SEQ ID NO:10), IgA2 m(1) (SEQ ID NO:11), IgA2 m(2) (SEQ ID NO:12), and IgA2(n) (SEQ ID NO:13) antibody a heavy chains;

FIGS. 2A through 2I show the amino acid sequence of various TNF-α binding regions. FIG. 2A shows the amino acid sequence of the soluble TNF-α receptor of etanercept (SEQ ID NO:1); FIG. 2B shows the amino acid sequence of the heavy chain variable region of infliximab (cA2) (SEQ ID NO:2); FIG. 2C shows the amino acid sequence of the light chain variable region of infliximab (cA2) (SEQ ID NO:3); FIG. 2D shows the amino acid sequence of the heavy chain variable region of adalimumab (D2E7) (SEQ ID NO:4); FIG. 2E shows the amino acid sequence of the light chain variable region of adalimumab (D2E7) (SEQ ID NO:5); FIG. 2F shows the amino acid sequence of the heavy chain variable region of golimumab (SEQ ID NO:6); FIG. 2G shows the amino acid sequence of the light chain variable region of golimumab (SEQ ID NO:7); FIG. 2H shows the amino acid sequence of the heavy chain variable region of certolizumab pegol (SEQ ID NO: 8); FIG. 2I shows the amino acid sequence of the light chain variable region of certolizumab pegol (SEQ ID NO:9).

FIGS. 3A and 3B show the amino acid sequences of various human antibody light chain subtypes and allotypes. FIG. 3A shows the amino acid sequence of a human κ light chain constant region ($C_L$) (UniProtKB/Swiss-Prot P01834) (SEQ ID NO:14); FIG. 3B shows the amino acid sequences of a human λ light chain constant region ($C_L$) allotypes (UniProtKB/Swiss-Prot P0CG04, P0CG05, P0CG06, P0CG74, and A0M8Q6; SEQ ID NOS:15 to 19).

FIG. 4 shows the amino acid sequence of a human J-chain (a.a. 23-159 of UniProtKB/Swiss-Prot entry P01591, SEQ ID NO:20).

FIG. 5 shows the amino acid sequence of a human secretory component (a.a. 19-603 of UniProtKB/Swiss-Prot database entry P01833 [PIGR_HUMAN], SEQ ID NO:21).

FIG. 6 shows the structure of the SIgA vector constructs of Example 1.

FIGS. 17A through 17D shows amino acid sequences of various p40 (the p40 subunit of IL12 and IL23) binding regions. FIG. 17A shows the amino acid sequence of the heavy chain variable region of the antibody ustekinumab (CTNO-1275) (SEQ ID NO:37); FIG. 17B shows the amino acid sequence of the light chain variable region of the antibody ustekinumab (CTNO-1275) (SEQ ID NO:38); FIG. 17C shows the amino acid sequence of the heavy chain variable region of the antibody briakinumab (J-695, ABT-874) (SEQ ID NO:39); FIG. 17D shows the amino acid sequence of the light chain variable region of the antibody briakinumab (J-695, ABT-874) (SEQ ID NO:40).

FIG. 20 shows the degradation of an anti-IL-12/23 SIgA according to the invention having ustekinumab variable regions and being expressed in *Lemna* compared to ustekinumab (IgG1) and to colostral secretory IgA in simulated intestinal fluid (SIF). Gel A compares the SynA01-WT antibody of the invention (UKB-SA1) and gel B compares the SynA01-GO antibody of the invention (UKB-SA1g0).

In FIG. 21A, the open circle is SynA01 (UKB-SA1); the closed circle is SynA02 (UKB-SA1g0); the diamond is colostral secretory IgA; and the square is ustekinumab.

DETAILED DESCRIPTION OF THE INVENTION

Figure 7:
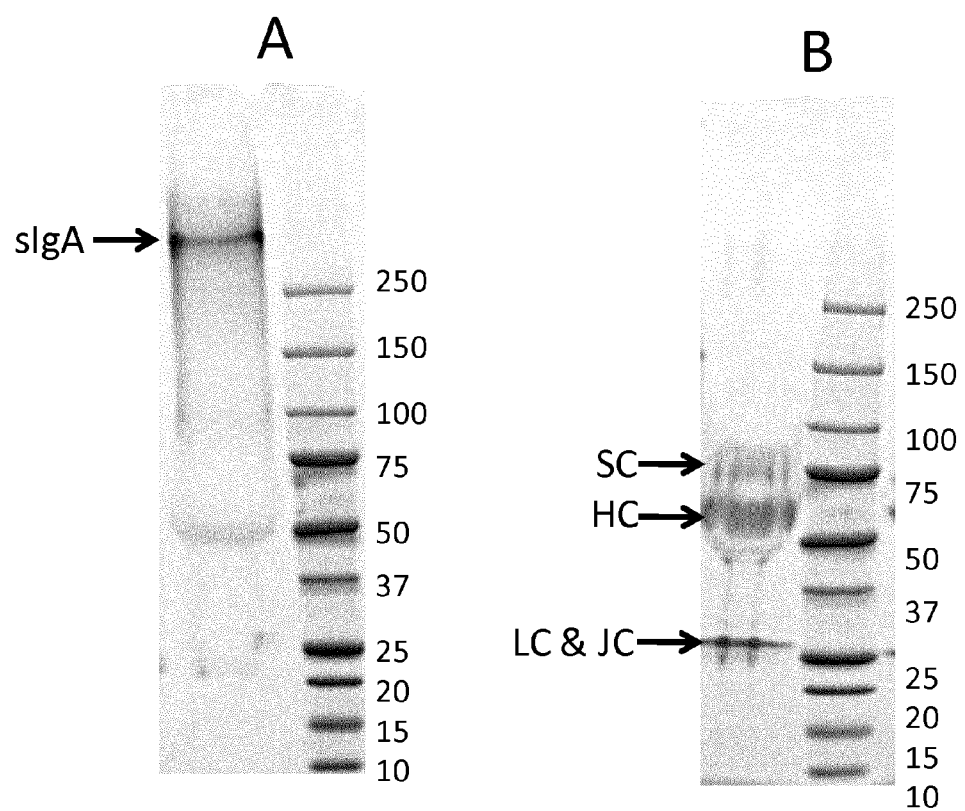
FIG. 7 shows reducing and non reducing gels of an anti-TNFα SIgA of the invention, having infliximab variable regions and being produced in mammalian HEK-293F cells. The label "A" shows non-reducing SDS-PAGE analysis demonstrating expression of complete SIgA while the label "B" shows reducing SDS-PAGE analysis.

The present invention relates to monoclonal secretory IgA antibodies that bind to and neutralize a human proinflammatory cytokine, or bind to and block a human receptor of a human proinflammatory cytokine, and the use of such secretory IgA antibodies in treating inflammatory diseases in humans.

As is well known, the basic structural unit of an antibody consists of two heavy chain proteins (heavy chains) and two light chain proteins (light chains), which are bound together by non-covalent and covalent (e.g., disulfide bonds) interactions into a single unit. The heavy and light chains have N-terminal variable regions and C-terminal constant regions. The variable regions of the light and heavy chains together form an "antigen binding region." Because the antibody has two heavy and light chains, the antibody has two antigen binding regions.

Antibodies are classified based on the heavy chain constant region, e.g., classified as IgG, IgA, IgM, IgE, IgD, etc. The light chain constant region is not used for classification. In humans, for example, all classes use one of two types of light chain constant regions, namely the Cκ (kappa) or Cλ (lambda) type. The amino acid sequences of human kappa (SEQ ID NO:14) and several lambda light chain constant regions (SEQ ID NOS:15-19) are provided in FIGS. 3A and 3B, respectively. In nature, the heavy chain constant regions of the various classes are produced by different genes: the IgA class heavy chains are uniquely encoded-for by α genes, the IgG class heavy chains by γ genes, and so forth. The heavy chain constant regions also impart the various classes with differences in their physio-chemical properties, their isotypic antigentic determinants, and/or in their biological function. Lefranc et al., *The Immunoglobulin FactsBook*, Academic Press 2001, Chapter 2, (ISBN 0-12-441351-X). The constant region of an IgA heavy chain (Cα) typically has three domains that are referred to as Cα1, Cα2, and Cα3, a short hinge section between Cα1 and Cα2, and a short tail piece at the C-terminal end of Cα3. The definition and structure of antibodies are well known to workers skilled in this art, such as described in, e.g., Alberts, B. et al., *Molecular Biology of the Cell* $3^{rd}$ *Edition*, Chapter 23, Garland Publishing Inc., New York, N.Y., 1994, and Nezlin, R., *The Immunoglobulins. Structure and Function* (1998) Academic Press (ISBN 0-12-517970-7).

The C-terminal section of two IgA antibodies, i.e., the tail pieces at the C-terminal ends of the Cα3 region, can be joined together via a J-chain to form a dimer. Dimeric IgA has four antigen binding regions; two from each IgA monomer. Typically the four antigen binding regions (and their complementarity determining regions or "CDRs") are identical for reasons such as ease of manufacture. But the antigen binding regions can, in certain circumstances, be different, e.g., different CDRs binding different epitopes on the same antigen or event different antigens (such as in the case of bispecific antibodies). Typically the CDRs of the four antigen binding regions are identical. A secretory chain, sometimes called a secretory component or SC-chain, can be attached to the dimeric IgA antibody. The SC-chain provides increased resistance to proteolysis especially in the intestinal tract. The SC-bound dimeric IgA is referred to herein as "secretory IgA" or "SIgA."

Heavy chain constant regions that qualify as an IgA-class antibody are well known in the art. Generally the amino acid sequence of the heavy chain constant regions of an IgA, regardless of how it is produced (e.g., naturally or recombinantly), corresponds to an amino acid sequence encoded for by an α-gene. In addition, IgA antibodies have characteristic antigenic determinants unique to IgA-class antibodies and different from the antigenic determinants of other classes of antibodies, such as IgG-class antibodies (see, e.g., Nezlin, R., *The Immunoglobulins. Structure and Function* (1998) Academic Press (ISBN 0-12-517970-7); Lefranc et al., *The Immunoglobulin FactsBook*, Academic Press 2001, Chapter 2, (ISBN 0-12-441351-X)). Furthermore, IgA antibodies are the only isotype that is known to specifically bind to the FcαR (see, e.g., Alberts, B. et al., *Molecular Biology of the Cell* $3^{rd}$ *Edition*, Chapter 23, Garland Publishing Inc., New York, N.Y., 1994; Lefranc et al., *The Immunoglobulin FactsBook*, Academic Press 2001, Chapter 2, (ISBN 0-12-441351-X)).

Accordingly, for purposes of the present invention, the terms "IgA antibody," "monomeric IgA," "dimeric IgA" and "SIgA" each refers to antibodies that contain the heavy chain constant regions of an IgA class of immunoglobulin, e.g., which corresponds to an amino acid sequence that can be encoded for by a genes and which react with an antibody specific for the IgA-class heavy chain. The amino acid sequence "corresponds" in that it is identical to, or contains only minor variations (insertions/deletions/substitutions) from, an amino acid sequence produced by any a gene, an individual human's IgA heavy chain sequence, or a human IgA heavy chain consensus sequence. Indeed, variations can and do exist in the amino acid sequence of the IgA heavy chain constant region without moving such antibodies outside of the IgA class. Examples of such variations can be found in various genomic databases such as browser. 1000genomes.org/index.html and ensembl.org/index.html. For clarity, because the heavy chain sequence is determinative of the Ig class, a recombinant antibody containing the IgA heavy chain constant regions and further containing the antigen binding regions encoded for by DNA sequences obtained from a known IgG antibody is still an "IgA antibody." On the other hand, a secretory IgA antibody modified to replace the Cα2 heavy chain constant domain (encoded for by the IgA-specific α-gene) with a Cγ2 heavy chain constant domain (encoded for by the IgG-specific γ-gene) is not an IgA antibody, and is instead a hybrid IgA/IgG antibody. Such a hybrid is not within the scope of the terms "monomeric IgA," "dimeric IgA" and "SIgA" antibodies, and thus is not a secretory IgA antibody according to the invention.

Minor variations of the heavy chain constant regions are permitted only to the extent that the overall antibody class, framework, and functionality of SIgA is maintained; e.g., J-chain binds to monomers and SC-chain binds to the dimeric structure and provides proteolysis resistance. Such variations include conservative substitutions. Exemplary conservative substitutions are shown in Table 1. The amino acids in the same block in the second column and preferably in the same line in the third column may, for example, be substituted for each other.

TABLE 1

| ALIPHATIC | Non-polar | G A P |
| --- | --- | --- |
| | | I L V |
| | Polar-uncharged | C S T M |
| | | N Q |
| | Polar-charged | D E |
| | | K R |
| AROMATIC | | H F W Y |

Typical minor variations of the constant regions from the normal or naturally-occurring sequence involve only conservative changes to the amino acid sequence using the recognized substitutions, insertions and/or deletions. Generally, the variations (substitutions, insertions, and/or deletions) of a constant domain of the heavy or light chain involve no more than 10 and usually no more than 5 amino acid additions, deletions, and/or substitutions (either naturally-occurring or genetically-engineered), in any Cα1, Cα2, or Cα3 domain or hinge or tail sections in comparison to a normal IgA constant domain. The sum of these minor variations in the constant domains of the SIgA antibody of the invention is usually less than 20 amino acids (acid/deletions/substitutions) and often less than 10 or less than 5.

Accordingly, at a minimum, SIgA includes any recognized amino acid sequence that is generally accepted as being within the IgA class. For example, information on the structure and function of IgA can be found in Snoeck et al., Vet. Res. 37; 455-467 (2006) and "Mucosal immune defense: Immunoglobulin A", C. S. Kaetzel ed., Springer, New York (2007) ISBN 978-0-387-72231-3. Electronic databases, such as RCSB Protein Data Bank, can also establish a known IgA sequence or portion/domain thereof. The constant domains contained in the SIgA antibodies of the invention can be human, non-human, or a combination of these. Preferred are mammalian constant regions. Most preferred are human constant regions.

In humans there are two recognized IgA subclasses: IgA1 and IgA2 which differ in the hinge section between the Cα1 and Cα2 domains of the heavy chain. In IgA1 this hinge section is relatively long and in nature typically O-glycosylated. In IgA2 the hinge section is relatively short and in nature lacks glycosylation. Both IgA1 and IgA2 SIgA antibodies are usually present in mucosal secretions. In humans, the IgA2 subclass has three known allotypes: IgA2m(1), IgA2m(2) and IgA2m(n). Unlike the subclasses, only one specific allotype will be found in a normal healthy individual. The m(1) allotype is strongly prevalent in the Caucasian population (98%) and varies between 23% and 96% for other populations. The m(2) allotype has a high prevalence in populations of African and Asian descent (50-70%). The m(n) allotype—which is considered to be a hybrid of the m(1) and m(2) allotypes—has been reported to be genetically possible, but has not been actually observed in any population. See Chintalacharuvu et al., *Journal of Immunology* 152, 5299-5304 (1994). Accordingly, SIgA antibodies of the present invention preferably contain human IgA heavy chain constant regions of the IgA1 or IgA2 sub-types, including IgA2m(1), IgA2m(2) and IgA2m(n) allotypes, and combinations thereof (e.g., one constant domain or hinge section from an IgA1 and another constant domain or hinge section from an IgA2).

Typically, the SIgA antibodies of the invention comprise the Cα1 domain, the hinge section, and the -Cα2-Cα3 domains and tail section of an IgA antibody (with or without minor variations), including a human IgA1 and/or IgA2 antibody. In this embodiment, the Cal domain, the hinge section, and the -Cα2-Cα3 domains can be of an IgA1, an IgA2m(1) allotype, an IgA2m(2) allotype, or a combination thereof. Amino acid sequences of a human IgA1 heavy chain constant region (SEQ ID NO:10), a human IgA2m(1) heavy chain constant region (SEQ ID NO:11), a human IgA2m(2) heavy chain constant region (SEQ ID NO:12), and a human IgA2(n) heavy chain constant region (corresponding to the Cα1 and Cα2 regions of an IgA2m(2) and the Cα3 region of an IgA2m(1)) (SEQ ID NO:13) are respectively shown in FIG. 1.

A modified, shortened, or removed linker/hinge section between Cα1 and Cα2 in IgA1 has been reported to increase resistance against proteases (for example see B. W. Senior et al., *J. Immunol.* 2005; 174: 7792-7799). Such can be incorporated into the SIgA antibodies of the present invention.

The J-chain is a protein that attaches to the tail piece of a monomeric IgA to join two monomeric IgAs to form a dimer. The J-chain is normally of mammalian origin, such as human, murine, rat, rabbit, sheep, cow, or goat origin, but is preferably of human origin. An example of the amino acid sequence of a human J-chain is set forth in FIG. 4 (SEQ ID NO:20). Usually, the sequence of the mammalian-derived J-chain is the same as the naturally-occurring sequence, but it can be subject to minor variations as described above for constant regions generally, e.g., up to 10 amino acid insertions, substitutions, or deletions. The minor variations do not significantly alter the function of the J-chain, and in particular the ability to join two monomeric IgA antibodies to form a dimer and to enable attachment of the SC-chain.

The secretory component, also referred to as "SC" or "SC-chain," is a protein that binds to the dimeric IgA framework and imparts increased resistance against proteolysis upon the antibody to which it is bound. Generally, the secretory component is of mammalian origin, such as human, murine, rat, rabbit, sheep, cow, or goat origin, but is preferably of human origin. The SC is the result of cleavage of the Polymeric IgA-receptor (PIGR) which usually occurs at a specific position. Some variation can occur in the position of the cleavage resulting in variant forms of SC. Usually, the sequence of the mammalian-derived SC-chain is the same as the naturally-occurring sequence, but it can be subject to minor variations as described above for constant regions generally, e.g., up to 10 amino acid insertions, substitutions, or deletions. The minor variations do not significantly alter the function of the secretory component, e.g., the ability to stabilize the SIgA against proteolysis. An example of the amino acid sequence of a human secretory component is set forth in FIG. 5 (SEQ ID NO:21).

Secretory IgA antibodies of the present invention bind to and neutralize a human proinflammatory cytokine or bind to and block a human receptor of a human proinflammatory cytokine. In a preferred embodiment, the antigen binding region of a SIgA according to the invention comprises a heavy and light chain variable region pair, each containing hypervariable regions (CDRs, which directly interact with the proinflammatory cytokine) and the supporting framework regions. The CDRs in each heavy and light chain variable region are separated from each other and from the constant domain by the framework regions, which serve to maintain the CDRs in the correct binding conformation. In general each variable part of an immunoglobulin heavy or light chain contains 3 different CDRs and four framework regions. For a more detailed description of antibody antigen binding regions, see for example C. A. Janeway et al., "*Immunobiology*" 6$^{th}$ Edition, Chapter 3, pp 110-115; Garland Science Publishing, New York, 2005 (ISBN 0815341016). Regarding framework regions in particular, see for example WO92/22653 (discussing that although framework regions do not directly interact with antigen, framework regions can influence binding of the CDRs with antigen, such as binding strength and/or downstream events).

In these embodiments, the antigen binding regions of the SIgAs of the invention bind to and neutralize the proinflammatory cytokine or bind to and block a human receptor of a human proinflammatory cytokine. Preferably, the proinflammatory cytokine or receptor is selected from TNF-alpha (preferably soluble TNF-alpha), IFN-gamma, IFN-alpha, GM-CSF, CXCL10/IP-10, IL-1-beta, IL-1-alpha, IL-4, IL-5, IL-6, IL-12, IL-13, IL-17A, IL-18, IL-20, IL-22, IL-23, IL-1 receptor, IL-2 receptor, IL-4 receptor, IL-5 receptor, IL-6 receptor, and IL-17 receptor. In embodiments, the proinflammatory cytokine is selected from IFN-gamma, IFN-alpha, GM-CSF, CXCL10/IP-10, IL-1-beta, IL-1-alpha, IL-4, IL-5, IL-6, IL-13, IL-17A, IL-18, IL-20, and IL-22.

Secretory IgA antibodies of the present invention specifically and preferentially bind with high affinity to a corresponding human proinflammatory cytokine or human receptor of a human proinflammatory cytokine. A variety of protocols for performing binding, competitive binding, or immuno-radiometric assays to determine the specific binding capability of an antibody are well known in the art (see for example Maddox et al, *J. Exp. Med.* 158, 1211-1226, 1993). Such immunoassays typically involve the formation of complexes between the specific protein and its antibody and the measurement of complex formation (e.g., binding to or unbinding from the specific protein). Generally, the affinity of secretory IgA antibodies of the invention is at least two-fold, at least 10-fold, at least 50-fold, at least 100-fold, or at least 1000-fold or greater than the affinity of the antibodies for a non-specific protein such as, for instance, BSA or casein. Typically the secretory IgA antibodies of the present invention exhibit a binding affinity constant ($K_D$) with respect to the proinflammatory cytokine or proinflammatory cytokine receptor of $10^{-7}$ M or lower, preferably $10^{-8}$ M, $10^{-9}$ M, $10^{+10}$ M, $10^{-11}$ M or $10^{-12}$M or lower.

In embodiments, secretory IgA antibodies of the present invention neutralize a proinflammatory cytokine to which it is bound. For the present invention, the term "neutralizes" means inhibits/reduces the effect of the cytokine to some degree, such as by at least 30%, at least 35%, at least 40%, and at least 45%. Typically the inhibition/reduction in the effect of the cytokine at least 50%. In these embodiments, the secretory IgA antibodies of the present invention preferably inhibit/reduce the proinflammatory effect of a cytokine to which it is bound by at least 50%, such as by at least 55%, at least 60%, at least 65%, and at least 70%, and more preferably by at least 75%, at least 80%, at least 85%, at least 90%, at least 95%, and at least 98%.

In embodiments, SIgA antibodies of the present invention blocks a proinflammatory cytokine receptor to which it is bound. For the present invention, the term "blocks" means inhibits/reduces the effect of the receptor to some degree, such as by at least 30%, at least 35%, at least 40%, and at least 45%. Typically the inhibition/reduction in the effect of the receptor at least 50%. In these embodiments, the secretory IgA antibodies of the present invention preferably inhibit/reduce the proinflammatory effect of a receptor to which it is bound by at least 50%, such as by at least 55%, at least 60%, at least 65%, and at least 70%, and more preferably by at least 75%, at least 80%, at least 85%, at least 90%, at least 95%, and at least 98%.

The amino acid sequence of the antigen binding region, and in particular the CDRs thereof, is determined by the epitope to which it binds. The amino acid sequence of the antigen binding region can be novel or can be obtained from existing anti-proinflammatory-cytokine antibodies. Methods for obtaining novel antigen binding sequences are well known in the art. See for example Mary A. Ritter and Heather M. Ladyman (Eds.) "*Monoclonal antibodies: production, engineering, and clinical application*", Cambridge University Press (1995), ISBN 0521425034, Zhiqiang An "*Therapeutic Monoclonal Antibodies: From Bench to Clinic*" Wiley, New York (2009), ISBN: 0470117915, and Christopher Dean and Philip Shepherd (Ed.) "*Monoclonal Antibodies: A Practical Approach*" Oxford University Press, USA (2000), ISBN 0199637229.

There are many therapeutic antibodies in clinical trials or on the market that function to neutralize proinflammatory cytokines, or to block proinflammatory cytokines receptors, to treat various inflammatory diseases, and the antigen binding regions (and CDRS thereof) of these known antibodies are suitable for use in the sectretory IgA antibodies of the present invention. Examples of such known antibodies, along with the neutralized cytokines and inflammatory diseases treated, are summarized in the following Table 2. See, for example, *Nature Reviews*, vol. 10, pp. 301-316 (2010); *Nature Medicine*, vol. 18, pp. 736-749 (2012); *Nature Biotechnology*, vol. 30, pp. 475-477 (2012); *Anti-Inflammatory & Anti-Allergy Agents in Medicinal Chemistry*, vol. 8, pp. 51-71 (2009); F1000.com/Reports/Biology/content/1/70, *F1000 Biology Reports*, 1:70 (2009); landesbioscience.com/journals/mabs/ReichertMABS4-1.pdf, *mAbs* 4:1, pp. 1-3 (2012); landesbioscience.com/journals/mabs/article/13895/, *mAbs* 3:1, pp. 76-99 (2011); clinicaltrials.gov (generally), and clinicaltrialsregister.eu/ (generally).

TABLE 2

| Proinflammatory Cytokine Target | Antibody | Inflammatory Disease |
| --- | --- | --- |
| TNF-alpha | adalimumab (Humira; Abbott); infliximab (Remicade; Janssen); golimumab (Simponi; Centocor); certolizumab pegol (Cimzia; UCB); ozoralizumab (Pfizer); ATN-192 (PF-05230905; Pfizer); ART621 (Arana). | Rheumatoid arthritis (RA); inflammatory bowel disease (IBD, which includes Crohn's disease and ulcerative colitis); psoriasis; psoriatic arthritis; ankylosing spondylitis; juvenile idiopathic arthritis (JIA); uveitis; (eosinophilic allergic) asthma; and/or Alzheimer's disease. |
| IFN-gamma | AMG 811 (Amgen). | Psoriasis. |
| IFN-alpha | sifalimumab (MedImmune). | Psoriasis. |
| GM-CSF | MOR103 (MorphoSys AG). | RA; multiple sclerosis (MS). |
| CXCL10/IP-10 | MDX-1100 (Medarex). | RA; IBD. |
| IL-1-beta | Canakinumab (Ilaris; Novartis); rilonacept (Arcalyst; Regeneron); gevokizumab; (XOMA). | RA; JIA; type II diabetes; uveitis; systemic sclerosis (scleroderma). |
| IL-1-alpha | TrueHuman RA-18C3 (XBiotech). | Psoriasis. |
| IL-4 | pascolizumab (PDL). | (Eosinophilic allergic) asthma. |
| IL-5 | reslizumab (Cephalon); mepolizumab (GSK); SCH55700 (Celltech). | (Eosinophilic allergic) asthma. |
| IL-6 | sirukumab (Centocor); olokizumab (UCB); PF-04236921 (Pfizer); C326 (Avidia). | RA; IBD; lupus nephritis. |
| IL-12/23 (p40) | ustekinumab (Stelara; Janssen); briakinumab (Abbott). | IBD; psoriasis; psoriatic arthritis; ankylosing spondylitis; MS. |
| IL-13 | QAX576 (Novartis); tralokinumab (MedImmune); anrukinzumab (Pfizer); lebrikizumab (Genentech); IMA-026 (Pfizer). | IBD; (eosinophilic allergic) asthma; allergic rhinitis. |
| IL-17A | secukinumab (Novartis); ixekizumab (Eli Lilly). | RA; IBS; psoriasis; psoriatic arthritis; ankylosing spondylitis; uveitis; MS; (eosinophilic allergic) asthma. |
| IL-18 | GSK1070806 (GSK). | IBD; type II diabetes. |
| IL-20 | NN8226 (Novo Nordisk). | RA; psoriasis. |
| IL-22 | fezakinumab (Pfizer). | RA; psoriasis. |
| IL-23 (p19) | MK-3222 (Merck); CNTO-1959 (Centocor); AMG-139 (Amgen). | Psoriasis; IBD. |
| IL-1 receptor | GSK1827771 (GSK); AMG-108 (Amgen). | RA. |
| IL-2 receptor | daclizumab (Zenapax; Roche); basiliximab (Simulect; Novartis). | IBD; psoriasis; JIA; uveitis; MS; (eosinophilic allergic) asthma. |
| IL-4 receptor | AMG-317 (Amgen). | (Eosinophilic allergic) asthma. |
| IL-5 receptor | benralizumab (MedImmune). | (Eosinophilic allergic) asthma. |
| IL-6 receptor | tocilizumab (Actemra; Roche); ALX-0061 (Ablynx); sarilumab (Regeneron). | RA; ankylosing spondylitis; JIA. |
| IL-17 receptor | brodalumab (Amgen). | RA; IBD; psoriasis; (eosinophilic allergic) asthma; psoriatic arthritis. |

In embodiments, a secretory IgA antibody according to the invention comprises CDR sequences that are identical to the CDR sequences of an antibody selected from adalimumab, infliximab, golimumab, certolizumab pegol, ozoralizumab, sifalimumab, canakinumab, gevokizumab, pascolizumab, reslizumab, mepolizumab, sirukumab, olokizumab, ustekinumab, briakinumab, tralokinumab, anrukinzumab, lebrikizumab, secukinumab, ixekizumab, and fezakinumab.

The CDR sequences for these antibodies are publicly available. For example, for adalimumab see WO8907452, for infliximab see CAS Registry No. 170277-31-3 (entered STN 17 Nov. 1995), for golimumab see CAS Registry No. 476181-74-5 (entered STN 13 Dec. 2002) and WO2007028106, for certolizumab pegol see CAS Registry No. 428863-50-7 (entered STN 12 Jun. 2002), for ozoralizumab see CAS Registry No. 1167985-17-2 (entered STN 24 Jul. 2009), for sifalimumab see CAS Registry No. 1006877-43-3 (entered STN 6 Mar. 2008) and WO2012162367, for canakinumab see CAS Registry No. 914613-48-2 (entered STN 4 Dec. 2006) and EP1313769, for gevokizumab see CAS Registry No. 1129435-60-4 (entered STN 30 Mar. 2009) and WO2009086003, for pascolizumab see CAS Registry No. 331243-22-2 (entered STN 13 Apr. 2001), for reslizumab see CAS Registry No. 241473-69-8 (entered STN 25 Sep. 1999) and U.S. Pat. No. 6,451,982, for mepolizumab see CAS Registry No. 196078-29-2 (entered STN 24 Oct. 1997), for sirukumab see CAS Registry No. 1194585-53-9 (entered STN 1 Dec. 2009), for olokizumab see CAS Registry No. 1007223-17-7 (entered STN 10 Mar. 2008), for ustekinumab see CAS Registry No. 815610-63-0 (entered STN 18 Jan. 2005) and EP1309692, for briakinumab see CAS Registry No. 339308-60-0 (entered STN 4 Jun. 2001), for tralokinumab see CAS Registry No. 1044515-88-9 (entered STN 29 Aug. 2008) and WO2005007699, for anrukinzumab see CAS Registry No. 910649-32-0 (entered STN 18 Oct. 2006), for lebrikizumab see CAS Registry No. 953400-68-5 (entered STN14 Nov. 2007), for secukinumab see EP1776142, for ixekizumab see CAS Registry No. 1143503-69-8 (entered STN 7 May 2009), and for fezakinumab see CAS Registry No. 1007106-86-6 (entered STN 7 Mar. 2008). Of course, these are not necessarily the only source for the CDR sequences, e.g., some CDR sequences can be obtained from other patent and non-patent literature, and commercially-available antibodies can be purchased and sequenced.

For example, a secretory IgA antibody according to the invention can comprise CDR sequences that are identical to the CDR sequences of an antibody selected from golimumab, certolizumab pegol, ozoralizumab, sifalimumab, canakinumab, gevokizumab, pascolizumab, reslizumab, mepolizumab, sirukumab, olokizumab, briakinumab, tralokinumab, anrukinzumab, lebrikizumab, secukinumab, ixekizumab, and fezakinumab. As another example, a secretory IgA antibody according to the invention can comprise CDR sequences that are identical to the CDR sequences of an antibody selected from ozoralizumab, sifalimumab, canakinumab, gevokizumab, pascolizumab, reslizumab, mepolizumab, sirukumab, olokizumab, tralokinumab, anrukinzumab, lebrikizumab, secukinumab, ixekizumab, and fezakinumab.

In embodiments a secretory IgA antibody according to the invention comprises CDR sequences that are identical to the CDR sequences of an antibody selected from daclizumab, basiliximab, benralizumab, tocilizumab, sarilumab, brodalumab, and omalizumab. The CDR sequences for these antibodies are publicly available. For example, for daclizumab see CAS Registry No. 152923-56-3 (entered STN 10 Feb. 1994) and EP932415, for basiliximab see CAS Registry No. 179045-86-4 (entered STN 1 Aug. 1996) and EP0449769, for benralizumab see CAS Registry No. 1044511-01-4 (entered STN 29 Aug. 2008), for tocilizumab see CAS Registry No. 375823-41-9 (entered STN 17 Dec. 2001) and EP0783893, for sarilumab see CAS Registry No. 1189541-98-7 (entered STN 22 Oct. 2009), for brodalumab see CAS Registry No. 1174395-19-7 (entered STN 17 Aug. 2009), and for omalizumab see CAS Registry No. 242138-07-4 (entered STN 28 Sep. 1999) and EP0602126. Of course, these are not necessarily the only source for the CDR sequences, e.g., some CDR sequences can be obtained from other patent and non-patent literature, and commercially-available antibodies can be purchased and sequenced.

In still other embodiments, antigen binding regions of secretory IgA antibodies of the invention are obtained from other and/or novel anti-proinflammatory cytokine (or anti-proinflammatory cytokine receptor) antibodies. Methods for obtaining antibodies against specific antigens are well known in the art and can be used to obtain suitable inflammatory cytokine-binding variable regions. See for example Mary A. Ritter and Heather M. Ladyman (Eds.) "*Monoclonal antibodies: production, engineering, and clinical application*", Cambridge University Press (1995), ISBN 0521425034, Zhiqiang An "*Therapeutic Monoclonal Antibodies: From Bench to Clinic*" Wiley, New York (2009), ISBN: 0470117915, and Christopher Dean and Philip Shepherd (Ed.) "*Monoclonal Antibodies: A Practical Approach*" Oxford University Press, USA (2000), ISBN 0199637229.

Secretory IgA antibodies of the invention can be non-human antibodies, chimeric antibodies, humanized antibodies, human antibodies, or other mixes of human and non-human sequences/regions. See, e.g., Yamashita et al. *Cytotechnology* 55: 55-60 (2007). A chimeric antibody is an antibody having an antigen binding region (CDRs and framework) originating from a first species (typically a mouse) and heavy chain constant regions originating from a second species (typically a human). A humanized antibody is a human antibody onto which non-human (typically murine) CDRs have been grafted. In the humanized antibody, certain human supporting framework amino acid residues can be replaced with their counterparts from the non-human parent antibody. Such an antibody containing certain non-human framework residues is still a humanized antibody. See, e.g., WO92/22653. In the humanized antibodies, the sequence of the supporting framework into which the non-human CDRs are grafted can be obtained from any human isotype/class, preferentially from IgG or IgA, and may be modified to improve the properties thereof (e.g., antigen binding and/or downstream effects). A human antibody is fully-human, containing only human constant and variable regions, i.e., having only human heavy and light chains (derivable from human genomic sequences by naturally-occurring recombination and mutation processes, consensus sequences, etc.). Likewise, a non-human antibody contains only non-human constant and variable regions, i.e., having only non-human heavy and light chains.

The secretory IgA antibodies of the invention may contain additional atoms, moieties, molecules, and/or modifications beyond the dimeric IgA, J-chain, and SC-chain. For example, the secretory IgA antibodies of the invention may be PEGylated or glycosylated (or aglycosylated) in various orientations and/or amounts. The location, attachment, amount, and structure of attached glycans found in naturally occurring antibodies shows substantial variability and mainly depends on the source of the glycoprotein (i.e., the type of cell producing the glycoprotein), but is also influenced by growing conditions (i.e., feed and environmental conditions). The secretory IgA antibodies of the present invention are not limited to any specific form of glycosylation and specifically include non-glycosylated proteins, partially or fully deglycosylated proteins, variants obtained by genetic or other manipulation of the glycosylation system of the producing cell, and variants with chemically or enzymatically modified glycans. The secretory IgA antibodies of the invention can be glycoproteins with glycosylation patterns native to plant, mammalian (human), or insect cells. Additionally the antibodies of the invention may be conjugated with (fluorescent) markers or therapeutic agents, etc. (see, e.g., Lash, A. "Making the case for antibody-drug conjugates;" In Vivo: The Business & Medicine Report; vol. 28, No. 11, pp. 32-39 (December 2010) Elsevier Business Intelligence).

It is recognized that antibodies having more than one glycosylation site can have the same glycan species attached to each glycosylation site, or can have different glycan species attached to different glycosylation sites. In this manner, different patterns of glycan attachment yield different glycoforms of a glycoprotein. Monomeric IgA1 antibodies have two conserved N-glycosylation sites (per chain): one on the CH2 region and one on the tailpiece. Monomeric IgA2 antibodies have an additional two or three N-glycosylation sites (per chain). Furthermore, the J-chain of dimeric IgA has one conserved N-glycosylation site, and the secretory component of secretory IgA has 7 conserved N-glycosylation sites.

The terms "N-glycan(s)" and "N-linked glycan(s)" are used interchangeably and refer to an N-linked oligosaccharide, e.g., one that is or was attached by an N-acetylglucosamine (GlcNAc) residue linked to the amide nitrogen of an asparagine residue in a protein. The predominant sugars found on glycoproteins are glucose (Glu), galactose (Gal), mannose (Man), fucose (Fuc), N-acetylgalactosamine (GalNAc), N-acetylglucosamine (GlcNAc), and sialic acid (e.g., N-acetyl-neuraminic acid (NeuAc)). The processing of the sugar groups occurs co-translationally in the lumen of the ER and continues in the Golgi apparatus for N-linked glycoproteins.

For the purposes of the present invention, the term "G2 glycan," "G2 glycan species," and "G2 glycan structure" are used interchangeably and refer to an N-linked glycan having the GlcNAc2Man3GlcNAc2Gal2 structure, in which two terminal galactose (Gal) sugar residues are present. For the purposes of the present invention, the term "G1 glycan," "G1 glycan species," and "G1 glycan structure" are used interchangeably and refer to an N-linked glycan having the GlcNAc2Man3GlcNAc2Gal structure, in which only one terminal galactose (Gal) sugar residue is present. For the purposes of the present invention, the term "G0 glycan," "G0 glycan species," and "G0 glycan structure" are used interchangeably and refer to an N-linked glycan having the GlcNAc2Man3GlcNAc2 structure, in which no terminal galactose (Gal) sugar residues are present.

For the purposes of the present invention, the term "high-mannose glycan," high-mannose glycan species," and "high-mannose glycan structure" are used interchangeably and refer to an N-linked glycan having the GlcNAc2ManX structure, wherein X is a whole number greater than three, such as 5, 6, 7, 8, or 9. For the purposes of the present invention, the term "Man5 glycan," Man5 glycan species," and "Man5 glycan structure" are used interchangeably and refer to an N-linked glycan having the GlcNAc2Man5 structure. The same is applicable for the terms Man6 glycan (species; glycan structure), Man7 glycan (species; glycan structure), Man8 glycan (species; glycan structure), Man 9 glycan (species; glycan structure), etc.

In mammals, naturally-occurring N-glycans contain a fucose (Fuc) residue attached to the GlcNAc2Man3 core structure by an α1,6 linkage. In plants, naturally-occurring N-glycans contain a fucose (Fuc) residue attached to the GlcNAc2Man3 core structure by an α1,3 linkage and further contain a xylose (Xyl) residue attached to the GlcNAc2Man3 core structure by a β1,2 linkage. For the purposes of the present invention, a G0 glycan containing the mammalian α1,6-linked Fuc residue attached to the GlcNAc2Man3 core structure is referred to as a "G0F<6> glycan." For the purposes of the present invention, a G0 glycan containing the plant α1,3-linked Fuc residue attached to the GlcNAc2Man3 core structure is referred to as a "G0F<3> glycan," a G0 glycan containing the plant β1,2-linked Xyl residue attached to the GlcNAc2Man3 core structure is referred to herein as a "G0X glycan," and a G0 glycan containing each of the plant α1,3-linked Fuc residue and the plant β1,2-linked Xyl residue attached to the GlcNAc2Man3 core structure is referred to herein as a "G0XF<3> glycan." In an embodiment, the invention relates to a secretory IgA antibody, or a population of secretory IgA antibodies, in which substantially all N-glycans lack Fuc and Xyl residues.

The present invention also relates to a composition comprising a plurality of secretory IgA antibodies containing multiple N-glycans, such as two or more different N-glycans. In embodiments, the plurality of secretory IgA antibodies contains at least about 30% G0 glycans (preferably G0 glycans lacking Fuc and Xyl residues) relative to the total amount of N-glycans in the population. In embodiments, the plurality of secretory IgA antibodies contains at least about 25% high-mannose glycans (e.g., Man5, Man6, Man7, Man8, and/or Man9 glycans) relative to the total amount of N-glycans in the population. In embodiments, G0 glycans (preferably G0 glycans lacking Fuc and Xyl residues) and high-mannose glycans (e.g., Man5, Man6, Man7, Man8, and/or Man9 glycans) together are the majority of glycans present in the plurality of secretory IgA antibodies, such as at least 70% relative to the total amount of N-glycans in the plurality of secretory IgA antibodies.

The glycoform of an antibody, and the nature of glycan species, can be determined by measuring the glycosylation profile thereof. The term "glycosylation profile" means the characteristic fingerprint of the representative N-glycan species that have been released from an antibody, either enzymatically or chemically, and then analyzed for their carbohydrate structure, for example, using LC-HPLC, or MALDI-TOF MS, and the like. See, for example, the review in *Current Analytical Chemistry*, Vol. 1, No. 1 (2005), pp. 28-57." For more information on glycosylation of therapeutic antibodies, see, e.g., Fernandes et al., *Eur. Biopharm. Rev.*, Summer 2005, pp. 106-110; Jefferis, *Nature Reviews/Drug Discovery*, vol. 8, March 2009, pp. 226-234.

The SIgA antibodies of the present invention are preferably monoclonal antibodies. A "monoclonal antibody" refers to a population or collection of antibodies that are substantially identical because they were all produced by clones of a single cell. For the present invention, a monoclonal SIgA is a SIgA containing monoclonal monomeric IgA antibodies. Preferably, a monoclonal SIgA contains monomeric IgA antibodies, a J-Chain, and an SC-chain that were all produced by a clone of a single cell.

The antibodies of the present invention are often isolated or in an isolated form. As used herein, the terms "isolate," "isolating" and "isolation" refer to separating the antibody from its production environment. The extent of separation is generally at least 50%, but is frequently at least 70%, 80%, 90%, 95%, 98%, 99%, 99.5%, or 99.9% (w/w). When the SIgA antibody of the present invention is produced in a cell, which is the typical process, the separation refers to separating the antibody from the host cells and native host cell proteins. Isolation is thus related to purification. Preferably the antibody of the present invention in isolated form has removed, or been separated from, at least 90%, more typically at least 99% (w/w) of the host cell proteins of the original composition.

Various compositions that contain the secretory IgA antibodies of the present invention, whether in an isolated form or not, are also contemplated as being part of the present invention. For instance, compositions that contain low amounts of incomplete secretory IgA antibodies are often desirable. With respect to the amount of secretory IgA antibodies in the composition, the amount of dimer IgA (no SC-chain) is desirably less than 50%, more desirably less than 25% and often less than 10%. Thus in a composition that contained 10 mg of secretory IgA, the amount of non-SC-chain dimeric IgA would preferably be less than 1 mg, i.e., less than 10%. The same is true for monomeric IgA: the content of IgA monomers is desirably less than 50% the amount of secretory IgA, more desirably less than 25% and often less than 10%. In some embodiments, the combined amount of dimer IgA (i.e., no SC-chain) and monomer IgA is less than 25% of the amount of secretory IgA in the composition, often less than 10%, and even less than 5%. The above amounts apply to both isolated and non-isolated forms of secretory IgA compositions. Accordingly, the low relative amounts of incomplete secretory IgA can be a result of the expression system (native low-production of incomplete secretory IgA), the result of some separation or purification that removes incomplete secretory IgA antibodies, or both.

Purified secretory IgA compositions are also useful. A purified secretory IgA (composition) contains a secretory IgA antibody of the present invention in an amount of at least 85%, often at least 90%, more often at least 95%, and preferably at least 97%, 98%, or 99%, based on the total soluble protein content. The purified composition can be a solid, such as a lyophilized product, or a liquid. A typical liquid form contains no solids, e.g., no insoluble cell wall materials, and is often based on water as the main or sole solvent and optionally containing salts, pH adjusting agents, or buffers. A purified liquid composition generally contains the secretory IgA antibody of the invention in a concentration of 50 µg/ml or more, often at least 100 µg/ml, preferably at least 1 mg/ml.

Production of Proteins of the Present Invention

The SIgA antibodies of the invention can be produced using recombinant techniques. Although several expression systems are known, including CHO, HEK, yeast, tobacco, etc., the use of duckweed as the host cell has been found to be advantageous for the production of SIgAs. Other plant host cells, namely tobacco and lettuce, tend to give very low expression rates of the desired SIgA and typically render impractical a measurable recovery of the antibody. Similarly, CHO cells also tend to give low results. HEK generally have higher titers than CHO cells, but have certain production and regulatory disadvantages. Accordingly, duckweed is, surprisingly, a convenient host cell for expressing secretory IgAs of the present invention.

Generally, a genetically modified duckweed is a known expression system for producing various proteins (see U.S. Pat. No. 6,040,498), including for the production of monoclonal antibodies (see U.S. Pat. No. 7,632,983). Duckweed is the common name for the members of the monocotyledonous family Lemnaceae. The five known genera and 38 species of Lemnaceae are all small, free-floating, freshwater plants whose geographical range spans the entire globe: genus *Lemna* (*L. aequinoctialis*, *L. disperma*, *L. ecuadoriensis*, *L. gibba*, *L. japonica*, *L. minor*, *L. minuscula*, *L. obscura*, *L. perpusilla*, *L. tenera*, *L. trisulca*, *L. turionifera*, *L. valdiviana*); genus *Spirodela* (*S. intermedia*, *S. polyrrhiza*); genus *Wolffia* (*Wa. angusta*, *Wa. arrhiza*, *Wa. australina*, *Wa. borealis*, *Wa. brasiliensis*, *Wa. columbiana*, *Wa. elongata*, *Wa. globosa*, *Wa. microscopica*, *Wa. neglecta*) genus *Wolfiella* (*Wl. caudata*, *Wl. denticulata*, *Wl. gladiata*, *Wl. hyalina*, *Wl. lingulata*, *Wl. repunda*, *Wl. rotunda*, and *Wl. neotropica*), and genus *Landoltia* (*L. punctata*). For clarity, the term "duckweed" as used in the present invention includes the foregoing species, genetically modified variants thereof (e.g., modified to control glycosylation, secretion, etc.), and any other genera or species of Lemnaceae, if they exist, optionally in a genetically modified form. Typically the genus *Lemna* is preferred, especially the species *L. minor* and *L. gibba* in natural or genetically modified forms. Also, the use of the term "duckweed," or any genus or species thereof, is meant to include individual plant cell(s), nodules, as well as whole plants including mature plants having root and fronds, unless otherwise indicated by context or express statement.

Recombinant production of sIgAs in duckweed requires transformation of duckweed, either transiently or stably. For production purposes, a stable transformation, wherein the nucleic acid sequences and/or genes needed to produce the desired SIgA have been operably introduced into the genome of a duckweed, is typically preferred. Stable transgenesis in duckweed can be obtained by different techniques as described in U.S. Pat. Nos. 6,040,498 and 7,161,064 to Stomp et al. Briefly stable duckweed transgenesis can be achieved by DNA-coated particle bombardment, electroporation, and *Agrobacterium* spp.-mediated transformation. Preferably, transgenesis of duckweed is performed by using *A. tumefaciens*-mediated transformation. Briefly, *Agrobacterium*-mediated transformation is carried out by dedifferentiating fully grown duckweed plants or tissues, preferably tissues of meristematic origin, into calli. Callus induction is carried out by growing duckweed in medium containing plant growth regulators and supplements. Calli can/will re-differentiate into organized nodules. Both nodules or calli can be infected with *Agrobacterium*, according to the procedure described in U.S. Pat. Nos. 6,040,498 and 7,161,064 to Stomp et al. Regeneration of plants from infected calli/nodules and concomitant selection for transformants by applying the desired selective pressure results in the isolation of transgenic duckweed lines carrying the exogenous DNA of interest.

Construct for expression of SIgAs, to be used for transformation of duckweed, can be produced by using standard techniques for example, the techniques described in Sambrook & Russell, Molecular Cloning: A Laboratory Manual, 3rd Edition, Cold Spring Harbor Laboratory, NY (2001) and Ausubel et al, Current Protocols in Molecular Biology (Greene Publishing Associates and Wiley Interscience, NY (1989)). Vectors for transformation of duckweed have been described elsewhere, such as in U.S. Pat. Nos. 6,040,498 and 7,161,064 to Stomp et al. Preferably, an *A. tumefaciens* binary vector (generated, for example, by standard cloning in *E. coli*) is used to first transform *A. tumefaciens*; the transgenic line obtained can then be employed to transform duckweed. Preferably, such vectors contain multiple resistance genes, to allow for selection in bacteria and in duckweed. Genes for bacterial selection are known in the art. Suitable resistance genes for selection in plants have been described in U.S. Pat. Nos. 6,040,498 and 7,161,064 to Stomp et al., and include gentamycin and kanamycin.

For expression of SIgAs, multiple transformations can be performed with separate vectors including different cassette coding for the J-chain, the SC-chain, the antibody H chain and L chain. In a preferred embodiment, a single vector is used for transformation that contains 4 cassettes each encoding for one of the structural subunit of the SiGA (namely, H chain, L chain, SC-chain and J-chain). Construction of vectors containing multiple expression cassette for antibody expression have been described in U.S. Pat. No. 7,632,983 to Dickey et al.

In one embodiment, expression of the cassettes is driven by individual promoters. Examples of suitable promoter can be found in U.S. Pat. No. 4,771,002 to Stanton, U.S. Pat. No. 5,428,147 to Barker et al., U.S. Pat. No. 7,622,573 & U.S. Pat. No. 8,034,916 to Dickey et al., disclosures of which are incorporated herein by references. Most preferably, four different promoters are used for each expression cassette (such as the chimeric *A. tumefaciens* octopine and mannopine synthase promoter, the *L. minor* polyubiquitin promoter (LmUbq), *Lemna aequinoctialis* polyubiquitin promoter (LaUbq) and *Spirodela polyrrhiza* polyubiquitin promoter (SpUbq). In a preferred embodiment, the expression vector includes cassettes coding for all 4 of the SIgA components, i.e. J-chain, SC-chain, H-chain and L-chain. In even more preferred embodiment, each of the 4 cassettes is driven by a different promoter. In a different embodiment, the constructs are driven by, heat shock gene promoters, cold-induced promoters, drought-inducible gene promoters, pathogen-inducible gene promoters, wound-inducible gene promoters, and light/dark-inducible gene promoters, promoters from genes induced by abscissic acid, auxins, cytokinins, and gibberellic acid, as described in U.S. Pat. No. 7,632,983 to Dickey et al.

In an advantageous embodiment, the vectors used for expression include, 5' of the coding sequence of the expression cassette, a signal peptide sequence placed in frame with the N-terminal portion of the protein of interest. Such signal peptide sequence interacts with a receptor protein on the membrane of the endoplasmic reticulum (ER) to direct the translocation of the growing polypeptide chain across the membrane and into the endoplasmic reticulum for secretion from the cell. Presence of the signal peptide sequence ensures efficient secretion into the extracellular space. This signal peptide is generally cleaved from the precursor polypeptide to produce a mature polypeptide lacking the signal peptide. Suitable signal peptide include the *Arabidopsis thaliana* chitinase signal peptide, the *Oryza sativa* α-amylase signal peptide, or any other suitable duckweed signal peptide sequences, as described in U.S. Pat. No. 7,632,983 to Dickey et al. In a most preferred embodiment, the sequence of the signal peptide used in the *O. sativa* α-amylase signal peptide. In some embodiments of the present invention, the secreted SIgAs are retained within the apoplast, the region between the plasma membrane and the cell wall. In other embodiments, the polypeptide diffuses across the cell wall of the plant host cell into the external environment/media.

Other suitable nucleotide sequences including enhancers, 5' leader sequences, such as the leader sequence of *L. gibba* ribulose-bis-phosphate carboxylase small subunit 5B gene, 3' UTR sequences, introns, enhancers, "ACC" and "ACA" trinucleotides to be introduced directly upstream of the translation initiation codon of the nucleotide sequence of interest can be used to improve expression as disclosed in the art and in U.S. Pat. Nos. 6,040,498 and 7,161,064 to Stomp et al as well as U.S. Pat. No. 7,622,573 & U.S. Pat. Nos. 8,034,916 7,632,983 to Dickey et al, disclosures of which are all incorporated by reference herein.

For example, the expression from the transgenic lines obtained can be improved by optimizing the codon distribution of the encoded proteins for expression in duckweed. Duckweed-preferred codons, as used herein, refers to codons that have a frequency of codon usage in duckweed of greater than 17%. Likewise the codons can be optimized for expression in *L. minor* or *L. gibba*. In each case the codons have a frequency of codon usage of greater than 17%. Duckweed and *Lemna* ssp. codon optimization is known in the art and is carried out, e.g. as described in U.S. Pat. No. 7,632,983 to Dickey et al.

Another option is to modify the glycosylation profile of the duckweed. The stably transformed duckweed can also contain a genetic modification that alters the glycan profiles. For example, the N-glycans of the SIgA can be expressed with reduced levels of fucose and xylose residue, preferably less than 10%, more preferably less than 1%. This modification from natural glycan profile can be achieved by several techniques, including knocking out endogenous α1,3-fucosyltransferase (FucT) and β1,2-xylosyltransferase (XylT), or otherwise inhibiting their transcription of the gene/expression or enzymatic activity. In a preferred embodiment, the duckweed is transformed with at least one recombinant nucleotide construct that provides for the inhibition of expression of α1,3-fucosyltransferase (FucT) and β1,2-xylosyltransferase (XylT) in a plant. In a more preferred embodiment, these constructs triggers RNA interference targeting the mRNAs of α1,3-fucosyltransferase (FucT) and β1,2-xylosyltransferase (XylT). In an even more preferred embodiment, the construct is a RNA hairpin construct. These methods for altering the N-glycosylation pattern of proteins in duckweed are known in the art and are described in U.S. Pat. No. 7,884,264 to Dickey et al. The use of the RNA hairpin construct can be advantageous for obtaining a glycan profile where at least 30% of the N-glycans are G0 glycans lacking Fuc and Xyl residues and/or where the combination of G0 glycans lacking Fuc and Xyl plus high-mannose glycans are at least 70% relative to the total amount of N-glycans in the plurality of secretory IgA antibodies.

Once the transformed duckweed is obtained, the genetic modification will cause the duckweed to express the desired SIgA antibody during its otherwise normal metabolic activity. The term "express" and its grammatical variants refers to the biosynthesis of the SIgA antibody, which includes the transcription, translation, and assembly of the antibody by the duckweed. Generally this entails providing an environment to keep the duckweed alive and/or to promote growth; e.g., providing light (natural and/or artificial) and a liquid medium typically based on water. Providing this environment is often referred to as "culturing" the duckweed. Methods of culturing duckweed including the media, supplements (if any), conditions, etc., are known in the art and have been disclosed in, e.g., U.S. Pat. Nos. 6,040,498; 7,161,064; and 7,632983; and references cited therein, respectively.

Culturing of transgenic duckweed of the invention can be performed in transparent vials, flask, culture bags, or any other container capable of supporting growth using defined media. In some embodiments of the invention large scale growth of duckweed, necessary to achieve industrial production levels, is carried out in bioreactor tailor-designed for growth of duckweed. In a preferred embodiment, duckweed bioreactors, which can be inoculated aseptically, support aseptic growth of duckweed. In even more preferred embodiments, a bioreactor can be directly connected to harvest bag to separate the media from the plant material, either of which can then be piped into downstream purification steps. Suitable bioreactors, methods/devices to inoculate them aseptically, and aseptic harvest bags are described in U.S. Pat. No. 7,176,024 to Branson et al. or in US application 2010/209966 To Everett et al.

Following expression of the fully formed SIgA antibody, recovery of the antibody from the duckweed and/or the culture media is often desired. The first step, generally, is to separate the SIgA antibody from the duckweed. If the antibody is secreted and diffuses into the culture media, then a simple filter can separate the crude antibody product from the duckweed. Typically, however, the fully formed SIgA antibody is retained within the duckweed's apoplast. Separation in this case generally requires extraction.

Extraction of secreted SIgAs typically involves a homogenization step to disrupt the plant material and allow for release of the secreted SIgA from the apoplast into the homogenization buffer; also referred to as extraction buffer or extraction media. Homogenization buffers and techniques are known in the art. Small scale homogenization can be performed manually, such as by using mortar-and-pestle crushing, and the like. Larger scale homogenization is preferably performed using a mechanical mixer, typically a high shear mixer such as a Silverson 275 UHS mixer, or similar apparatuses. The buffer is typically an aqueous phosphate buffer composition though such is not required. The buffer may contain additional functional ingredients as is known in the art. For example, to reduce proteolysis by metallated proteases, EDTA may be added to the extraction buffer, typically in amounts from 1 to 20 mM, including 5 to 10 mM. Also, one or more anti-oxidants, such as ascorbic acid, sodium metabisulfite, benzyl alcohol, benzoic acid, and the like, may be added during the homogenization process. Homogenization is generally followed by centrifugation and filtration to obtain a buffer solution that contains the SIgA antibodies and other soluble proteins.

To remove some of the unwanted soluble proteins, homogenization is often followed by clarification; a step that seeks to remove certain naturally abundant impurities including (host cell proteins), such as RuBiSco, as well as non-proteinaceous impurities, such as tannins. This is usually achieved by acidic precipitation. For example, clarification can be performed by adjusting the pH of the filtrated homogenate to 4.5, followed by centrifugation (such as for 30 min at 12000), neutralization to pH 7.4, and an additional filtration step. In a preferred embodiment, pH adjustments are performed using 1 M citric acid pH 1.5, or 1M sodium acetate for acidification and 2M tris-base for neutralization, though other suitable pH adjusting agents can also be used instead of or in addition to such agents. Filtration is performed as known in the art, often by using a 0.22 μm filter.

The recovery of the SIgA antibodies from duckweed may end with the extraction buffer or the clarified material. However, for some uses, purification of the antibody is desired. Purification can be performed using known methods and techniques and generally comprises subjecting the clarified material to affinity chromatography (AC), size exclusion chromatography (SEC), and optional polishing steps. For efficiency, AC usually precedes SEC, though such is not required.

Methods of using affinity chromatography (AC) as a purification step to remove contaminant proteins and impurities are known in the art and are described in Process Scale Purification of Antibodies (2009), Edited by U. Gottschalk, J. Wiley and son, Hoboken, N.J., and references cited therein. Usually the SIgA antibody is bound to the affinity resin material while one or more impurities are not bound. The conditions are modified and the previously bound SIgA antibody is eluted from the column. The opposite can also be performed with the desired antibody passing though and the impurity or impurities being bound to the column. The light chain constant region can be the affinity target. Useful affinity columns include KappaSelect and Capto L from GE Healthcare Life Sciences (Piscataway, N.J., USA). When KappaSelect is used, the addition of MgCl2 is often advantageous. The use of Protein A as an AC column is usually avoided. Another kind of AC step is known as IMAC (immobilized copper affinity chromatography). IMAC can be used as the sole AC step or in combination with more traditional AC steps. When used, IMAC is often carried out first. If the crude antibody composition, such as the clarified material, contains EDTA, then it is advantageous to add CuSO4 to the column in order to remove EDTA, which interferes which the IMAC purification process. Often IMAC is used for small to medium scale purification of SIgA where the amounts are less than 10 g, typically less than 5 grams.

Methods of using SEC for purification of monoclonal antibodies are known in the art. In general, SEC allows the separation of fully assembled SIgAs of interest from lower molecular forms (such a monomer of IgA, J-chain and SC-chain, or combinations thereof). Furthermore, SEC also permits a buffer change, such as, for example, the reformulation of the SIgA of interest into a new desired buffer. Suitable columns include, for example, a Sephacryl S300 HR column.

Other purification steps can be employed as well. For example, ion exchange chromatography (IEX) can be useful for removing colored impurities associated with the plant material. Methods and techniques for performing IEX chromatographic purification of antibodies are known in the art and are described, e.g., in Graf et al. (1994) "Ion exchange resins for the purification of monoclonal antibodies from animal cell culture" Bioseparation, vol. 4, no. 1 pages 7-20, or in "Process scale purification of antibodies (2009) Edited by U. Gottschalk, ed. J. Wiley and son, Hoboken, N.J., and references cited therein. Often IEX, such as anion exchange chromatography (AEX) or cation exchange chromatography (CEX), is performed before IMAC or other AC step is employed, but is not limited thereto and can be employed at other points of the purification and/or can be employed multiple times with the same or different exchange resin (e.g., AEX and subsequently CEX). In some embodiments an AEX column such as DOWEX 1X2 is employed, often before the AC column.

Further polishing/purification steps can be added, as is known in the art. For example, after any and/or each purification step (chromatography step) an ultrafiltration (UF) step can be performed. Typically, a UF step is performed at or near the end of the polishing phase in order to increase purity and/or change the buffer or concentration of antibody in the buffer.

The SIgA antibodies are often sufficiently recovered so as to be "isolated" or in an isolated form. Isolation is thus related to purification and is generally achieved by completion of the recovery/extraction step, clarification, and/or capture steps described above.

Pharmaceutical Compositions

The SIgA antibodies of the invention can be used in various pharmaceutical compositions. Typically the pharmaceutical composition comprises the antibody and at least one pharmaceutically acceptable excipient. The pharmaceutical compositions can be solid, semi-solid, or liquid. Generally the pharmaceutical composition is adapted for a particular route of administration. For example, the pharmaceutical composition can be adapted for oral administration, rectal administration, buccal administration, topical administration, etc. Preferably, the pharmaceutical composition is adapted for oral administration.

Pharmaceutical compositions for administering SIgA antibodies via topical administration include powders, creams, ointments, gels, lotions, solutions and suspensions (including mouth washes). The excipient carrier is often aqueous, oil, or polymer based, each optionally in the form of an emulsion or microemulsion. The term "topical administration" includes, for example, optical administration (e.g., via a cream/ointment) and administration to the skin (e.g., at an inflamed joint).

Pharmaceutical compositions for administering the antibody via oral administration include solid oral dosage forms such as tablets, capsules, enteric coated forms thereof, lozenges, and films, as well as liquid dosage forms including solutions, suspensions, liquid filled capsules, and mouth washes. Tablets can be soluble tablets, dispersible tablets, effervescent tablets, chewable tablets, lyophilized tablets, coated tablets (e.g., sugar-coated or enteric-coated), and modified release tablets. Capsules include hard gelatin capsules that can be filled with powder, pellets, granules, small tablets, or mini-tablets, or solutions or emulsions or combinations and can be coated for enteric or modified release. Soft capsules are also contemplated and are more typically filled with liquids, gels or dispersions, but are not limited thereto. Granules can be effervescent granules, coated granules (e.g., sugar-coated or enteric-coated), and modified release granules. Although the SIgA antibody of the present invention is preferably administered orally, it should be understood that such administration may be considered to be a topical administration to the GI tract. Likewise, a suppository or rectal injection may also be used to topically trat the intestines. The use of an oral dosage form to treat gastrointestinal disease(s) using the sIgA of the present invention is a specific aspect of the present invention.

Pharmaceutical compositions for administering the SIgA antibody via parenteral administration are typically liquid. Water is commonly used as a main excipient, although other pharmaceutically-acceptable liquids such as ethanol, glycerol, ethyl oleate, Myglyol, benzyol oleate, castor oil, MCT, benzyl alcohol isopropyl myristate can be used alone or in combination with water or each other. Aqueous compositions that contain no other excipients are also contemplated, and can be prepared from lyophilized, amorphous, or crystalline compounds. Often the injectable composition, which can be for subcutaneous, IM, or IV injection, contains isotonizing agents. An injectable solution or suspension is typically sterile, as are all liquid pharmaceutical dosage forms.

An overview of dosage forms can be found in *Ansel's Pharmaceutical Dosage forms and Drug Delivery Systems.* 9$^{th}$ ed. L. V. Allan, N. G. Popovitch, H. C. Ansel, 2010 Lippincott, ISBN: 978-0781779340; *Formularium der Nederlandse Apothekers.* 2004 WINAp ISBN 90-70605-75-9; *Recepteerkunde*, G. K. Bolhuis, Y. Bouwman-Boer, F. Kadir en J. Zuiderma, 2005 WINAp ISBN 90-70605-65-1; and *Apothekenrezeptur und-defektur. Deutscher Apotheker Verlag* Stuttgart 1986 ISBN 3-7692-1092-1. See also U.S. Pat. No. 7,147,854 for a description of topical preparations for delivering IL-8 antibodies to treat skin inflammatory disease such as psoriasis.

The pharmaceutical composition generally contains about 0.01 to 1000 mg of the antibody per dose, depending in part upon the dosage form employed. The dose can be, for example, fixed or variable (e.g, based on body weight) Pharmaceutically-acceptable excipients are known in the art and include diluents, carriers, fillers, binders, lubricants, disintegrants, glidants, colorants, pigments, taste masking agents, sweeteners, plasticizers, and any acceptable auxiliary substances such as absorption enhancers, penetration enhancers, surfactants, co-surfactants, preservatives, anti-oxidants and specialized oils. Specific to the field of biopharmaceutical proteins are excipients intended to stabilize proteins and cryo-protectants to provide protection during freeze-drying. Suitable excipient(s) are selected based in part on the dosage form, the intended mode of administration, the intended release rate, and manufacturing reliability. Non-limiting examples of commonly used excipients include polymers, waxes, calcium phosphates, sugars (e.g., trehalose, sucrose, or mannitol), buffers (such as phosphate, acetate, citrate, histidine, or glycine based buffers at pH between 5 and 7.5), salts (e.g., NaCl or NaEDTA), polysorbate 20, polysorbate 80, human albumin, dextran, and benzyl alcohol.

Treatments

As used herein, the term "treat" or "treatment" means the application or administration of a SIgA antibody of the invention, alone or as part of a composition, to a patient with the purpose to cure, heal, alleviate, improve or prevent an inflammatory disease. The term "inflammatory disease" means a condition associated with symptoms of inflammation, which may be caused by external factors, such as infectious disease, or by internal dysfunctions, such as an autoimmune disease. In this context, the terms disease, disorder, syndrome, condition, and the like are used interchangeably. In embodiments, the SIgA antibodies of the present invention are useful in the topical treatment of inflammatory diseases in humans, e.g., local administration to the site of inflammation, such as orally or rectally. Preferably, the SIgA antibodies of the present invention are useful in the oral treatment of inflammatory diseases.

As used herein, an amount of the SIgA of the present invention effective to treat an inflammatory disease, or a "therapeutically effective amount," refers to an amount of the antibody which is effective beyond that which is expected in the absence of such treatment.

As used herein, the term "patient" is intended to include humans and non-human animals. The term "non-human animals" includes all vertebrates, e.g., non-mammals (such as chickens, amphibians, reptiles) and mammals, such as non-human primates, sheep, dog, cow, horse, pig, etc. In a preferred instance, the patient is human.

The SIgA antibodies of the present invention are generally useful in treating inflammatory diseases in humans. Specific targets include rheumatoid arthritis, inflammatory bowel disease (including Crohn's disease and ulcerative colitis), psoriasis, psoriatic arthritis, ankylosing spondylitis, juvenile idiopathic arthritis, uveitis, asthma, Alzheimer's disease, multiple sclerosis, type II diabetes, systemic sclerosis, lupus nephritis, and allergic rhinitis. The present invention will be further illustrated in the following non-limiting examples.

ANTI-TNF-α SIGA EXAMPLES

Example 1

Transient Expression of an Anti-TNF-α Secretory Protein Based on Infliximab (IIB-SA2n) in Plants a) Preparation of cDNA Constructs The amino acid sequences of a suitable leader sequence (e.g., secretion signal, SEQ ID N0:23), the heavy chain variable region of infliximab (SEQ ID N0:2), and the human α2(n) IgA heavy chain constant region (Chintalacharuvu et al., *Journal of Immunology*, 1994, 152, 5299-5304; SEQ ID N0:13) were joined together. Cleavage of the signal sequence (a.a. 1-19) corresponded to the predicted cleavage site using the SignalP program. This program is available online via the site of the Center for Biological Sequence Analysis at the Technical University of Denmark.

The resulting amino acid sequence was back-translated into a cDNA sequence optimized for expression in maize (*Z. mays*) (SEQ ID NO:27) (see Liangjiang Wang and Marilyn J. Roossinck., "Comparative analysis of expressed sequences reveals a conserved pattern of optimal codon usage in plants." *Plant Mol Biol* (2006) 61:699-710).

Similarly the cDNA sequence for the light chain of the construct was obtained by joining the sequences of a suitable secretion signal (SEQ ID NO:24), the light chain variable region of infliximab (SEQ ID NO:3), and the human κ Ig light chain constant region (SEQ ID NO:14), and back-translating the obtained amino acid sequence into a cDNA sequence optimized for expression in maize (*Zea mays*) (SEQ ID NO:29).

The cDNA sequence for the human J-chain was obtained by joining the amino acid sequences of secretion signal (SEQ ID NO:22) and J-chain sequence (SEQ ID NO:20), both obtained from UniprotKB/Swiss-Prot database entry P01591, and back-translating the obtained amino acid sequence into a cDNA sequence optimized for expression in maize (*Z. mays*) (SEQ ID NO:33).

The cDNA sequence for the SC-chain was obtained by joining the amino acid sequences of a suitable secretion signal (SEQ ID NO:25) and SC-chain sequence (SEQ ID NO:21, amino acids 19-603 of UniprotKB/Swiss-Prot database entry P01833), and back-translating the obtained amino acid sequence into a cDNA sequence optimized for expression in maize (*Z. mays*) (SEQ ID NO:35). The used secretion signal sequence was derived from the natural SC secretion signal by the addition of codons for two extra amino acids in order to obtain more favorable splicing sites for the construction of plasmid vectors.

The cDNA's of the four constructs (the heavy chain, the light chain, the J-Chain and the SC-Chain) were obtained from a commercial source.

b) Vector Construction and Cloning Strategy

The cDNAs for the heavy chain of the construct (HC) and of the J-chain (JC) were ligated into the pGA15 and pGA14 plasmid vectors, respectively, using PacI and AscI restriction sites. After transfer to E. coli K12 XL10 gold and expansion, the constructs were each transferred to separate pRAP plasmids using NcoI and KpnI restriction sites, resulting in the expression cassettes 35S:HC:Tnos and 35S:JC:Tnos. The pRAP plasmids containing the expression cassettes were transferred to and expanded in E. coli K12 DH10B.

The cDNAs for the light chain (LC) and of the SC-chain (SC) were ligated into the pGA14 and pGA15 plasmid vectors, respectively, using PacI and AscI restriction sites. After transfer to E. coli K12 XL10 gold and expansion, the constructs were each transferred into separate pTR2 plasmids using NcoI and XbaI restriction sites, resulting in the expression cassettes TR1'TR2':LC:T35S and TR1'TR2':SC:T35S. The pTR2 plasmids containing the expression cassettes were transferred to and expanded in E. coli K12 DH10B.

The light chain expression cassette TR1'TR2':LC:T35S was transferred to the pRAP vector containing the heavy chain expression cassette 35S:HC:Tnos using HindIII restriction sites, and transferred to and expanded in E. coli K12 DH10B. Finally, the combined cassettes containing HC and LC (35S:HC:Tnos: TR1'TR2':LC:T35S) were transferred to a pBIN+ expression vector using AscI and PacI restriction sites. This pBIN+ vector containing the combined HC and LC cassettes was transferred to Agrobacterium tumefaciens strain MOG101 using electroporation. Similarly the cassettes containing JC and SC (35S:JC:Tnos: TR1'TR2':SC:T35S) were combined in a pBIN+ expression vector. This pBIN+ vector containing the combined JC and SC cassettes was transferred to A. tumefaciens strain MOG101 using electroporation.

The two transfected A. tumefaciens strains were used in combination for transient plant transformation and expression of the full SIgA construct. For vector information see also van Engelen et al., Plant Molecular Biology 1994, 26: 1701-1710. Information on AlMV leader sequence: van der Vossen et al, Nucleic Acids Research 1993, 21: 1361-1367. pBIN+ is described in: van Engelen et al., Transgenic Research 1995, 4: 288-290. (In the referenced literature sources: pRAP35=pCPO31). By way of example, FIG. 6 shows a schematic representation of the building of the pBIN+ vector containing the combined HC and LC cassettes.

c) Transient Expression in Tobacco Plants

The youngest fully expanded leaves of six week old tobacco plants were infiltrated with a mixture of the two A. tumefaciens strains by placing a 2-ml syringe (without needle) containing the bacterial cell suspension at the lower side of a leaf and gently pressing the suspension into the leaf. The infiltrated area was usually clearly visible. Expression took 4-6 days with optimum levels at days 5-6.

The leaves were frozen at −80° C., crushed and 2 ml extraction buffer per gram of leaf material was added. The extraction buffer was PBS pH=7.4; 0.02% Tween-20 (v/v); 2% polyclar AT (v/v); and 1% inhibitor cocktail (v/v). The suspension was homogenized with an Ultra Turrax (Janke & Kunkel). Solid material was removed by centrifugation (15 minutes, 10.000 g). The solid material was extracted twice more with extraction buffer, the same as above except the inhibitor cocktail was replaced with 10 mM PMSF. The combined extracts were stored at −20° C. Using SDS-page and immunoblotting, formation of a complete SIgA could be shown, but the product was not isolated or purified. The SIgA comprises IgA(2)(n) heavy chain constant region, human κ light chain constant region, and the heavy and light chain variable regions of infliximab, and is referred to herein as "IIB-SA2n"

d) Transient Expression in Lettuce

The SIgA construct was transiently expressed in lettuce by vacuum infiltration using the same vectors as for expression in tobacco (see: Negrouk et al., Highly efficient transient expression of functional recombinant antibodies in lettuce., Plant Science 2005, 169, 433-438). Full grown crops of lettuce Lactuca sativa L. (oak leaf lettuce) and vacuum infiltrated with a mixture of the two A. tumefaciens strains and harvested 3-5 days after infiltration. Formation of complete SIgA could be shown, but the product was not isolated or purified.

Example 2

Expression of an Anti-TNF-α Secretory Protein Based on Infliximab (JIB-SA2n) in Mammalian Cells 2a: Transient Expression of IIB-SA2n (1) Vector Generation:

cDNAs encoding SIgA heavy chain (HC), light chain (LC), J-chain, and SC-chain were cut from the pGA14 and pGA15 plasmids described in Example 1. The excised HC and LC sequences were PCR amplified and cloned into pMQR-hIgG1 (Neo) to give pMQR-zmα2-iib (Neo) and pMQR-zmκ-iib (Neo) vectors. Similarly, the excised J-chain and SC-chain were PCR amplified and cloned into pMQR-kappa (Hygro) to give the pMQR-zmJ (Hygro) and pMQR-zmSC (Hygro) vectors. The pMQR-hIgG1 (Neo) and pMQR-kappa (Hygro) vectors are based on the pcDNA3 (Invitrogen) backbone, which was modified to receive any combination of Ig V- and C-region "cassettes". This was performed by subcloning well-defined genomic Ig gene segments into pcDNA3, after which silent mutations were introduced flanking the V- and C-regions to create restrictions sites allowing for the exchange of V- and C-gene segments. Other occurrences of these specific introduced restriction sites were removed from the vector backbone to ensure proper exchange of V and C regions on unique restriction sites. In short, the BsmI site was removed by exchanging the original BsmI sequence (5'-TGCATTC-3') present in the vector into 5'-TGCAAAC-3'. Furthermore the MunI/MfeI and HindIII sites were destroyed by restriction digestion followed by end-filling and re-ligation.

Large-scale production of each of the four expression vectors for transfection was performed using Maxiprep-kits (Sigma).

(2) Cell Transfection and Culture:

Transient SIgA producing CHO-S and HEK-293F cells (Invitrogen) and HEK293-EBNA1 (ATCC CRL-10852) were made as follows: Invitrogen derived cell types were used as host for transfection using FreeStyle Max or Amaxa Nucleofection. HEK293-EBNA1 was used for large scale (10 l) transient polymer transfection. To obtain a complete SIgA-producing transfectant, all 4 different vectors were transferred simultaneously into each of these cell types (CHO-S, HEK293F, and HEK203-EBNA1).

(3) FreeStyle MAX Transfection

To transfect 30×10$^6$ CHO-S and HEK-293F cells (separately), 9,375 ug of each vector was used. SIgA production was performed by culturing cells in a 200 ml shake flask at 37° C., 130 rpm and 8% $CO_2$ during 120 hours in respectively CHO-S FreeStyle and 293F FreeStyle medium. The cell conditions and transfection efficiency were determined by GUAVA ViaCount and Expresse Pro analysis to guarantee the optimal cell growth conditions in between $0.5 \times 10^6$ to $2.0 \times 10^6$ cells/ml. Each time the cells had to be diluted the volume was increased and if necessary transferred to a 500 ml baffled shake flask.

CHO-S/SIgA 24 hours post transfection: Transfection efficiency; 25.04% and cell viability; 91.59%.

HEK-293F/SIgA 24 hours post transfection: Transfection efficiency; 25.52% and cell viability; 80.36%.

(4) Amaxa Transfection

To transfect $1 \times 10^6$ Invitrogen's CHO-S or HEK-293F cells 1 ug of each vector was used. SIgA production was performed by static culturing cells in a T25 flask at 37° C. and 5% $CO_2$ during 96 hours. At 96 hours post transfection cell suspensions fractions were taken for production analysis.

CHO-S/SIgA 24 hours post transfection: Transfection efficiency; 54.27% and cell viability; 94.19%.

HEK-293F/SIgA 24 hours post transfection: Transfection efficiency; 61.57% and cell viability; 68.15%.

(5) Polymer Transfections

Transfections of HEK293-EBNA1 cells were performed essentially as described by Durocher at al. *Nucleic Acids Res.* 30, E9 (2002) (see also Morlot C. et al., *Acta Crystallogr Sect F Struct Biol Cryst Commun.* 63, 689-91 (2007)). The day prior to transfection, the cells were routinely diluted 4-5 times in fresh Freestyle medium (without further addition of FCS or G418) to a density of $0.3 \times 10^6$/ml. The next day transfection mixtures were prepared. For transfection of 1 liter of cell culture 500 µg of high quality DNA was diluted in 25 ml OptiMEM medium (Invitrogen) 1 ml of a 1 mg/ml stock solution of linear 25 kDa PEI (Polysciences) was added to the mixture and immediately vortexed for 10 seconds. After 10 minutes for incubation the DNA:PEI mixture was added to the cells. Cells or conditioned medium were routinely harvested six days post transfection. Culture was performed at 10 L scale. The anti-TNF-α secretory IgA antibody, IIB-SA2n, in the supernatant of this culture can be isolated and purified as described in Example 3a.

2B: Stable Expression in HEK293F of IIB-SA1

(1) Vector Construction cDNA encoding the heavy chain variable region of infliximab was cut from the previously obtained vector pMQR-zmα2-iib (Neo) (see Example 2a(1)). This cDNA was fused into a pMQR vector containing the human genomic DNA sequence encoding the IgA α1 heavy chain constant region to give vector pMQR-huα1-iib (Neo). Similarly, the light chain variable region of infliximab was cut from pMQR-zmκ-iib (Neo) and transferred to a pMQR vector containing the human genomic DNA sequence encoding the κ-light chain constant region to give vector pMQR-huκ-iib (Neo). The two vectors pMQR-huα1-iib (Neo) and pMQR-huκ-iib (Neo) were fused into a single vector pMQR-huIgA1-iib (Neo) (SEQ ID NO:28).

Previously obtained vectors pMQR-zmJ (Hygro) and pMQR-zmSC (Hygro) were also combined into a single vector PMQR-zmJ/SC (Hygro) (SEQ ID NO:30).

(2) Transfection

HEK-293F cells were transformed with both of the two vectors described above using polymer transfection as described in experiment 2a(5). Cells were grown in neomycin and hygromycin containing medium. After recovery, cells were grown on semisolid medium with neo/hygromycin and clones were selected using Clonepix analysis and selection. A suitable clone (2D5) was selected. Clone 2D5 was expanded under various conditions and scales. Ultimately 15 L of culture medium containing 440 mg of complete SIgA (according to ELISA analysis) was obtained from the expanded 2D5 cells. The SIgA comprises IgA(1) heavy chain constant region, human κ light chain constant region, and the heavy and light chain variable regions of infliximab; and is referred to herein as "IIB-SA1." IIB-SA1 can be isolated from culture medium and purified as described in Example 3b.

Example 3

Purification of Anti-TNF-α Secretory IgA Antibodies (IIB-SA2n and IIB-SA1) from Mammalian Cell Culture 3a—Affinity and SEC (IIB-SA2n)

The supernatant obtained from the transient expression of IIB-SA2n in HEK-293-EBNA1 cells using polymer transfection (experiment 2a(5)) was purified using affinity chromatography with an anti-IgA *lama* antibody fragment immobilized on sepharose (CaptureSelect human IgA, BAC, product code 2880) followed by SEC.

(1) Affinity Chromatography:

Anti-human IgA matrix (Capture Select) was poured into a XK16/20 column (16×200 mm) in 20% ethanol in MilliQ water at a flow rate of 15 ml/min. After adjusting the position of the upper flow adaptor, the column was equilibrated in PBS buffer pH 7.4. The HEK-cell culture medium was filtered to remove large cell debris and subsequently loaded on the pre-equilibrated anti-human IgA column with a flow rate of 4.5 ml/min After washing with 10 column volumes PBS pH 7.4, the active secretory IgA antibody was isocratically eluted from the column with 5 column volumes of citrate/arginine/NaCl buffer pH 2.5, followed by immediate neutralization to pH 7.7 with a 1 M Tris stock solution.

(2) SEC Chromatography:

In the second step, the adjusted pool from the first step was concentrated 4-fold down to 5 ml using a Vivaspin 15R device (30 kDa cut-off filter) and loaded on a prepacked Superdex 200 16/60 GL column equilibrated with PBS pH 7.4. The sample loading volume was 4% of the bed volume and the flow rate was 1.5 ml/min. This size exclusion gel filtration step resulted in fractionation of SIgA and monomeric IgA according to their molecular weights. The elution fractions containing SIgA or monomeric IgA as determined by non-reducing SDS-PAGE were pooled separately and subsequently concentrated 10-fold using a Vivaspin 15R device (30 kDa cut-off filter).

Samples of substantially pure IIB-SA2n and the corresponding monomeric anti-TNF-α IgA were collected and characterized.

3b—Jacalin Affinity and SEC (JIB-SA1)

Culture medium obtained from HEK-293F clonal cell line 2D5 expressing IIB-SA1 (see Example 2b) was purified using Jacalin affinity chromatography followed by SEC.

(1) Jacalin Affinity Chromatography 500 ml culture medium was filtered through a 0.45/0.2 µm Sartopore 2 filter. A Jacalin column was prepared by packing 15 ml of immobilized Jacalin resin (Pierce art nr. 20395) in an omnifit 15 mm glass column. The column was equilibrated using 5 column volumes of PBS buffer pH 7.4. Culture medium was loaded at a flow rate of 3 ml/min. after washing with 5 column volumes of PBS buffer pH7.4 at 5 ml/min followed by elution of bound material with 8 column volumes of PBS buffer pH7.4 containing 0.5M galactose. The fractions of the eluate containing SIgA were pooled (detection by UV OD280 measurement). The pooled eluate (64 ml) was concentrated to a volume of 5 ml using Vivaspin filters. Measurement of SIgA content using ELISA showed that only appr. 30% was bound to the Jacalin, the remainder being in the flow-through fraction.

(2) SEC Chromatography

The concentrated eluate was placed in a superloop and loaded on a Sephacryl S300 column (GE-Healthcare art.nr. 17-1167-01) with a flow rate of 1 ml/min. The product was eluted using 1.5 column volumes of PBS buffer (50 mM phosphate pH 7.4) containing 0.5M arginine. The chromatogram (UV OD280 detection) showed three overlapping peaks. Fractions were analysed by SDS-PAGE to identify the SIgA containing fraction. The fractions containing the product were pooled. Reducing and non-reducing SDS-PAGE analyses of the purified product, IIB-SA1, are shown in FIG. 7.

Example 4

Stable Expression of Anti-TNF-α Secretory IgA Antibody (ADB-SA1g) in *Lemna*

Anti-TNF-α SIgA was produced in *Lemna* by stable insertion of DNA coding for the following proteins: The amino acid sequence of the heavy chain consisted of the *Oryza sativa* (rice) amylase secretion signal (SEQ ID NO:26) attached to the N-terminal amino acid of the heavy chain variable region of adalimumab (anti-TNF-α IgG1, Humira®, CAS number 331731-18-1) (SEQ ID NO:4) attached to the N-terminal amino acid of a human IgA1 heavy chain constant region (SEQ ID NO:10). The amino acid sequence of the light chain of the Anti-TNF-α SIgA combines the rice α-amylase secretion signal (SEQ ID NO:26) with the TNF-α binding light chain variable region of adalimumab (SEQ ID NO:5) and the human κ-light chain constant region (SEQ ID NO:14). The amino acid sequence of the J-chain consisted of the rice α-amylase secretion signal (SEQ ID NO:26) attached to the N-terminal amino acid of the human J-chain (SEQ ID NO:20). The amino acid sequence of the SC-chain consisted of the rice amylase secretion signal (SEQ ID NO:26) attached to the N-terminal amino acid of the human SC-chain (SEQ ID NO:21). The produced SIgA, having IgA1 heavy chain constant region, human κ-light chain constant region, and adalimumab heavy and light chain variable regions, combined with human J-chain and SC-chain is referred to as ADB-SA1.

Genes were designed for each of the four components with *Lemna minor* preferred codon usage (63-67% GC content). Tables with suitable preferred codon use in Lemnaceae can be found in PCT application WO2005/035768 and in relevant references contained therein. The synthetic genes also contained the rice α-amylase signal sequence (GenBank M24286; SEQ ID NO:26) fused to the 5' end of their coding sequences. Restriction endonuclease sites were added to allow cloning into *A. tumefaciens* binary vectors. Design of DNA sequences and vector construction was performed by Biolex Therapeutics, Inc., Pittsboro, N.C., USA. DNA sequences were produced by DNA2.0 (Menlo Park, Calif., USA).

The ADB-SA1g antibody was expressed in *L. minor* by transfection via an *A. tumefaciens* binary vector containing DNA sequences encoding all four of the SIgA components: J-chain (SEQ ID NO:34), SC-chain (SEQ ID NO:36), H-chain (SEQ ID NO:31) and L-chain (SEQ ID NO:32). To prepare this vector, independent expression cassettes were created containing a promoter and also DNA sequences encoding the protein and terminator for the J-chain, SC-chain, H-chain and L-chain. The H chain was fused to the modified chimeric octopine and mannopine synthase promoter with *Lemna gibba* 5' leader from ribulose bis-phosphatecarboxylase small subunit-1. The L-chain, SC-chain and J-chain genes were fused to high expression Lemnaceae Ubiquitin promoters *L. minor* polyubiquitin promoter (LmUbq), *Lemna aequinoctialis* polyubiquitin promoter (LaUbq) and *Spirodela polyrrhiza* polyubiquitin promoter (SpUbq), respectively. Sequences of these promoters have been disclosed in PCT application WO2007/124186. These expression cassettes were then cloned into a single *A. tumefaciens* transformation vector EC2.2 (a modification of the *A. tumefaciens* binary vector pBMSP3, which is a derivative of pBINPLUS. See Ni, M., Cui, D., Einstein, J., Narasimhulu, S., Vergara, C. E., and Gelvin, S. B., *Plant J.* 7, 661-676, (1995), van Engelen, *Transgenic Res.* 4:288-290 (1995), and Gasdaska et al., *Bioprocessing J.,* 3:50-56 (2003)), with the appropriate restriction sites to create the final transformation vector SynB02. This vector also contained the gentamicin acetyltransferase-3-I gene (aacC1) which confers resistance to gentamicin and allows for selection of transgenic *L. minor* lines.

SynB02 was used to create an additional transformation vector to generate a glycan optimized version of anti-TNF-α SIgA, having G0 glycans lacking fucose and xylose residues. A chimeric hairpin RNA was used to silence endogenous *L. minor* mRNAs encoding α-1,3-fucosyltransferase (Fuct1, GenBank DQ789145) and β-1,2-xylosyltransferase (Xylt1, GenBank DQ789146). A DNA sequence for this chimeric RNAi molecule was fused to the high expression SpUbq promoter and subsequently moved into the SynB02 vector creating the final transformation vector SynB03. Further details on production of glycan optimized proteins in Lemnaceae can be found in PCT applications WO2007/084672, WO2007/084922, WO2007/084926 and in Cox, K. M., *Nature Biotechnology* 2006, 12: 1591-1597.

*L. minor* strain 8627 was transfected with vector SynB03, and glycosylation modified *L. minor* strain XF04 was transfected with vector SynB02. Once transformed plants were regenerated (approximately three months), single plants were harvested from the antibiotic selection plates and propagated separately in liquid growth media, without selection antibiotic, for further screening and characterization. Thus several hundred individual transgenic plant lines from each construct were generated. Independent transgenic lines were harvested and clonally propagated in individual harvest jars. For screening of transgenic lines, clonal lines were preconditioned for 1 week at light levels of 150 to 200 μmol/m²·s in vented plant growth vessels containing SH medium (Schenk R. U. et al., *Can. J. Biol.* 1972, 50: 199-204) without sucrose. Fifteen to twenty preconditioned fronds were then placed into vented containers containing fresh SH medium, and allowed to grow for two weeks. Tissue samples from each line were collected and frozen for analysis.

To determine SIgA expression, frozen tissue samples were homogenized and centrifuged, and the supernatant was removed and screened by an ELISA method using sheep anti-human IgA secretory chain (AbD Serotec catalog #5111-4804-1:1000 dilution) coated plates to capture the SIgA antibody. The samples were then detected using a goat anti-human kappa light chain HRP conjugated antibody (Sigma catalog #A7164-1:2000 dilution). The highest-expressing lines from this primary screening were then grown again for two weeks in small research vessels under the optimal growth conditions. The resulting tissue was harvested and the ELISA was performed to determine the percent of the total soluble protein that is the expressed SIgA antibody (ADB-SA1g). The results are summarized in Table 3.

TABLE 3

| Construct | Glycosylation | # of lines screened | Highest Expression level |
|---|---|---|---|
| SynB02 | G0 glycans | 55 | 16.2% TSP |
| SynB03 | G0 glycans | 227 | 13.6% TSP |

Figure 8:
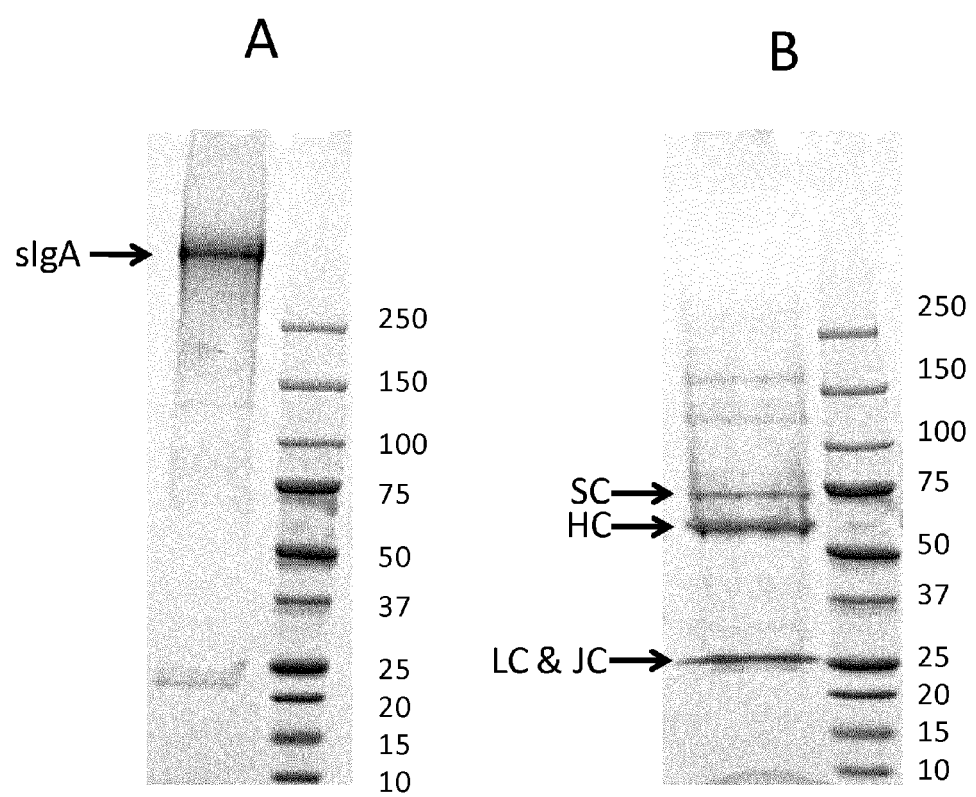
FIG. 8 shows reducing and non reducing gels of an anti-TNFα SIgA of the invention, having adalimumab variable regions and being produced in *Lemna*. The label "A" shows non-reducing SDS-PAGE analysis demonstrating expression of complete SIgA while the label "B" shows reducing SDS-PAGE analysis.

Results of non-reducing and reducing SDS-PAGE analyses of purified material obtained from *Lemna* transfected with construct SynB02 are shown in FIG. 8. ADB-SA1g can be isolated from *Lemna* culture and purified as described in Example 5.

Example 5

Isolation and Purification of Anti-TNF-α Secretory IgA Antibody ADB-SA1g from *Lemna*

Biomass from transgenic *Lemna* expressing anti TNF-α SIgA, having variable regions that are the amino acid sequence of the variable regions (antigen binding regions) of adalimumab, was homogenized in 50 mM Sodium phosphate, 0.3M Sodium chloride, buffer pH 7.4, at a buffer to tissue ratio of 4:1. An acid precipitation step was performed on the crude extract to remove ribuloase bis-phosphate carboxylase (RuBisCo) and other plant proteins by adjusting the extract to pH 4.5 using 1M Sodium acetate, pH 2.5. The precipitate was removed by centrifugation of the material at 14,000×g for 30 minutes at 4° C. The supernatant was adjusted to pH 7.4 and loaded on DOWEX (Dowex 1X2 anion exchange resin) to remove colored impurities. The flow-through fraction containing anti TNF-α SIgA was 0.22 µm was filtered prior to chromatography using affinity chromatography and Size Exclusion Chromatography.

Affinity purification: A KappaSelect (GE Healthcare prod. Nr. 17-5458-03) column was prepared according to manufacturer instructions (28-9448-22 AA). The column was equilibrated with 5 column volumes (cv) of TBS buffer (50 mM Tris, 0.15M Sodium chloride, pH 7.4). The supernatant was loaded on the column Approximately 5 mg sIgA/ml resin was loaded on columns of up to 1 L KappaSelect. Non-binding material was washed from the column with 5 cv TBS buffer. The product was eluted from the column using 10 cv of 25 mM Sodium Acetate, pH 6.6 buffer containing 3.5 M MgCl$_2$. The fractions containing the secretory proteins were pooled and immediately diluted 4-fold using TBS buffer (50 mM Tris, 0.15M Sodium chloride, pH 7.4). MgCl$_2$ was replaced by buffer exchange with at least 10 volumes of TBS buffer using a Pall Centramate cassette ultrafiltration system and a Pellicon 2 Mini Filter (Millipore prod.Nr. P2C005C01-PLCCC 5K, regenerated cellulose) with 5 kDa cut-off.

SEC purification: Material obtained by KappaSelect chromatography was further purified on a Sephacryl 5300 HR column. The column was equilibrated with 2 cv of PBS buffer at a flow rate of 1.0 ml/min. The KappaSelect eluate was concentrated 3-4× using ultra filtration using a Pellicon 2 Mini Filter (Millipore prod.Nr. P2C005C01-PLCCC 5K, regenerated cellulose) with 5 kDa cut-off.

Typically, a concentration of 3-5 mg/ml and feed volume of 50 ml was used for a 1 L column. The feed was applied using an AKTA purifier at 1.0 ml/min. Elution was performed with at least 2 column volumes of PBS buffer at room temperature and a flow rate of 1.0 ml/min Fractions were collected and sufficiently pure fractions were pooled.

Example 6

Binding of Anti-TNF-α SIgA IIB-SA1 to TNF-α

Binding of IIB-SA1 (infliximab binding head) after purification as described in Example 3b, to TNF-α was determined using ELISA according to the following procedure.

96-Well plates were incubated overnight at 4° C. with 100 µl/well of 0.5 µg/ml TNF-α in PBS pH7.4. After emptying the wells were incubated for 2 hours at RT with 200 µl/well of PBS pH7.4 containing 1% BSA and 0.05% Tween-20. After washing (room temperature) with 300 µl/well of PBS/0.05% Tween-20 three times for 30 seconds, shaking, the plates were used. The wells were incubated with samples, 1 hour at 37° C., 100 µl/well. The wells were washed (room temperature) with PBS/0.05% Tween-20 three times for 30 seconds, shaking, 300 µl/well. The wells were incubated with 100 µl/well of 0.5 µg/ml HRP labeled anti-human kappa light chain antibody (Sigma, A7164) for 1 h at RT, and then washed (room temperature) with PBS/0.05% Tween-20 three times for 30 seconds, shaking, 300 µl/well.

Figure 9:
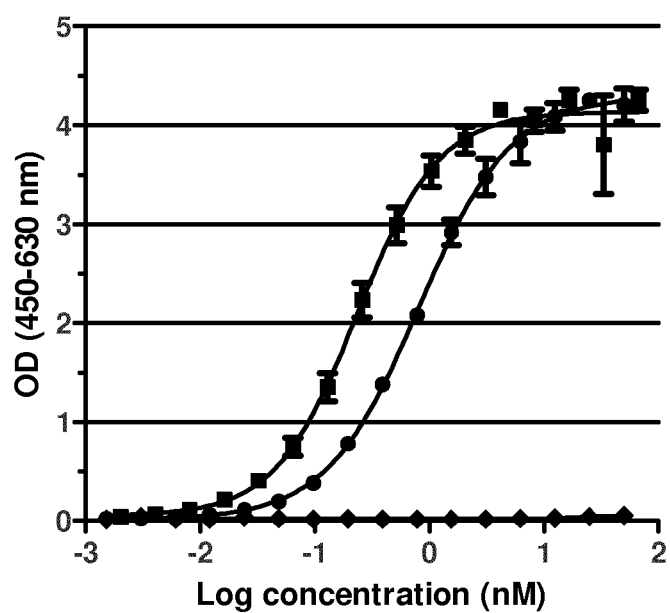
FIG. 9 shows binding curves of antibodies to TNFα. The closed circle represents a SIgA of the invention having infliximab variable regions, square represents infliximab, and diamond represents colostral secretory IgA.

For detection, the wells were incubated with TMB (Tebu Bio), 10 minutes at room temperature, 100 µl/well. The reaction was stopped with 0.3 M sulphuric acid, 100 µl/well, and the OD at 450 nm was measured with well correction at 630 nm. Measurement of IIB-SA1 from expression in mammalian cells (Example 2b) showed strong TNF-α affinity at a level comparable to that of infliximab as shown in FIG. 9. Note that the closed circle represents the SIgA of the invention (IIB-SA1), square represents Infliximab, and diamond represents Colostral SIgA. Equilibrium constants of $8.1 \times 10^{-10}$ and $2.4 \times 10^{-10}$ for IIB-SA1 and for Infliximab itself (REMICADE®), respectively, were calculated. This shows that the transfer of the TNF-α binding variable part of IgG1 antibody infliximab to a secretory IgA does not substantially alter affinity (taking the variation and discriminatory power of the experimental setup into account), and that the obtained product is fully functional.

Example 7

Proteolytic Stability of Anti-TNF-α SIgAs (IIB-SA1 and ADB-SA1g)

The stability of IIB-SA1 (Example 3b), and of ADB-SA1g (Example 4, from SynB03) was determined in simulated intestinal fluid (SIF, 0.05M phosphate buffer pH 6.8 containing 10 mg/ml pancreatin). Stability was compared to a human colostral SIgA which was purified to contain only kappa light chains and α-1 heavy chains.

Figure 10:
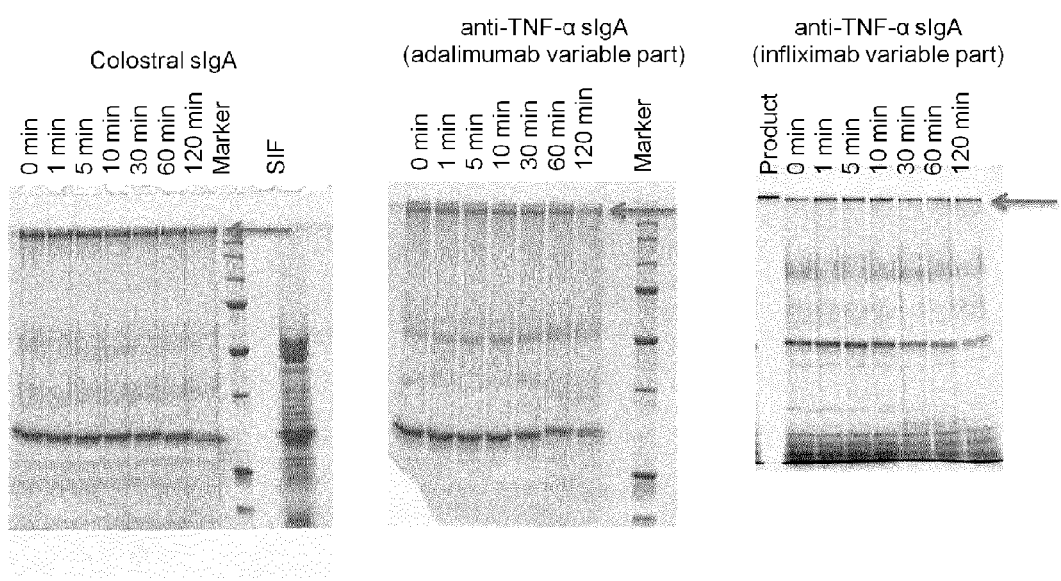
FIG. 10 shows the degradation of an anti-TNFα SIgA according to the invention having infliximab variable regions and being produced in mammalian cells, and an anti-TNFα SIgA according to the invention having adalimumab variable regions and being produced in *Lemna*, compared to colostral SIgA in simulated intestinal fluid (SIF).

150 µl of a 0.14 mg/ml solution of the material to be tested (i.e., IIB-SA1, ADB-SA1g, or human colostral SIgA (kappa light chain, α-1 heavy chain) was added to 550 µl of pre-heated SIF at 37° C. 100 µl samples were drawn at T=0, 5, 15, 30, 60 and 120 min, added to 25 ul protease inhibitor cocktail (Roche, 1169749800) followed by immediate freezing in liquid nitrogen. Samples were analyzed by non-reducing SDS-Page gel electrophoresis. Briefly; 57.5 µl of a 0.08 M solution of iodoacetamide in LDS sample buffer was added to each of the frozen samples. Samples were thawed and applied to Criterion Tris-HCl gel (12.5%, 18 well, 30 µl comb (Biorad, 345-0015). After electrophoresis gels were treated with Krypton protein stain and analyzed. Stability of the samples was qualitatively assessed visually. Results are shown in FIG. 10.

The two forms of anti-TNF-α SIgA, i.e., IIB-SA1 (labeled as infliximab variable part in FIG. 10) and ADB-SA1g (labeled as adalimumab variable part in FIG. 10) each showed a stability which was slightly less than that of the colostral SIgA.

Example 8a

Caco-2 Cell Based Assays

The aims of Caco-2 cell experiments were: (a) to evaluate in vitro the capacity of anti-TNF-α SIgA's to block the biological activity of TNF-α and (b) to study transport over an epithelial cell monolayer.

Caco-2 Cell Culture Conditions and Exposure to TNF-α

Human colonic adenocarcinoma epithelial Caco-2 cells (HTB 37, American Type Tissue Collection) were grown in C-DMEM consisting of DMEM-Glutamax (Life Technologies) supplemented with 10% fetal calf serum (FCS), 1% non essential amino acids, 10 mM HEPES, 0.1% transferrin and 1% streptomycin/penicillin Cells cultivated to 80% confluency were seeded on Snapwell filters (diameter, 12 mm; pore size, 0.4 mm; Corning Costar) at a density of $0.4 \times 10^5$ cells/cm$^2$. The formation of a polarized Caco-2 cell monolayer at week 3 was established by morphology (laser scanning confocal microscopy) and monitoring of the transepithelial electrical resistance (TER; 300-350 Ω×cm$^2$) using a Millicell-ERS apparatus (Millipore). After formation of the Caco-2 cell monolayer, the apical compartment medium was replaced by culture medium lacking FCS. One hour later, the medium lacking FCS was then replaced by medium containing 10 or 20 ng/ml of TNF-α, The polarized Caco-2 cell monolayers were sensitized with the TNF-α for 28 hours and the integrity of the monolayer was monitored by measurement of the TER.

Effect of SIgA's on Polarized Caco-2 Cell Monolayer Sensitized by TNF-α Applied Apically Caco-2 cell monolayers were established as described above. For each Snapwell insert, 10 ng TNF-α was mixed with an equimolar, or a 10-fold molar excess, of an antibody IIB-SA1 or ADB-SA1g to a final volume of 40 microliters phosphate-buffered saline (PBS). The TNF and antibody mixture was incubated for 20 minutes at ambient temperature followed by dilution with 460 microliters of culture medium lacking FCS. The medium in the apical compartment was replaced by the TNF and antibody mixture. The Caco-2 cell monolayers were sensitized for 28 hours and the integrity of the monolayer was monitored by measurement of the TER.

Figure 11:
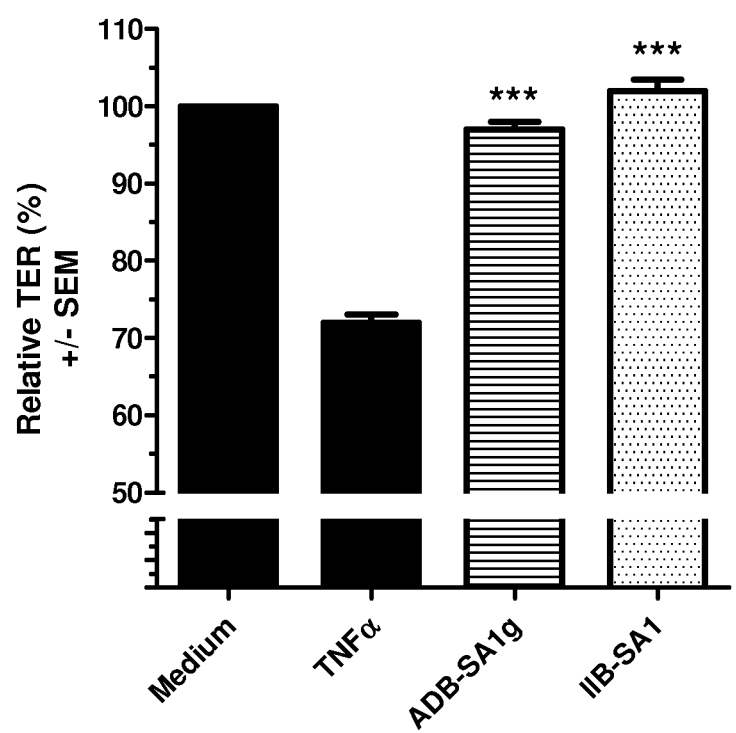
FIG. 11 shows TNFα-induced disturbance of Caco-2 monolayer integrity as measured by transepithelial electrical resistance (TER).

Results:

As shown in FIG. 11 for the 10-fold molar excess assay, taking the medium condition as 100%, the drop in TER values induced by TNF-α could be completely compensated by the presence of either anti-TNF-α SIgA preparation. The data are a mean of 6 independent replicates for each condition. Statistical analysis using ANOVA followed by Dunnett's Multiple Comparison test found a p<0.001 for the ADB-SA1g and IIB-SA1 results (indicated with *** in FIG. 11).

Effect of SIgA's on Polarized Caco-2 Cell Monolayer Sensitized by TNF-α Applied Apically: Possible Recovery after Apical Delivery.

Polarized Caco-2 cell monolayers were established as described above. The medium in the apical compartment was replaced by 20 ng/ml TNF-α as indicated above, and the polarized Caco-2 cell monolayers were sensitized for respectively 15 or 28 hours prior to addition of SIgA's (specifically IIB-SA1 or ADB-SA1g). After sensitization, Caco-2 cell were exposed to SIgA's for 24 hours and TER was monitored.

Figure 12:
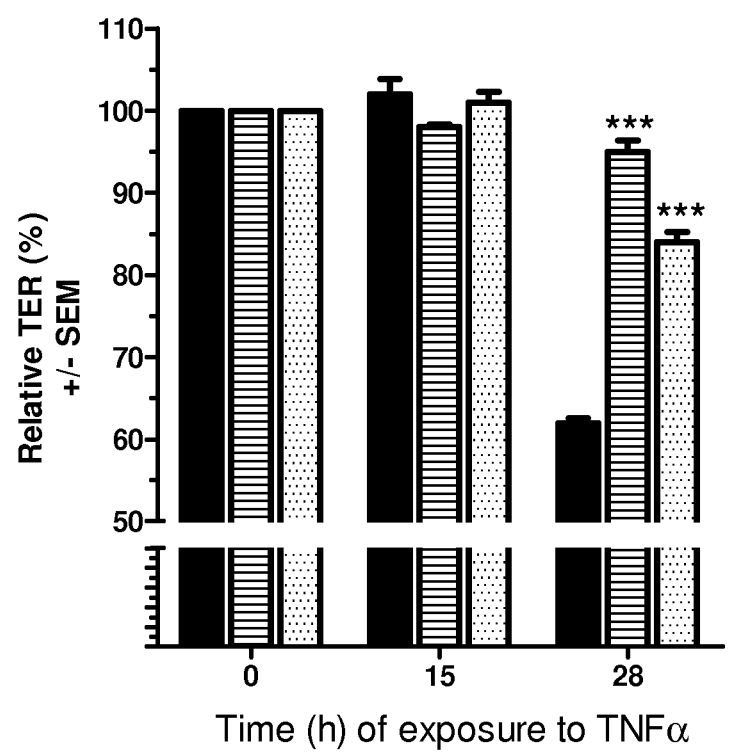
FIG. 12 shows the restoration of TNFα-induced disturbance of Caco-2 monolayer integrity as measured by TER.

Results:

The results are shown in FIG. 12. Black bars represent exposure to TNF-α only, striped bars represent addition of ADB-SA1g after indicated time of exposure to TNF-α, dotted bars represent addition of IIB-SA1 after indicated time of exposure to TNF-α. Statistical analysis using ANOVA followed by Dunnett's Multiple Comparison test, ADB-SA1g and IIB-SA1 were compared to TNF-α and had a p<0.001 (indicated by *** in FIG. 12). Data are means of 4 independent replicates Snapwell inserts for each condition. As expected, no effect was seen when adding the SIgA compounds at t=15 h, a time-point when the TER is not yet affected. At a later time-point (28 hours), which is known to dramatically affect TER (see e.g., Dongmei Ye, et al., *Am J Physiol Gastrointest Liver Physiol* 290: pp 496-504, 2006), application of the SIgA compound in the apical compartment resulted in marked recovery of the TER measured 24 hours later.

Conclusion:

These data suggests that delayed apical neutralization of the effect of TNF-α on polarized Caco-2 cell monolayers can lead to recovery, as long as the SIgA's are delivered within 28 hours post-cytokine exposure.

Tracking of the Bio-Availability of Fluorescent ADB-SA1g Applied in the Apical Compartment of Polarized Caco-2 Cell Monolayers ADB-SA1g was labeled with indocyanine Cy5 using the antibody labeling kit (General Electrics Healthcare), following the procedure provided by the kit's manufacturer. One microgram of labeled ADB-SA1g diluted in 500 microliters of FCS-free Caco-2 cell culture medium was added to the apical compartment and incubated overnight. Snapwell inserts were washed twice with PBS prior to fixation overnight with 5 ml of 4% paraformaldehyde at 4° C. After washing with PBS, filters were permeabilized with 0.2% Triton X-100, and non-specific binding sites were blocked with 5% FCS in PBS. Inserts were incubated with rabbit anti-human zonula occludens-1 (ZO-1) (1/200 dilution), washed in PBS prior to addition of secondary Ab (goat anti-rabbit IgG conjugated with Alexa Fluor 647; 1/100 dilution). After PBS washing, filters were then incubated with 4',6-diamidino-2-phenylindole (DAPI) at a concentration of 100 ng/ml in PBS (Invitrogen) for 30 min. Filters were recovered from their holders, and mounted in Vectashield (Vector Laboratories) for observation using a Zeiss LSM 710 Meta confocal microscope (Carl Zeiss, Germany) equipped with a 40× objective (Cellular Imaging Facility platform, Lausanne University, Switzerland) and processed using Zeiss ZEN 2009 light software.

Results:

Because 3D image reconstitution does not allow to finely pinpoint the location of the SIgA in contact with the Caco-2 cell monolayer, reliable tracking was carried out by analyzing successive confocal plans. Cell sections were selected at the bottom of microvilli, at the level of tight junctions, in the nuclear periphery, and at the level of the nucleus. Proper visualization was ensured by simultaneous staining with anti-ZO-1 antibodies and DAPI. ADB-SA1g was localized on the cell surface. The antibody was detected in the form of dense fluorescent spots within the cell cytosol, most likely in endocytotic/micropinocytic compartments.

Conclusion:

This indicates that intracellular distribution may serve as second line of defense and that ADB-SA1g could eventually neutralize internalized TNF-α.

Example 8b

Localization of Anti-TNF SIgA ADB-SA1g in In-Vivo Animal Models of IBD

In an animal model of IBD, disease was induced in female C57Bl/6 mice, 8 weeks of age, by topical sensibilization (day 1) with 0.5% TNBS in acetonitril (4:1), followed by a rectal challenge of 2.5% TNBS in 100% Ethanol on day 4 Animals were treated orally 3 times with ADB-SA1g (100 μg/mouse): 2 days before topical sensibilization (day −1) and on day 1 and 4. At day 6, when disease symptoms became apparent, animals were sacrificed and distal colon was collected for histological analyses. Fresh frozen tissue was fixed in 4% paraformaldehyde and washed 3 times with wash buffer (1×PBS+2% BSA). Unspecific binding sites were blocked with protein block reagent, washed 3 times and incubated with primary antibody over night at 4° C. After 3 wash steps, tissue slides were incubated with secondary antibody for 4 hours at 4° C., washed 3 times and incubated with streptavidin-Alexa488 for 1 hour at 4° C. Finally tissue slides were mounted with Vectashield mounting medium. Primary antibodies used were: sc-20656 (human SC chain) rabbit (Santa Cruz) 1:200, CD31 (Dendritic cells) rat antibody (Biolegend) 1:200, CD326 (EpCam) rat antibody (Biolegend) 1:200, CD11c (Dendritic cells) arm-.Hamster (Biolegend) 1:200 and M-cells ULEX-1: lectin-FITC directly conjugated (Sigma-Aldrich) 1:200. Secondary antibodies used were: donkey-anti-rabbit Dylight 549 nm (red) (Dianova) for sc-20565, goat-anti-rat biotin antibody (BD Pharmingen) 1:500+Streptavidin-Alexa488 nm (green) 1:200 for CD31 and CD326, and goat-anti-arm. Hamster biotin antibody (Caltag) 1:500+Streptavidin Alexa488 nm for CD11c.

Results:

To demonstrate the presence of ADB-SA1g, antibody sc-20656 was used. This antibody binds to the human secretory chain, but not to mouse secretory chain. Positive staining for ADB-SA1g was found in epithelial cells (positive for CD 326) and in dendritic cells (positive for CD11c+ and CD31+). Surprisingly, no co-localization of ADB-SA1g with M-cells was found under the above described experimental conditions.

Conclusion:

This data confirms the "tracking of the bio-availability" results from Example 8a and indicates that intracellular distribution may serve as second line of defense and that ADB-SA1g could eventually neutralize internalized TNF-α.

Example 9

Efficacy of Anti-TNF SIgA ADB-SA1g in In-Vivo Animal Models of IBD

C57BL/6 mice were pre-treated orally 5 times a week (not in weekend) with PBS control, ADB-SA1g (100 μg/mouse), or 3 times per week subcutaneous with Adalimumab (100 μg/mouse). Start of pre-treatment is t=0. At day t=7 mice were treated with 2% dextran sulfate sodium (DSS) in drinking water to induce inflammation symptoms in intestine. First signs of inflammation can be seen at day 10-12, together with declined body weight. With mini-endoscopic system an analysis of the status of disease was performed. Briefly, a mini-endoscope (1.9 mm outer diameter) was introduced via the anus and the colon was carefully inflated with an air pump. Endoscopic pictures obtained allow the monitoring and grading of inflammation. Thereafter, endoscopic scoring of five parameters from 0-3 (1; translucent structure, 2; granularity, 3; fibrin, 4; vascularity, and 5; stool) resulting in the overall score from 0 (no change) to 15 (severe colitis) was performed. Typically, after one week exposure to DSS the symptoms are so strong that mice need a resting period to recover. At day t=16 the experiment was terminated and clinical score analyzed.

Figure 13:
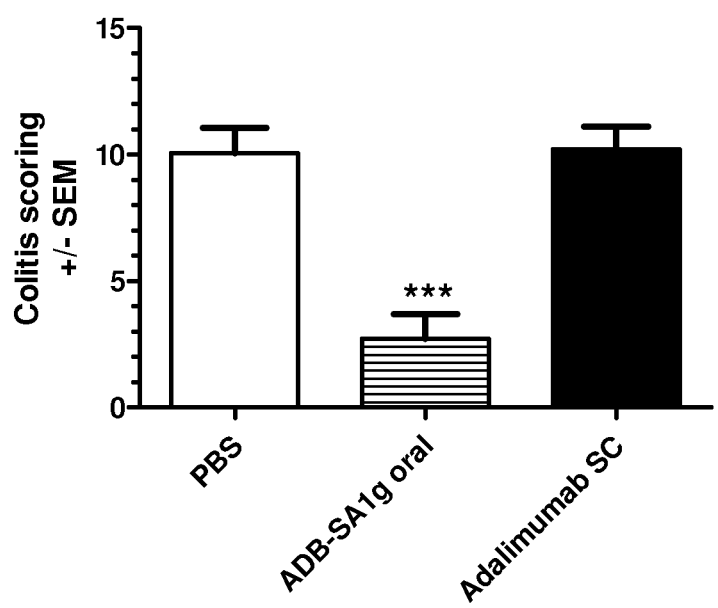
FIG. 13 represents the colitis scoring of DSS-induced inflammatory bowel disease in C57BL/6 mice with and without treatment.

The results are depicted in FIG. 13. Statistical analysis using ANOVA followed by Dunnett's Multiple Comparison test was performed comparing all groups to PBS control group. The ADB-SA1g was significant having a p<0.001 (indicated as *** in FIG. 13). n=7 mice per group. Oral treatment with ADB-SA1g significantly inhibited DSS-induced inflammatory bowel disease in C57BL/6 mice. In contrast, subcutaneous treatment with Adalimumab was not effective, even though both antibodies used the same binding head (variable region).

Figure 14:
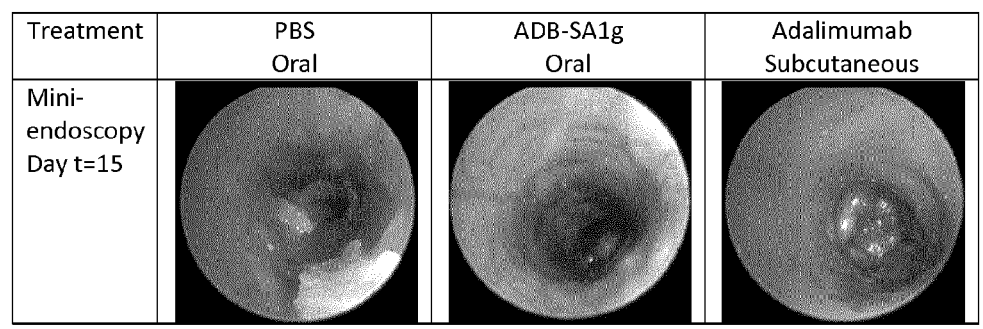
FIG. 14 is a representative depiction of mini-endoscopic pictures of the colitis score at day t=15 for a mouse from each test group.

In FIG. 14 a representative mini-endoscopic picture of the colitis score at day t=15 is depicted.

Example 10

Efficacy of Anti-TNF SIgA ADB-SA1g in an In-Vivo Animal Model of RA

The therapeutic efficacy of oral ADB-SA1g was evaluated in a rheumatoid arthritis (RA) model based on a TNFα-overexpressing transgenic mouse model which spontaneously develops arthritis.

TNF driven spondylitis mouse (TNF$^{\Delta ARE/+}$) male mice (available via BiomedCode Hellas SA, heterozygous for the mouse TNFα mutation (maintained in a C57BL/6J genetic background) were crossed with C57BL/6J females. Their heterozygous offspring used in this study were identified by tail DNA genotyping which was further confirmed by the phenotype of these anima s which exhibit a ruffled fur coat. Mixed sex mice were used in this study.

From the fourth week of age and onwards, the mice received daily (Monday-Friday) by oral gavage either drinking water, buffer (vehicle), ADB-SA1g (5 mg/kg), or subcutaneously every other day (Mon-Wed-Fri) etanercept (10 mg/kg).

Figure 15:
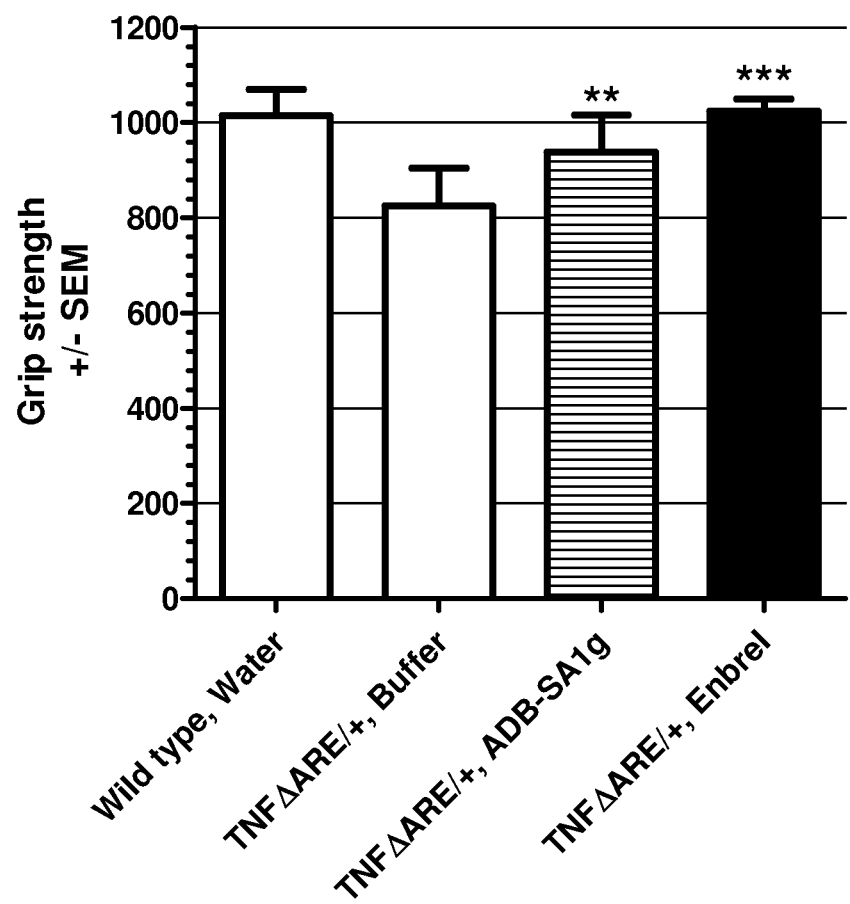
FIG. 15 shows the effects of subcutaneous application of etanercept and of oral application of ADB-SA1g on gripping strength of a transgenic TNFα-overexpressing mice that spontaneously develop arthritis ($TNF^{\Delta ARE/+}$-mice).

Body weight and grip strength measurements were recorded weekly for each mouse. All TNF$^{\Delta ARE/+}$ mice showed normal body weight gain when compared to wild-type littermate control mice. Statistical analysis using ANOVA followed by Newman-Keuls Multiple Comparison Test was performed comparing all groups to TNF$^{\Delta ARE/+}$ vehicle treated group (n=6-8 per group,  p<0.01, * p<0.001). At 11 weeks of age, the vehicle-treated TNF$^{\Delta ARE/+}$ mice displayed significantly reduced grip strength in comparison to wt littermate control mice and etanercept-treated TNF$^{\Delta ARE/+}$ mice. Mice treated orally with ADB-SA1g and mice treated subcutaneously with etanercept displayed comparable, statistically-significant increased grip strength (FIG. 15).

At 11 weeks of age, when the control TNF$^{\Delta ARE/+}$ group had obvious signs of arthritic pathology, mice from all groups were sacrificed and tissue samples from ankle joints were collected and processed for histopathological analysis. Ankle joints were assessed histopathologically. The hind joints of the TNF$^{\Delta ARE/+}$ mice were scored for synovial hyperplasia, existence of inflammatory foci, cartilage destruction, and bone erosion using the scoring scale detailed below:

0=normal
1=mild inflammation in periarticular tissue and/or mild oedema
2=moderate inflammation and pannus formation with superficial cartilage and bone destruction
3=marked inflammation with pannus formation and moderate cartilage and bone destruction (depth to middle zone)
4=severe inflammation with pannus formation and marked cartilage and bone destruction (depth to tidemark).

Figure 16:
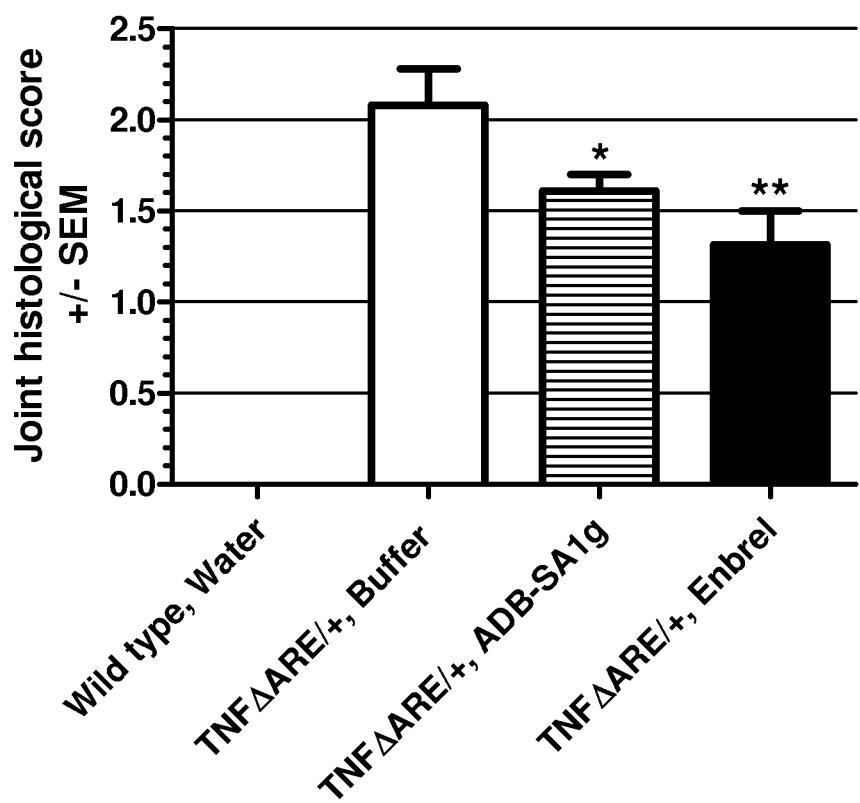
FIG. 16 shows the effects of subcutaneous application of etancercept and of oral application of ADB-SA1g on arthritic score of hind paws of transgenic TNFα-overexpressing mice which spontaneously develop arthritis ($TNF^{\Delta ARE/+}$-mice).
Figure 18A:
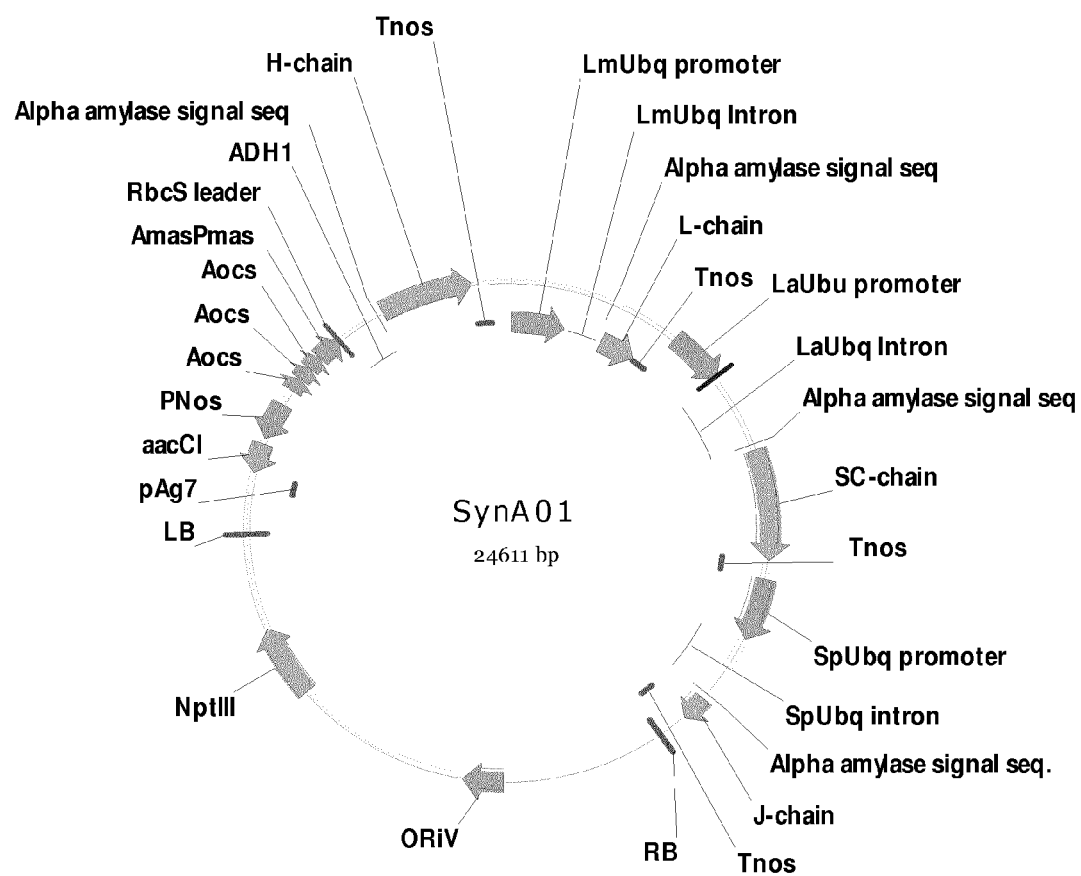
FIGS. 18A through 18C show the structure of vector constructs SynA01 (FIG. 18A), SynA02 (FIG. 18B) and SynA03 (FIG. 18C) used for expression of anti-IL12/23 SIgA in *Lemna* in Example 1.
Figure 18B:
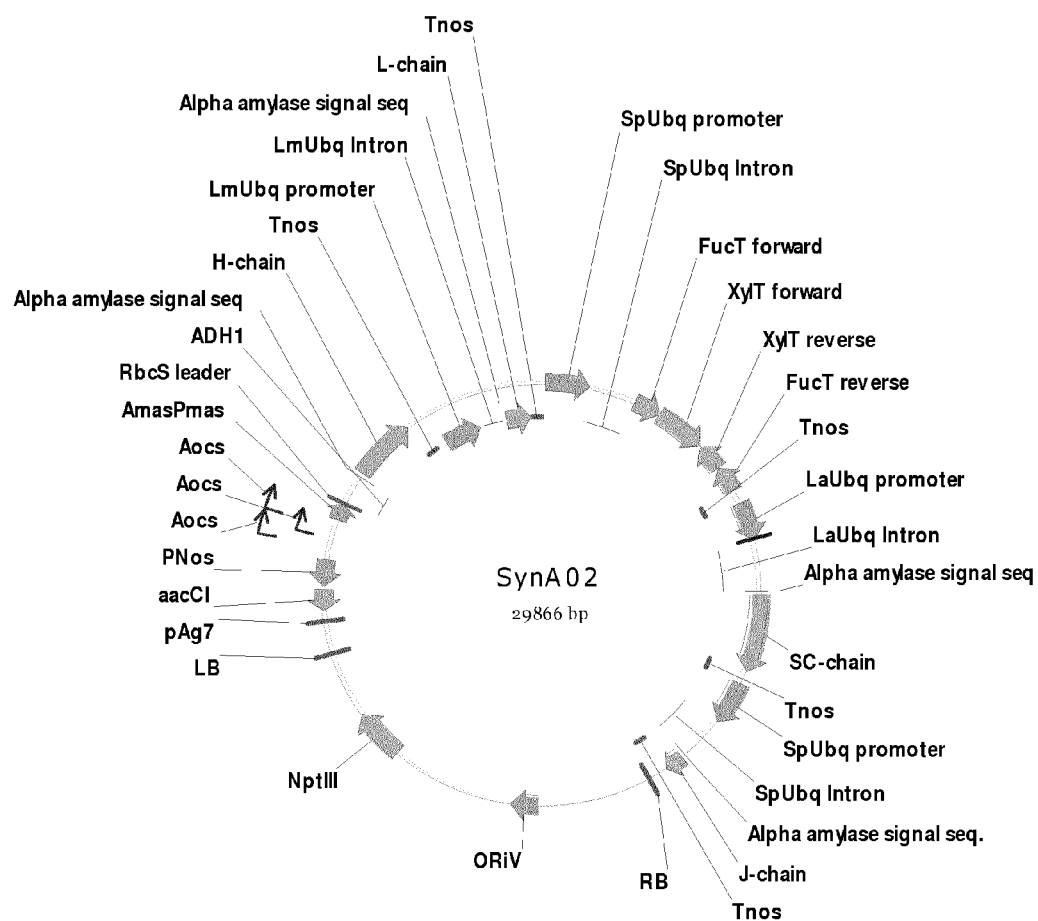
Figure 18C:
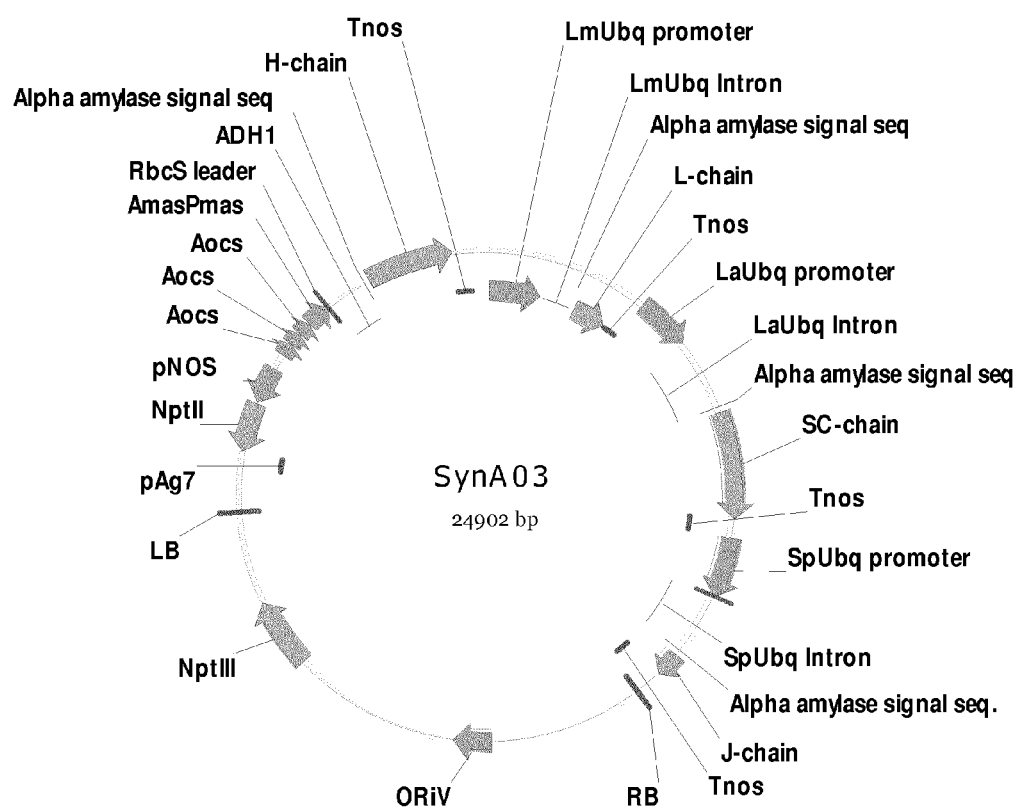

Histopathological analysis of the ankle joints revealed that the vehicle treated $TNF^{\Delta ARE/+}$ mice displayed severe signs of arthritis. Statistical analysis using ANOVA followed by Newman-Keuls Multiple Comparison Test was performed comparing all groups to $TNF^{\Delta ARE/+}$ vehicle treated group (n=6-8 per group, * p<0.05, ** p,0.01). Etanercept-treated animals displayed significantly decreased signs of pathology. Mice treated orally with ADB-SA1g also showed decreased joint inflammation when compared to vehicle-treated $TNF^{\Delta ARE/+}$ mice with an effect comparable to sc etanercept treated animals (FIG. 16).

ANTI-p40 SIGA EXAMPLES

Example 11

Stable Expression of Anti-IL-12/23 Secretory Protein Based on Ustekinumab (UKB-SA1) in *Lemna* a) Construction of Vectors

Synthetic genes were designed for each of the 4 different protein chains of an anti-IL-12/23 secretory IgA. The amino acid sequence of the heavy chain consisted of the rice α-amylase secretion signal (SEQ ID NO:26) joined to the N-terminal amino acid of the variable part of the heavy chain of anti-IL12/23 IgG1 antibody Ustekinumab (Stelara®, CAS number 815610-63-0, SEQ ID NO:37) which in turn is joined to the N-terminal amino acid of the constant part of a human IgA1 heavy chain (SEQ ID NO:10). The amino acid sequence of the light chain consisted of the rice α-amylase secretion signal (SEQ ID NO:26) joined to the N-terminal amino acid of the light chain sequence of Ustekinumab (CAS number 815610-63-0), which combines an anti-IL-12/23 binding variable part (SEQ ID NO:38) with a human κ-light chain constant part (SEQ ID NO:14). The SC-chain consisted of the rice α-amylase secretion signal (SEQ ID NO:26) joined to the N-terminal amino acid of the amino acid sequence of amino acids 19 to 603 of the human polymeric immunoglobulin receptor disclosed in UniProtKB/Swiss-Prot database entry P01833 (SEQ ID NO:21). The J-chain sequence consisted of the rice α-amylase secretion signal (SEQ ID NO:26) joined to the N-terminal amino acid of the amino acid sequence of amino acids 23 to 159 of the human sequence disclosed in UniProtKB/Swiss-Prot database entry P01591 (SEQ ID NO:20).

Genes were designed for each of the four components with *L. minor* preferred codon usage (63-67% GC content). Tables with suitable preferred codon use in Lemnaceae can be found in PCT application WO2005/035768 and in relevant references contained therein. Restriction endonuclease sites were added to allow cloning into *A. tumefaciens* binary vectors. Design of DNA sequences and vector construction was performed by Biolex Therapeutics, Inc., Pittsboro, N.C., USA. DNA sequences were produced by DNA2.0 (Menlo Park, Calif., USA).

The anti-IL-12/23 SIgA (UKB-SA1) was expressed in *L. minor* by transfection via an *A. tumefaciens* binary vector containing DNA sequences encoding all four of the SIgA components: J-chain, SC-chain, H-chain and L-chain. To prepare this vector independent expression cassettes were created containing promoter, DNA sequences encoding the protein and terminator for the J-chain (SEQ ID NO:34), SC-chain (SEQ ID NO:36), H-chain (SEQ ID NO:41) and L-chain (SEQ ID NO:42). The H chain was fused to the modified chimeric octopine and mannopine synthase promoter with *L. gibba* 5' leader from ribulose bis-phosphate carboxylase (RuBisCo) small subunit-1. The L-chain, SC-chain and J-chain genes were fused to high expression Lemnaceae Ubiquitin promoters *L. minor* polyubiquitin promoter (LmUbq), *L. aequinoctialis* polyubiquitin promoter (LaUbq) and *Spirodela polyrhiza* polyubiquitin promoter (SpUbq), respectively. Sequences of these promoters have been disclosed in PCT application WO2007/124186. These expression cassettes were then cloned into a single *A. tumefaciens* transformation vector EC2.2 (a modification of the *A. tumefaciens* binary vector pBMSP3, which is a derivative of pBINPLUS. See Ni, M., Cui, D., Einstein, J., Narasimhulu, S., Vergara, C. E., and Gelvin, S. B. Plant J. 7, 661-676, (1995), van Engelen *Transgenic Res.* 4:288-290 (1995), and Gasdaska et al., *Bioprocessing J.,* 3:50-56 (2003)), with the appropriate restriction sites to create the final transformation vector SynA01 (FIG. 18A). This vector also contained the gentamycin acetyltransferase-3-I gene (aacC1) which confers resistance to gentamycin and allows for selection of transgenic *L. minor* lines, and was used to produce UKB-SA1 with wild-type (unmodified) N- and O-glycosylation.

SynA01 was used to create additional transformation vectors to generate a glycan optimized version of UKB-SA1, further identified as UKB-SA1g0. A chimeric hairpin RNA was used to silence endogenous *L. minor* mRNAs encoding α-1,3-fucosyltransferase (Fuct1, GenBank DQ789145) and β-1,2-xylosyltransferase (Xylt1, GenBank DQ789146). A DNA sequence for this chimeric RNAi molecule was fused to the high expression SpUbq promoter and subsequently moved into the SynA01 vector creating the final transformation vector SynA02 (FIG. 18B). Also the neomycin phosphotransferase II gene (NPTII) was moved into SynA01 replacing aacC1 to produce transformation vector SynA03 (FIG. 6C). This exchange allows for kanamycin selection instead of gentamicin selection of transgenic glycan optimized *L. minor* lines. Further details on procedures for production of glycan optimized proteins in Lemnaceae can be found in PCT applications WO2007/084672, WO2007/084922, WO2007/084926 and in Cox, K. M., Nature Biotechnology 2006, 12: 1591-1597.

b) Transformation of and Expression Using *Lemna*

*Lemna* transformation vectors SynA01, SynA02 and SynA03 were transvected into *A. tumefaciens* strain C58Z707 (Hepburn et al., J. Gen. Microbiol. 1985, 131: 2961-2969) by electroporation. *Agrobacterium* colonies were selected using gentamycin (SynA01 and SynA02) or kanamycin (SynA03) and analyzed for the presence of the appropriate binary vector using a PCR based assay. A single colony was selected for each transformation vector and taken forward into *L. minor* transformation process (as follows).

Partially dedifferentiated *Lemna* tissue (*L. minor* strain 8627) was incubated with *Agrobacterium* harboring the expression cassette plasmid by briefly dipping the tissue into the solution. The tissue was then placed on co-cultivation plates for two days in continuous light at 25° C. Following co-cultivation, the tissue was transferred to antibiotic selection plates and returned to continuous light at 25° C. The tissue was transferred weekly to fresh antibiotic selection plates. Cefotaxime was included in the antibiotic selection plates to eradicate the *Agrobacterium*. Gentamicin was included in these plates to select for transgenic tissue obtained from vectors SynA01 and SynA02 where there is a selectable marker gene included in the transferred genetic cassette which confers gentamycin resistance. Kanamycin was included in plates to select for transgenic tissue from vector SynA03.

UKB-SA1 with unmodified wild-type (WT) glycosylation was obtained by transfection of *L. minor* strain 8627 (Biolex Therapeutics Inc.) with vector SynA01. UKB-SA1g0, having G0 glycans lacking fucose and lacking xylose, was obtained by transfecting *L. minor* strain 8627 with vector SynA02, or by transfection of the N-glycosylation modified *L. minor* strain XF04 (Biolex Inc.) with vector SynA03. Once transformed plants were regenerated (approximately three months) single plants were harvested from the antibiotic selection plates and propagated separately in liquid growth media, without selection antibiotic, for further screening and characterization. Thus several hundred individual transgenic plant lines from each construct were generated. Independent transgenic lines were harvested and clonally propagated in individual harvest jars. For screening of transgenic lines, clonal lines were preconditioned for 1 week at light levels of 150 to 200 $\mu mol/m^2 \cdot s$ in vented plant growth vessels containing SH medium (Schenk R. U. et al., Can. J. Biol. 1972, 50: 199-204) without sucrose. Fifteen to twenty preconditioned fronds were then placed into vented containers containing fresh SH medium, and allowed to grow for two weeks. Tissue samples from each line were collected and frozen for analysis.

To determine SIgA expression, frozen tissue samples were homogenized, centrifuged and the supernatant was removed and screened by an ELISA method using sheep anti-human IgA secretory chain (AbD Serotec catalog #5111-4804-1:1000 dilution) coated plates to capture the SIgA antibody. The samples were then detected using a goat anti-human kappa light chain HRP conjugated antibody (Sigma catalog #A7164-1:2000 dilution). The highest lines from this primary screening were then grown again for two weeks in small research vessels under the optimal growth conditions, the resulting tissue was harvested and the ELISA was performed to determine the percent of the total soluble protein that the SIgA antibody is expressed. The results are summarized in Table 4.

TABLE 4

| Construct | Product | # of lines screened | Highest Expression level |
|---|---|---|---|
| SynA01 in *L. minor* 8627 | UKB-SA1 (WT glycosylation) | 262 | 8.5% TSP |
| SynA02 in *L. minor* 8627 | UKB-SA1g0 (G0 N-glycans) | 164 | 15.1% TSP |
| SynA03 in *L. minor* XF04 | UKB-SA1g0 (G0 N-glycans) | 452 | 11.8% TSP |

Example 12

Isolation and Purification of UKB-SA1 and UKB-SA1g0 Secretory IgA Antibody from *Lemna*

Biomass from transgenic *Lemna* expressing UKB-SA1 or UKB-SA1g0, having variable regions that are the amino acid sequence of the variable regions (antigen binding regions) of Ustekinumab, was homogenized in 50 mM Sodium phosphate, 0.3M Sodium chloride, buffer pH 7.4, at a buffer to tissue ratio of 4:1. An acid precipitation step was performed on the crude extract to remove the enzyme ribulose bis-phosphate carboxylase (RuBisCo) and other plant proteins by adjusting the extract to pH 4.5 using 1M Sodium acetate, pH 2.5. The precipitate was removed by centrifugation of the material at 14,000×g for 30 minutes at 4° C. The supernatant was adjusted to pH 7.4 and filtered to 0.22 μm prior to IMAC chromatography.

IMAC purification: A Chelating Sepharose FF (GE Healthcare prod. Nr. 17-0575-01) column was prepared according to manufacturer instructions (28-4047-39 AC). The column was charged with 3-5 column volumes (cv) of 0.1M Copper sulfate. Excess copper was washed with 3-5 cv of double distilled water. The column was equilibrated with 3-5 cv of PBS buffer (50 mM Sodium phosphate, 0.15M Sodium chloride, pH 7.4); 3-5 cv of 0.1M Sodium acetate, pH 4.0 buffer; 3-5 cv PBS buffer with 0.5M Imidazole; and 3-5 cv PBS buffer.

The supernatant was loaded on the column Approximately 3.8 mg SIgA/ml resin was loaded on columns of up to 350 ml chelating Sepharose. Non-binding material was washed from the column with 10 cv PBS buffer, 10 cv of 0.1M Sodium acetate, pH 4.0 buffer, and 10 cv PBS buffer. The product was eluted from the column using 10 cv of PBS buffer containing 0.075 M Imidazole (a gradient of 0-0.075 M imidazole was also used but did not lead to improved results). The fractions containing the secretory IgA antibodies were pooled.

The column was regenerated by removing copper using a 0.2M EDTA, 0.3M sodium chloride solution, followed by treatment with 0.1N NaOH.

SEC purification: Material obtained by IMAC chromatography was further purified on a Sephacryl 5300 HR column. The column was equilibrated with 2 cv of PBS buffer at a flow rate of 0.5 ml/min. The IMAC eluate was concentrated 3× using ultra filtration (e.g., using a 5- or 30 kDa regenerated cellulose (hydrosart) membrane) by using, for example, a spin filter (Vivaspin 15R) or a UF cassette (Sartorius 305 144 59 01 E). Typically, a concentration of 5-7 mg/ml and feed volume of 15-20 ml was used for a 360 ml column. The feed was applied using an AKTA purifier at 0.5 ml/min Elution was performed with at least 2 column volumes of PBS buffer at room temperature and a flow rate of 0.5 ml/min Fractions were collected and sufficiently pure fractions were pooled.

Figure 19:
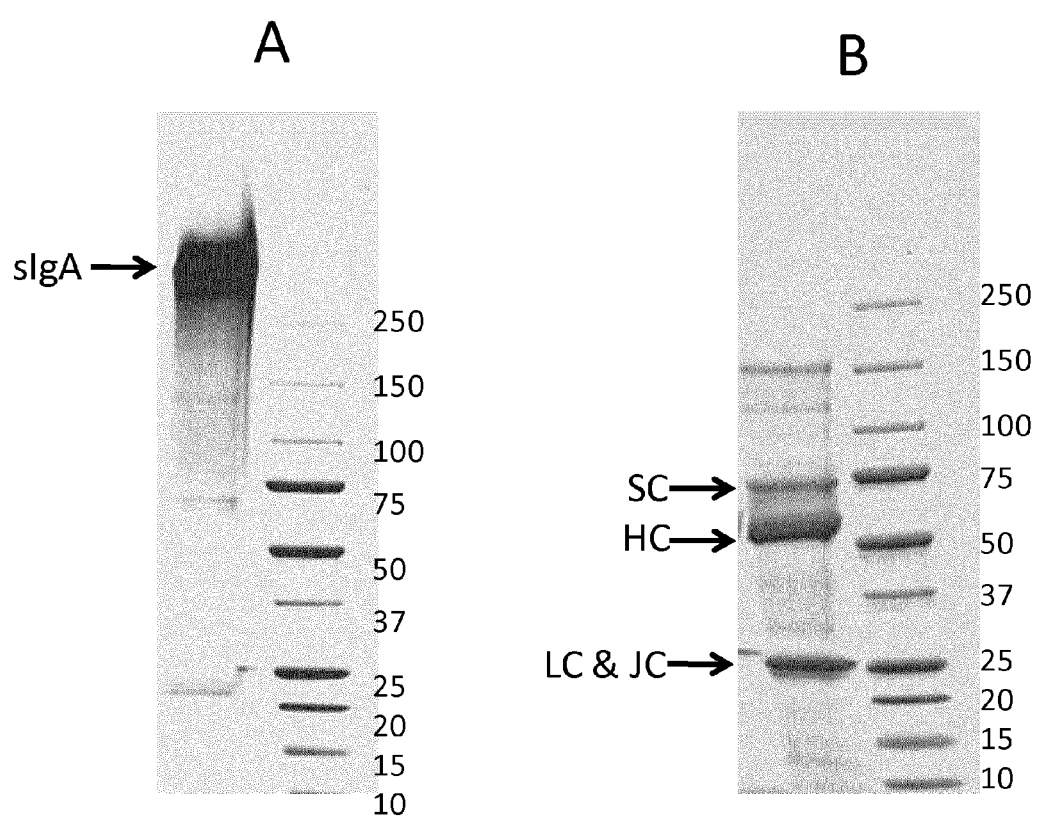
FIG. 19 shows reducing and non reducing gels of an anti-IL-12/23 SIgA according to the invention, having ustekinumab variable regions and being produced in *Lemna*. The A gel shows non-reducing SDS-PAGE analysis demonstrating expression of complete SIgA. The B gel shows reducing SDS-PAGE analysis.

Results of non-reducing and reducing SDS-PAGE analyses of purified material obtained from *Lemna* transfected with construct SynA01 are shown in FIG. 19 as gels A and B, respectively.

Some batches of material produced by the purification method described above were further purified using affinity chromatography using CaptureSelect human IgA (BAC).

Using an Akta Explorer 10 system a column loaded with 30.9 ml Capture Select IgA (BAC) was equilibrated using 3 column volumes (CV) 20 mM Tris pH 7.0 buffer at a flow rate of 5 ml/min A solution containing 75.9 mg UKB-SA1 in Tris buffer pH 7.0 was loaded on the column at a flow rate of 2.5 ml/min After a wash step with 5 CV of 20 mM Tris buffer pH 7.0 at 5 ml/min the product was eluted with 5 CV of 20 mM Tris buffer pH 7.0 containing 3.5 M $MgCl_2$ at 5 ml/min.

The eluate was first dialyzed twice against 5 L 20 mM Tris buffer pH 7.0 using snakeskin 10 kDa dialysis tubing for at least 2 hours, followed by dialysis against 5 L PBS puffer pH 7.4 for at least 2 hours. The solution was concentrated using a stirred cell (Amicon 8200, Millipore, overhead pressure 30 Psi) with 30 kDa regenerated cellulose membrane filter (Millipore) to a final concentration of approximately 1 mg/ml. The obtained product was further purified using SEC purification as described previously. Glycosylation modified product UKB-SA1g0 was purified using the same method.

No substantial differences were observed in purification of the two glycosylation forms, wild-type UKB-SA1 and UKB-SA1g0.

Example 13

Binding of UKB-SA1 and UKB-SA1g0 to IL12

The binding of purified anti-IL-12/23 SIgA, with variable regions taken from Ustekinumab and produced in *Lemna* as in Examples 11 and 12, to IL-12 was determined. The binding of both UKB-SA1 and UKB-SA1g0 products were determined in comparison to ustekinumab (STELARA®) and colostral SIgA. Plates were coated with IL-12 (Abcam, AB52086) 1 µg/ml. Detection of bound UKB-SA1/UKB-SA1g0 (secretory IgA) and ustekinumab (IgG1) antibodies was performed using a 1:1500 fold dilution of anti human kappa chain antibody (Abbiotec, cat. no.250987), 100 µl per well, for one hour at RT, washing 3 times, 30 seconds with 200 µl PBS/0.05% Tween with shaking, followed by incubation with a 1:1500 fold dilution of donkey anti mouse HRP conjugated (Emelca biosciences, MS3001), 100 µl per well, for one hour at RT.

The UKB-SA1, UKB-SA1g0 and ustekinumab antibodies all bound with high affinity to IL-12 under the conditions of this assay. For UKB-SA1 and UKB-SA1g0 antibodies, binding occurred independent of the type of glycosylation. Colostral SIgA had minimal to no binding to IL-12.

Example 14

Proteolytic Stability of UKB-SA1 and UKB-SA1g0

The stability of UKB-SA1 and UKB-SA1g0 with antigen binding regions having the amino acid sequence of ustekinumab antigen binding regions (i.e., the variable heavy and light chains), produced in *Lemna*, was determined in simulated intestinal fluid (SIF, 0.05M phosphate buffer pH 6.8 containing 10 mg/ml pancreatin). Both the form with wild-type *Lemna* glycosylation obtained with vector SynA01, and the G0 glycosylation variant obtained with vector SynA02 were analysed. Stability was compared to ustekinumab (IgG1) and to aspecific human colostral SIgA which was purified to contain only kappa light chains and α-1 heavy chains.

90 µl of a 1 mg/ml solution of the material to be tested was added to 810 µl of SIF at 37° C. 50 µl samples were drawn at T=0, 5, 15, 30, 60 and 120 min and immediately frozen in liquid nitrogen. Samples were analyzed by non-reducing SDS-Page gel electrophoresis. Briefly; 17 µl of a 0.15M solution of iodoacetamide in LDS sample buffer was added to each of the frozen samples. Samples were thawed and applied to Criterion Tris-HCl gel (12.5%, 18 well, 30 µl comb (Biorad, 345-0015). After electrophoresis gels were treated with Krypton protein stain and analyzed. Stability of the samples was qualitatively assessed visually. Results are shown in FIG. 20 where gel A is the UKB-SA1 (labeled SynA01-WT in FIG. 20) and gel B is UKB-SA1g0 (labeled SynA02-G0 in FIG. 20).

Both UKB-SA1 and UKB-SA1g0 of exhibited a stability that was comparable to natural human colostral SIgA. The IgG1 antibody ustekinumab degraded under these conditions at such a high rate that detection at T=0 was not possible.

Example 15A

Inhibition of IL-12/23 in Dendritic Cells

To demonstrate inhibition of endogenous produced p40/IL12/IL23 by UKB-SA1 or UKB-SA1g0 versus ustekinumab (IgG1) or non-specific SIgA (polyclonal colostral SIgA), in vitro experiments were performed with dendritic cells and T cells. Monocytic cells were isolated from human donor blood and stimulated with lipopolysccharide (LPS) and the cells were differentiated into mature dendritic cells. The stimulation with LPS and resulting differentiation was performed in the presence of a SIgA antibody of the invention, Ustekinumab, polyclonal colostral SIgA, or without any added antibody (i.e., LPS only).

In more detail, the experiments were performed as follows. Human dendritic cells (DCs) were obtained from isolated monocytes from buffy coats. The adherent monocytes were cultured in synthetic X-VIVO 15 medium (Lonza, Cat. No. BE04-418Q) supplemented with 2% of AB human serum (Sigma, Cat. No. H4522), 450 U/ml GM-CSF (Miltenyi Biotec, Cat. No. 130-093-867) and 300 U/ml IL-4 (Miltenyi Biotec, Cat. No. 130-093-924) as growth and differentiation factors, respectively, for 6 days to obtain immature DCs. After one week, immature DCs ($5 \times 10^3$) were activated for 24 hours with 1 µg/ml LPS (Invivogen, Cat. No. tlrl-pelps) in the presence of different concentrations UKB-SA1, UKB-SA1g0, or control antibodies to induce DC maturation. IL12/IL23 concentration in culture medium was measured by ELISA according to the manufactures' instructions (BD OptEIA, Cat. No. 555171).

Figure 21A:
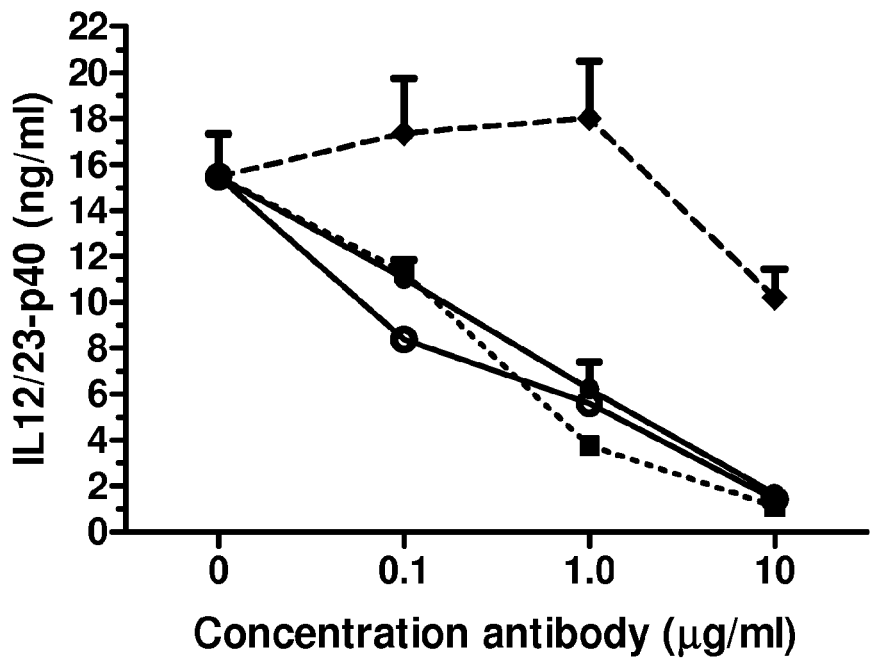
FIGS. 21A and 21B show the results of inhibition of IL-12/23 (p40) production by LPS-stimulated Dendritic Cells from Examples 15A and 15B, respectively.

The results are represented in FIG. 21A where open circle is UKB-SA1; closed circle is UKB-SA1g0; Diamond is Colostral SIgA; and Square is ustekinumab. Data are means (+/−SEM) of 3 experiments. Both UKB-SA1 and UKB-SA1g0 inhibited endogenous produced p40/IL12/IL23 by dendritic cells. Both UKB-SA1 and UKB-SA1g0 had a similar efficacy and potency as Ustekinumab in this regard.

Example 15B

Inhibition of IL-12/23 in Dendritic Cells

Similar to above, inhibition of IL-12/23 in dendritic cells was measured but at a fixed concentration of the antibody. Human dendritic cells (DCs) were obtained from isolated monocytes from buffy coats. The adherent monocytes were cultured in synthetic X-VIVO 15 medium (Lonza, Cat. No. BE04-418Q) supplemented with 2% of AB human serum (Sigma, Cat. No. H4522), 450 U/ml GM-CSF (130-093-867, Miltenyi Biotec) and 300 U/ml IL-4 (Miltenyi Biotec, Cat. No. 130-093-924) as growth and differentiation factors, respectively, for 6 days to obtain immature DCs. After one week, immature DCs ($5 \times 10^3$) were activated for 24 hours with 1 µg/ml LPS (Invivogen, Cat. No. tlrl-pelps) in the presence of 10 µg/ml UKB-SA1, UKB-SA1g0, or control antibodies to induce DC maturation. IL12/IL23 concentration in culture medium was measured by ELISA according to the manufactures' instructions (BD OptEIA, Cat. No. 555171).

Figure 21B:
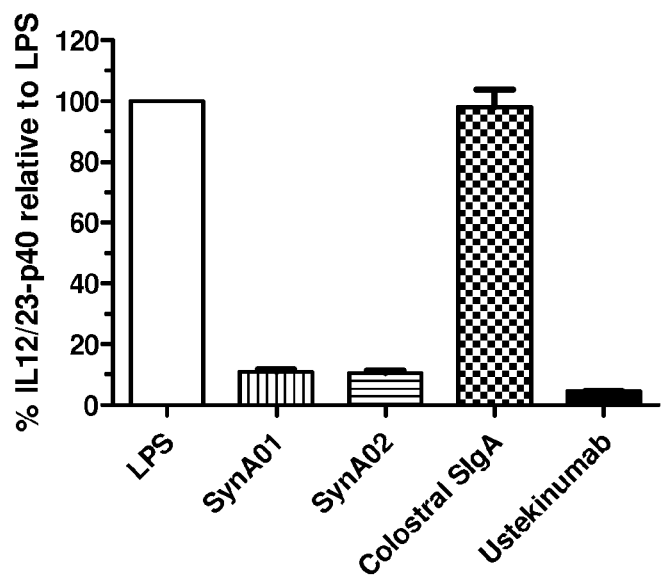

The results are represented in FIG. 21B. Both UKB-SA1 (labeled SynA01 in FIG. 21B) and UKB-SA1g0 (labeled SynA02 in FIG. 21B) inhibited endogenous produced p40/IL12/IL23 by dendritic cells to the same extent as ustekinumab.

Example 15C

Inhibition of IL-12/23 in Dendritic Cells and T Cells

To determine if other "intrinsic" properties were affected by the antibodies, dendritic cells were co-cultured with T-cells. The crosstalk between these cells, which might result in a change of phenotype of the dendritic cells, or cytokine secretion profile of the T-cells was examined. DCs were stimulated with LPS for 6 h; afterwards DCs were washed twice in PBS and in the presence of 10 µg/ml of UKB-SA1, UKB-SA1g0 or control antibodies cultured with allogeneic T cells. The allo-response was tested in a mixed lymphocyte reaction; allogeneic T cells ($10^5$ cells) were co-cultured in triplicate with differently treated DCs ($5*10^3$) in a 96-well round bottom plate, in 200 µl of medium (X-VIVO 15+2% HS). For T helper polarisation T lymphocytes supernatants were collected at day 4 and T helper specific cytokine IFNγ was analysed by ELISA (BD OptEIA, Cat. No. 555142), according to the manufacturers' instructions.

Figure 21C:
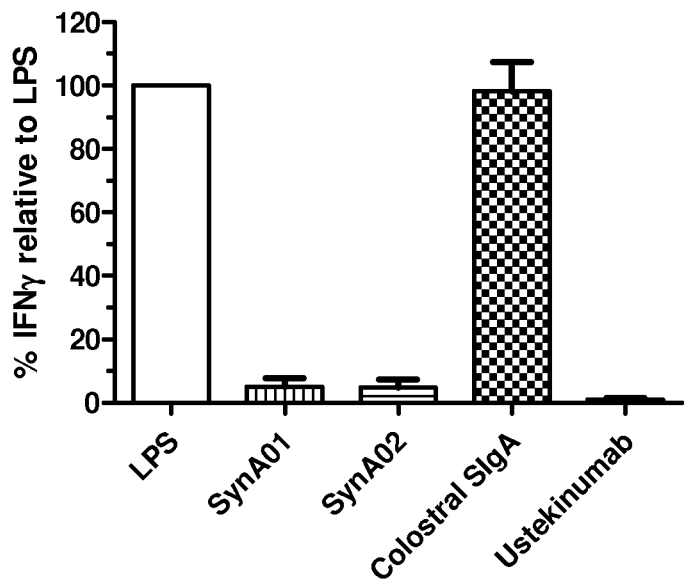
FIGS. 21C and 21D show the results of inhibition of production of IFNγ by co-cultured dendritic cells and T-Cells from Examples 15C and 15D, respectively.

The results are represented in FIG. 21C. UKB-SA1 (labeled SynA01 in FIG. 21C) and UKB-SA1g0 (labeled SynA02 in FIG. 21C) blocked the IFNγ secretion by co-cultured DCs and T-cells to the same extent as Ustekinumab, indicating an inhibition of proinflammatory T helper-1 cells.

Example 15D

Inhibition of IL-12/23 in Dendritic Cells and T Cells

Similar to above, the antibodies were applied in fixed concentrations to the DC and T cells. DCs were stimulated with LPS for 6 h; afterwards DCs were washed twice in PBS and in the presence of 10 µg/ml of UKB-SA1, UKB-SA1g0 or control antibodies cultured with allogeneic T cells. The allo-response was tested in a mixed lymphocyte reaction; allogeneic T cells ($10^5$ cells) were co-cultured in triplicate with differently treated DCs ($5*10^3$) in a 96-well round bottom plate, in 200 µl of medium (X-VIVO 15+2% HS). For T helper polarisation T lymphocytes supernatants were collected at day 4 and T helper specific cytokine IL-10 was analysed by ELISA (eBioscience Cat. No. 88-7106-88), according to the manufacturers' instructions.

Figure 21D:
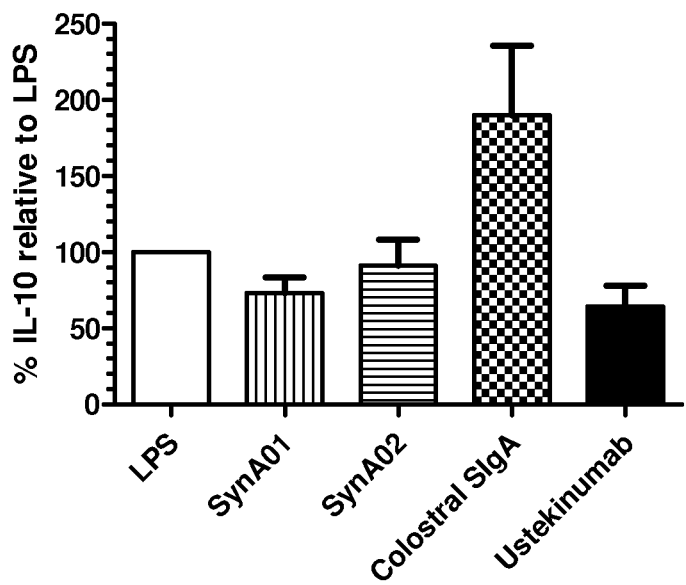

The results are represented in FIG. 21D. UKB-SA1 (labeled SynA01 in FIG. 21D) and UKB-SA1g0 (labeled SynA02 in FIG. 21D) had no effect on the IL-10 secretion by co-cultured DCs and T-cells.

Example 16

Pharmacokinetics of UKB-SA1g0

Serum concentrations of UKB-SA1g0 after oral and intravenous administration were determined UKB-SA1g0 was administered to C57Bl/6 mice (200 µg for intravenous, 400 µg oral) and blood samples were taken by orbital bleeding at different time points. UKB-SA1g0 was measured by an in-house constructed ELISA. A goat anti-human kappa light chain antibody (SouthernBiotech, Cat. No. SBA 2060-02) was used for coating of the plates, and a goat anti-human IgA antibody (SouthernBiotech, Cat. No. SBA 2050-05) for detection. The minimum detection limit of the ELISA is 5 ng/ml.

Figure 22:
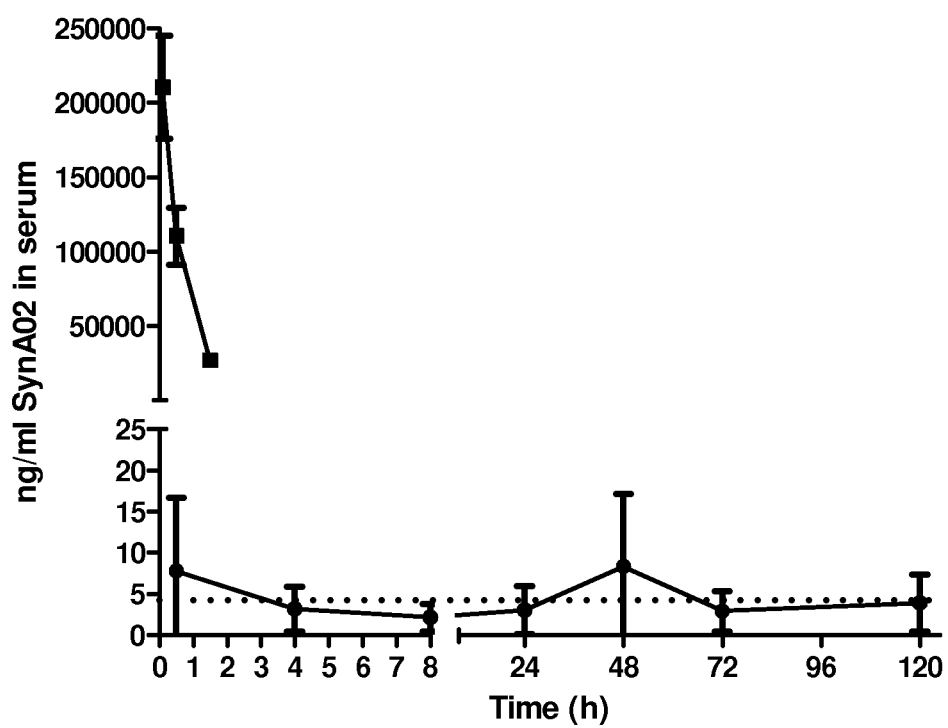
FIG. 22 shows the serum concentrations of SynA02 (UKB-SA1g0) after oral (circle) and intravenous (square) administration as described in Example 16.

The results are represented in FIG. 22 wherein circle shows oral administration and square shows intravenous administration. Dotted line at 5 ng/ml depicts the detection limited of the ELISA used for quantification. Data are mean+/−SD of 2 representative mice. UKB-SA1g0 (labeled SynA02 in FIG. 22) is rapidly cleared from circulation after intravenous injection and very little (if any) exposure was measured after oral administration.

Example 17

In Vivo Administration of SIgA and IgG Anti-IL12/23 Pharmacokinetics

Using in vivo imaging of fluorescent labeled antibodies, images of thoracic and abdominal region of mice can reveal distribution of the antibody over time. UKB-SA1 was conjugated with either Alexa Flour 647 (Molecular probes), or DyLight 755 (ThermoFisher) according manual instructions. The dye can be detected as a fluorescent signal with the Maestro in vivo imaging system (Cambridge Research & Instrumentation). Fluorescent conjugated antibodies (100 µg/mice) were administered orally or intraperitoneally. Mice were anaesthetized with Xylamine/Ketamine before examination with the Maestro system in order to immobilize animals during picture taking procedure. Then mice were analyzed and pictures of the distribution of the fluorescence conjugated UKB-SA1 were taken at different time points indicated at the experimentally setup. After that background fluorescence were subtracted by software.

Figure 23:
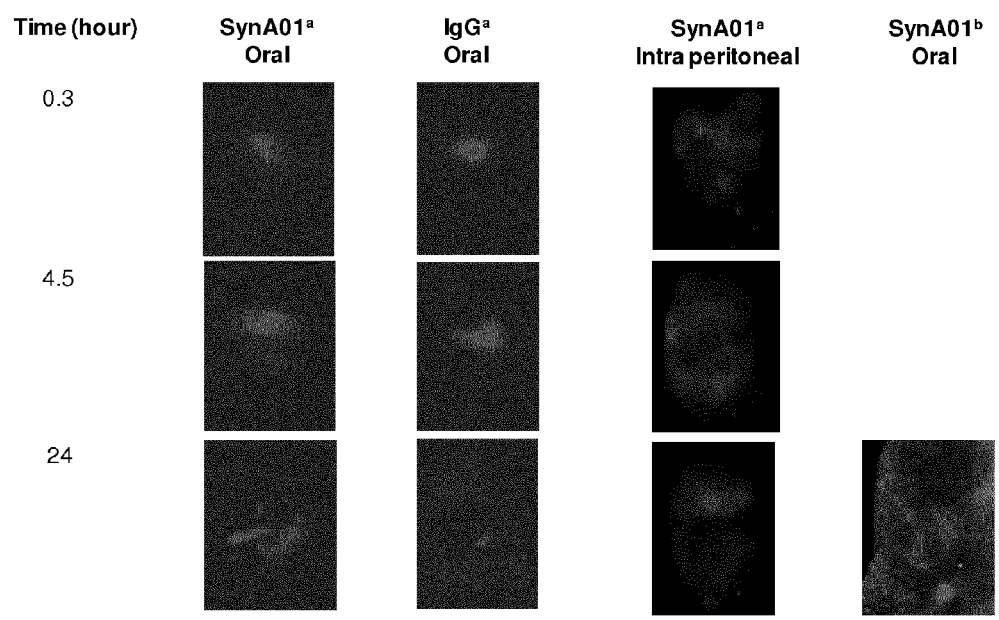
FIG. 23 shows in vivo imaging of fluorescent labeled SynA01 (UKB-SA1) and ustekinumab antibodies in the thoracic and abdominal region of mice as described in Example 17.

The results are represented in FIG. 23 wherein the first three columns ($^a$) correspond to the DyLight 775 conjugate and the fourth column ($^b$) is the UKB-SA1 Alexa Flour 647 conjugate. First hours after oral administration fluorescent conjugated antibodies UKB-SA1 (labeled SynA01 in FIG. 23) and IgG1 Ustekinumab (labelled IgG in FIG. 23) are present in thoracic area of mice, probably the stomach, whereas after 24 hours a clear signal of UKB-SA1, but not IgG1, is present in the abdominal region (intestine) of the mice. Intraperitoneal administration results in a diffuse thoracic and abdominal signal after 24 hours.

Example 18

Distribution In Vivo after Oral Administration

Immunohistochemistry on cryo-sections of mice distal colon, 48 hours after oral administration of antibody were assessed. Antibodies (100 µg/mouse) were administered orally and after 48 hours animals were sacrificed and intestinal tract isolated. Cry-section were stained with anti-SC-chain antibody (Santa Cruz, Cat. No. sc20656) for detection of antibodies containing a human secretory chain. This antibody does not cross-react with mouse secretory chain. As secondary antibody goat-anti-rabbit conjugated with Cy3-red antibody (Jackson Immunoresearch, Cat. No. 111-166-045) was used.

Figure 24:
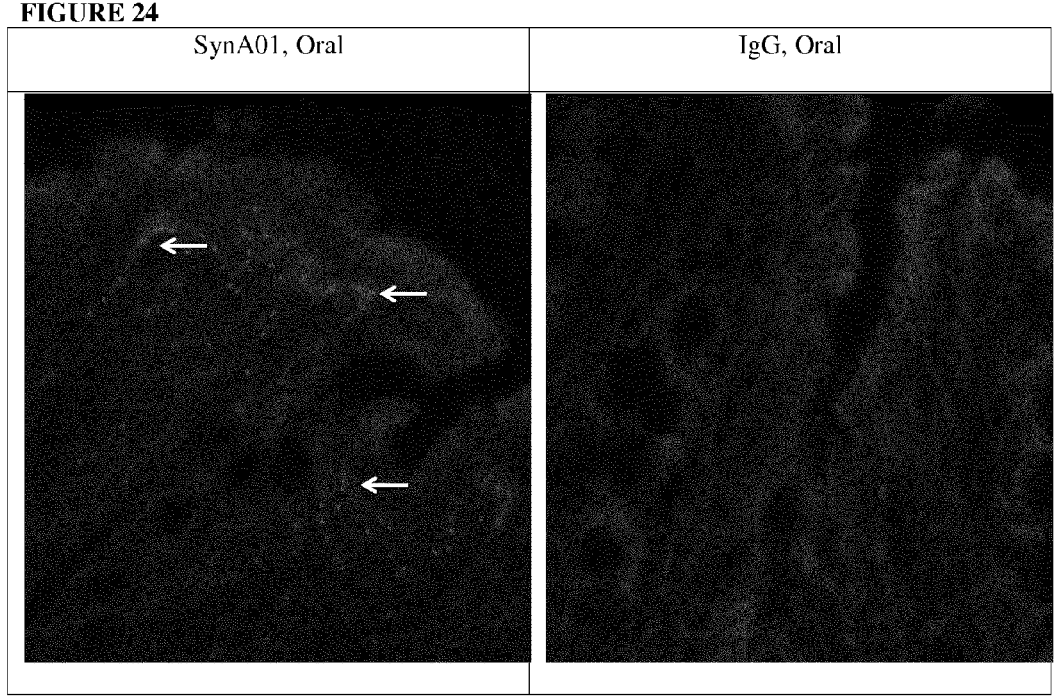
FIG. 24 shows immunohistochemistry on cryo-sections of mice distal colon after administration of SynA01 (UKB-SA1) and ustekinumab antibodies as described in Example 18.

The results are represented in FIG. 24 where the left side is UKB-SA1 (labeled SynA01 in FIG. 24) and the right side is IgG1 Ustekinumab (labeled IgG in FIG. 24). UKB-SA1 is present in cells of the sub mucosal layer of the distal colon as indicated by the bright spots in the vicinity of the white arrows. No IgG1 is indicated as being present in the distal colon cells.

Example 19

Efficacy of UKB-SA1 and UKB-SA1g0 in In-Vivo Animal Models of IBD

Heparinized blood was obtained from healthy donors (buffy coats). PBMC's were isolated from buffy coats by Ficoll-Paque 1.077 g/ml (PAA Laboratories GmbH) density centrifugation and cells were washed with 1×PBS before reconstitution. NOD.CB17-Prkdcscid/J γc−/− (NOD-SCID-IL2 receptor deficient) mice 4 to 8 weeks of age were reconstituted with $30 \times 10^6$ human cells. Three weeks after reconstitution animals were pre-treated orally 5 times a week (not in weekend) with PBS control, UKB-SA1 (100 µg/mouse), UKB-SA1g0 (100 µg/mouse), or 3 times per week subcutaneous with Ustekinumab (100 µg/mouse). Start of pre-treatment is t=0. At day t=7 reconstituted mice were treated with 2% dextran sulfate sodium (DSS) in drinking water to induce inflammation symptoms in intestine. First signs of inflammation can be seen at day 10-12, together with declined body weight. With mini-endoscopic system an analysis of the status of disease was performed. Briefly, a mini-endoscope (1.9 mm outer diameter) was introduced via the anus and the colon was carefully inflated with an air pump. Endoscopic pictures obtained are of high quality and allow the monitoring and grading of inflammation. Thereafter, endoscopic scoring of five parameters from 0-3 (1; translucent structure, 2; granularity, 3; fibrin, 4; vascularity, and 5; stool) resulting in the overall score from 0 (no change) to 15 (severe colitis) was performed. Typically, after one week exposure to DSS the symptoms are so strong that mice need a resting period to recover. At day t=16 the experiment was terminated and clinical score analyzed.

Figure 25A:
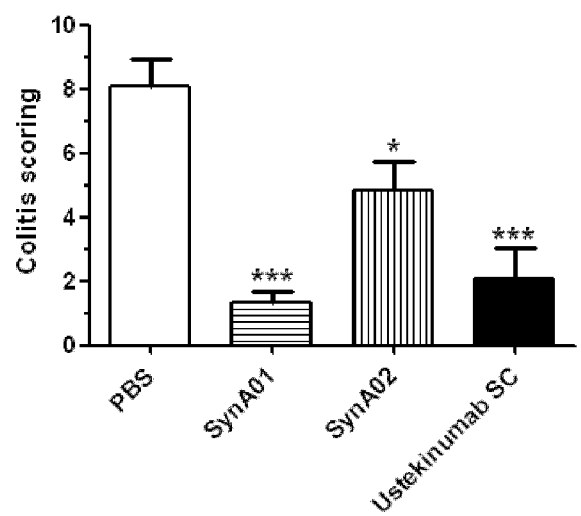
FIGS. 25A and 25B show the efficacy of anti-IL12/23 SIgA in in vivo animal models of IBD as described in Example 19.
Figure 25B:
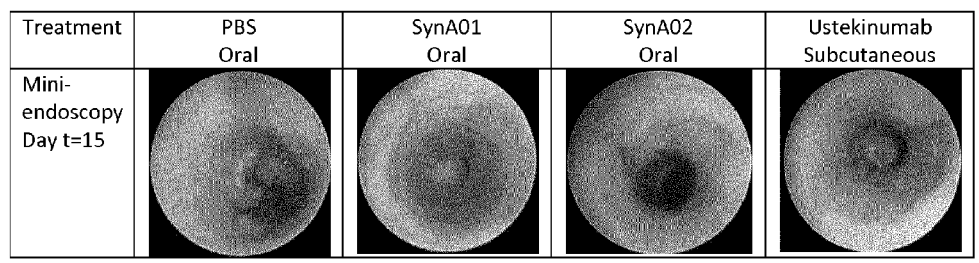

The results are depicted in FIGS. 25A and B. Oral treatment with UKB-SA1 (labeled SynA01 in FIGS. 25A and 25B) and UKB-SA1g0 (labeled SynA02 in FIGS. 25A and 25B), as well as subcutaneous treatment with Ustekinumab, significantly inhibited DSS-induced inflammatory bowel disease in humanized-scid mice. Statistical analysis: ANOVA followed by Dunnett's Multiple Comparison test, all groups were compared to PBS control group. * $p<0.05$, *** $p<0.001$, n=7 mice per group. FIG. 25B depicts a representative mini-endoscopic picture of the colitis score at day t-15.

Example 20

Efficacy of UKB-SA1 and UKB-SA1g0 in Human Psoriatic Skin Biopsies

The activity of SIgA anti-p40 on gene expression was evaluated for a limited number of selected genes in skin explants of psoriatic lesions in vitro. Psoriatic cutaneous lesions can be maintained in culture up to 8 days without significant changes in their psoriatic phenotype. Two punch biopsies of 4 mm were obtained from 7 psoriasis patients (volunteers). Time of evolution of the lesion varied between 1 and 12 months. The two biopsies from each patient were cut in half making four 2 mm biopsies. From one punch, one 2 mm biopsy was tested with vehicle and the other with UKB-SA1. From the other punch, one 2 mm biopsy as tested with UKB-SA1g0 and the other with ustekinumab. UKB-SA1 and UKB-SA1g0 were tested at equimolar concentrations of 14 µg/ml and Ustekinumab was tested at 10 µg/ml. The biopsies, medium, and antibody as appropriate were combined in a 24 well plate (800 µl) for 8 days with the medium changed every 2-3 days. After 8 days of culture, the skin biopsies were frozen in liquid nitrogen and then evaluated. Genes were evaluated by RTPCR: Beta-defensin 4, Keratin 16, Interleukin-10, and GAPDH (house-keeping gene). Keratin 16 and β-Defensin 4 are proteins expressed in epithelial tissue and related to skin diseases. Down-regulation of these markers anticipate clinical efficacy of anti-inflammatory treatment in the clinic. Gene expression in treated biopsies was normalized to house-keeping gene GAPDH according to the formula 1,8e (Ct GADPH-Ct gene of interest)×10000 (Ct=cycle threshold time). After normalization, gene expression of gene of interest was compared to gene expression in vehicle-treated biopsies.

The results are represented in the table below:

| Patient No. | Time of evolution of the lesion (months) | SynA01 | | SynA02 | | Ustekinumab | |
|---|---|---|---|---|---|---|---|
| 2 | 12 | K16 | ++ | K16 | − | K16 | = |
| | | BF | +++ | BF | = | BF | +++ |
| | | IL10 | −−− | IL10 | −− | IL10 | ++ |
| 5 | 12 | K16 | = | K16 | + | K16 | = |
| | | BF | +++ | BF | +++ | BF | ++ |
| | | IL10 | − | IL10 | − | IL10 | = |
| 4 | 6 | K16 | + | K16 | +++ | K16 | +++ |
| | | BF | +++ | BF | + | BF | +++ |
| | | IL10 | + | IL10 | + | IL10 | = |
| 3 | 3 | K16 | = | K16 | + | K16 | = |
| | | BF | = | BF | −− | BF | −− |
| | | IL10 | ++ | IL10 | + | IL10 | = |
| 7 | 2 | K16 | +++ | K16 | +++ | K16 | +++ |
| | | BF | −−− | BF | −−− | BF | −−− |
| | | IL10 | −−− | IL10 | −−− | IL10 | −−− |
| 6 | 1 | K16 | −−− | K16 | ++ | K16 | −− |
| | | BF | −− | BF | +++ | BF | −−− |
| | | IL10 | +++ | IL10 | +++ | IL10 | − |
| 1 | 1 | K16 | −− | K16 | − | K16 | − |
| | | BF | −− | BF | +++ | BF | − |
| | | IL10 | ++ | IL10 | +++ | IL10 | − |

Legend: Beta-defensin 4 (BF4), Keratin 16 (K16), Interleukin 10 (IL-10) No regulation (0-10% difference in gene expression) is "="; Up-regulated (11-25% difference in gene expression) is +; 26-50% is ++; and >51% is +++. Down-regulated (11-25% difference in gene expression) is −; 26-50% is −−; and >51% is −−−.

Time of evolution of the lesion appears to be relevant for the activity of antip40 antibodies as UKB-SA1, UKB-SA1g0, and ustekinumab have activities in patients, especially those with less than 6 months of evolution of the lesion. Gene expression of Keratin 16 and Beta defensin 4 (two) were reduced in young lesions (1-3 month) by SynA01, SynA02 and ustekinumab, indicating reduced epithelial activity and a treatment effect.

In these young lesions, Interleukin-10 expression was increased only by UKB-SA1 and UKB-SA1g0, but not by ustekinumab, indicating an additional anti-inflammatory cytokine response of SIgA's compared to an IgG antibody.

Each of the patents, patent applications, and journal articles mentioned above are incorporated herein by reference in their entirety. The invention having been described it will be obvious that the same may be varied in many ways and all such modifications are contemplated as being within the scope of the invention as defined by the claims appended hereto.

The invention claimed is:

1. A monoclonal secretory IgA antibody, which binds to and neutralizes a human proinflammatory cytokine, wherein said antibody comprises:
   (a) a light chain constant region having the sequence of SEQ ID NO:14,
   a heavy chain variable region having the sequence of SEQ ID NO:4, and
   a light chain variable region having the sequence of SEQ ID NO:5; or
   (b) a light chain constant region having the sequence of SEQ ID NO: 14, a heavy chain variable region having the sequence of SEQ ID NO: 37, and
   a light chain variable region having the sequence of SEQ ID NO: 38.

2. The antibody according to claim 1, wherein said antibody comprises:
   (a) a light chain constant region having the sequence of SEQ ID NO:14;
   (b) a heavy chain variable region having a sequence of SEQ ID NO:4; and
   (c) a light chain variable region having a sequence of SEQ ID NO:5.

3. The antibody according to claim 1, wherein said antibody comprises a human secretory chain having the sequence of SEQ ID NO:21.

4. The antibody according to claim 1, wherein said antibody comprises a human J-chain having the sequence of SEQ ID NO:20.

5. The antibody according to claim 1, wherein said proinflammatory cytokine is TNF-α and wherein said antibody neutralizes TNF-α by at least 50%.

6. The antibody according to claim 5, wherein said proinflammatory cytokine is TNF-α and wherein said antibody neutralizes TNF-α by least 98%.

7. A pharmaceutical composition comprising a therapeutically effective amount of a monoclonal secretory IgA antibody, which binds to and neutralizes a human proinflammatory cytokine, wherein said antibody comprises:
   (a) a light chain constant region having the sequence of SEQ ID NO:14,
   a heavy chain variable region having the sequence of SEQ ID NO:4; and
   a light chain variable region having the sequence of SEQ ID NO:5; or
   (b) a light chain constant region having the sequence of SEQ ID NO: 14,
   a heavy chain variable region having the sequence of SEQ ID NO: 37, and
   a light chain variable region having the sequence of SEQ ID NO: 38; and
   at least one pharmaceutically acceptable excipient.

8. The composition of claim 7, wherein the composition comprises about 0.01 to 1000 mg of the antibody.

9. The composition of claim 7, wherein the composition comprises a plurality of secretory IgA antibodies.

10. The composition of claim 9, wherein said plurality of secretory IgA antibodies contains at least about 30% G0 glycans.

11. The composition of claim 10, wherein said G0 glycans lack fucose and xylose residues.

12. The composition of claim 7, wherein said plurality of secretory IgA antibodies contains at least at least about 25% high-mannose glycans.

13. The composition of claim 12, wherein said high-mannose glycans are selected from the group consisting of Man5, Man6, Man7, Man8, and Man9.

14. The composition of claim 9, wherein said plurality of secretory IgA antibodies contains at least 70% of G0 glycans and high-mannose glycans relative to the total amount of N-glycans in the plurality of secretory IgA antibodies.

15. The composition of claim 7, wherein the composition can be administered to a human by oral, rectal, buccal, topical, parenteral, or subcutaneous administration.

16. The composition of claim 7, wherein the composition comprises less than 10% of dimer IgA.

17. The composition of claim 16, wherein the composition comprises less than 10% of monomeric IgA.

18. A monoclonal secretory IgA antibody, which binds to and neutralizes a human proinflammatory cytokine, wherein said antibody comprises:
(a) a heavy chain variable region having the sequence of SEQ ID NO:4 and a light chain variable region having the sequence of SEQ ID NO:5; or
(b) a heavy chain variable region having the sequence of SEQ ID NO:37 and a light chain variable region having the sequence of SEQ ID NO:38.

19. A monoclonal secretory IgA antibody, which binds to and neutralizes a human proinflammatory cytokine, wherein said antibody comprises:
(a) a light chain constant region having the sequence of SEQ ID NO:14, or minor variations thereof, a heavy chain variable region having the sequence of SEQ ID NO:4, and a light chain variable region having the sequence of SEQ ID NO:5; or
(b) a light chain constant region having the sequence of SEQ ID NO: 14, or minor variations thereof, a heavy chain variable region having the sequence of SEQ ID NO: 37, and a light chain variable region having the sequence of SEQ ID NO: 38; and
wherein the minor variations are no more than 10 conservative amino acid additions, deletions, or substitutions.

20. A monoclonal secretory IgA antibody, which binds to and neutralizes a human proinflammatory cytokine, wherein said antibody comprises:
(a) a light chain constant region having the sequence of SEQ ID NO:14,
a heavy chain variable region having the sequence of SEQ ID NO:4, and a light chain variable region having the sequence of SEQ ID NO:5; or
(b) a light chain constant region having the sequence of SEQ ID NO: 14, a heavy chain variable region having the sequence of SEQ ID NO: 37, and a light chain variable region having the sequence of SEQ ID NO: 38; and
(c) a human secretory chain having the sequence of SEQ ID NO:21, or minor variations thereof, wherein the minor variations are no more than 10 conservative amino acid additions, deletions, or substitutions, and
wherein said amino acid insertions, substitutions, or deletions do not significantly alter the ability of the secretory chain to stabilize secretory IgA proteolysis.

21. A monoclonal secretory IgA antibody, which binds to and neutralizes a human proinflammatory cytokine, wherein said antibody comprises:
(a) a light chain constant region having the sequence of SEQ ID NO:14,
a heavy chain variable region having the sequence of SEQ ID NO:4, and a light chain variable region having the sequence of SEQ ID NO:5; or
(b) a light chain constant region having the sequence of SEQ ID NO: 14, a heavy chain variable region having the sequence of SEQ ID NO: 37, and a light chain variable region having the sequence of SEQ ID NO: 38; and
(c) a human J-chain having the sequence of SEQ ID NO:20, or minor variations thereof, wherein the minor variations are no more than 10 conservative amino acid additions, deletions, or substitutions, and
wherein said amino acid insertions, substitutions, or deletions do not significantly alter the ability of the J-chain to join two monomeric IgA antibodies to form a dimer and to enable attachment of the secretory chain.

22. A method for treating an inflammatory disease in a human, which comprises administering an anti-inflammatory effective amount of a monoclonal secretory IgA antibody which binds to and neutralizes a human proinflammatory cytokine, wherein said antibody comprises:
(a) a light chain constant region having the sequence of SEQ ID NO:14;
a heavy chain variable region having the sequence of SEQ ID NO:4; and
a light chain variable region having the sequence of SEQ ID NO:5; or
(b) a light chain constant region having the sequence of SEQ ID NO: 14;
a heavy chain variable region having the sequence of SEQ ID NO:37; and
a light chain variable region having the sequence of SEQ ID NO:38.

23. The method according to claim 22, wherein said administering is oral, rectal, buccal, topical, parenteral, or subcutaneous.

24. The method according to claim 23, wherein said disease is selected from the group consisting of rheumatoid arthritis, inflammatory bowel disease, Crohn's disease, ulcerative colitis, psoriasis, psoriatic arthritis, ankylosing spondylitis, juvenile idiopathic arthritis, uveitis, asthma, Alzheimer's disease, multiple sclerosis, type II diabetes, systemic sclerosis, lupus nephritis, and allergic rhinitis.

* * * * *

SEQUENCE LISTING

<160> NUMBER OF SEQ ID NOS: 42

<210> SEQ ID NO 1
<211> LENGTH: 235
<212> TYPE: PRT
<213> ORGANISM: Artificial Sequence
<220> FEATURE:
<223> OTHER INFORMATION: Amino acid sequence of the soluble TNFalpha
      receptor of etanercept (extracellular part of TNF receptor 2:
      amino acids 23-257 of UniProtKB/Swiss-Prot database entry P20333
      TNR1B_HUMAN).

<400> SEQUENCE: 1

```
Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp
225                 230                 235
```

<210> SEQ ID NO 2
<211> LENGTH: 120
<212> TYPE: PRT
<213> ORGANISM: Artificial Sequence
<220> FEATURE:
<223> OTHER INFORMATION: Amino acid sequence of the heavy chain variable
      region of infliximab (cA2).

<400> SEQUENCE: 2

```
Glu Val Lys Leu Glu Glu Ser Gly Gly Gly Leu Val Gln Pro Gly Gly
1               5                   10                  15

Ser Met Lys Leu Ser Cys Val Ala Ser Gly Phe Ile Phe Ser Asn His
            20                  25                  30

Trp Met Asn Trp Val Arg Gln Ser Pro Glu Lys Gly Leu Glu Trp Val
        35                  40                  45
```

```
Ala Glu Ile Arg Ser Lys Ser Ile Asn Ser Ala Thr His Tyr Ala Glu
         50                  55                  60

Ser Val Lys Gly Arg Phe Thr Ile Ser Arg Asp Asp Ser Lys Ser Ala
 65                  70                  75                  80

Val Tyr Leu Gln Met Thr Asp Leu Arg Thr Glu Asp Thr Gly Val Tyr
                 85                  90                  95

Tyr Cys Ser Arg Asn Tyr Tyr Gly Ser Thr Tyr Asp Tyr Trp Gly Gln
                100                 105                 110

Gly Thr Thr Leu Thr Val Ser Ser
            115                 120

<210> SEQ ID NO 3
<211> LENGTH: 107
<212> TYPE: PRT
<213> ORGANISM: Artificial Sequence
<220> FEATURE:
<223> OTHER INFORMATION: Amino acid sequence of the light chain variable
      region of infliximab (cA2).

<400> SEQUENCE: 3

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Phe Val Gly Ser Ser
                 20                  25                  30

Ile His Trp Tyr Gln Gln Arg Thr Asn Gly Ser Pro Arg Leu Leu Ile
             35                  40                  45

Lys Tyr Ala Ser Glu Ser Met Ser Gly Ile Pro Ser Arg Phe Ser Gly
 50                  55                  60

Ser Gly Ser Gly Thr Asp Phe Thr Leu Ser Ile Asn Thr Val Glu Ser
 65                  70                  75                  80

Glu Asp Ile Ala Asp Tyr Tyr Cys Gln Gln Ser His Ser Trp Pro Phe
                 85                  90                  95

Thr Phe Gly Ser Gly Thr Asn Leu Glu Val Lys
            100                 105

<210> SEQ ID NO 4
<211> LENGTH: 121
<212> TYPE: PRT
<213> ORGANISM: Artificial Sequence
<220> FEATURE:
<223> OTHER INFORMATION: Amino acid sequence of the heavy chain variable
      region of adalimumab (D2E7).

<400> SEQUENCE: 4

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                 20                  25                  30

Ala Met His Trp Val Arg Gln Ala Pro Gly Lys Gly Leu Glu Trp Val
             35                  40                  45

Ser Ala Ile Thr Trp Asn Ser Gly His Ile Asp Tyr Ala Asp Ser Val
 50                  55                  60

Glu Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Lys Val Ser Tyr Leu Ser Thr Ala Ser Ser Leu Asp Tyr Trp Gly
            100                 105                 110
```

```
Gln Gly Thr Leu Val Thr Val Ser Ser
        115                 120

<210> SEQ ID NO 5
<211> LENGTH: 107
<212> TYPE: PRT
<213> ORGANISM: Artificial Sequence
<220> FEATURE:
<223> OTHER INFORMATION: Amino acid sequence of the light chain variable
      region of adalimumab (D2E7).

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105

<210> SEQ ID NO 6
<211> LENGTH: 126
<212> TYPE: PRT
<213> ORGANISM: Artificial Sequence
<220> FEATURE:
<223> OTHER INFORMATION: Amino acid sequence of the heavy chain variable
      region of golimumab.

<400> SEQUENCE: 6

Gln Val Gln Leu Val Glu Ser Gly Gly Val Val Gln Pro Gly Arg
1               5                   10                  15

Ser Leu Arg Leu Ser Cys Ala Ala Ser Gly Phe Ile Phe Ser Ser Tyr
            20                  25                  30

Ala Met His Trp Val Arg Gln Ala Pro Gly Asn Gly Leu Glu Trp Val
        35                  40                  45

Ala Phe Met Ser Tyr Asp Gly Ser Asn Lys Lys Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Ile Ala Ala Gly Gly Asn Tyr Tyr Tyr Tyr Gly
            100                 105                 110

Met Asp Val Trp Gly Gln Gly Thr Thr Val Thr Val Ser Ser
        115                 120                 125

<210> SEQ ID NO 7
<211> LENGTH: 108
<212> TYPE: PRT
<213> ORGANISM: Artificial Sequence
<220> FEATURE:
<223> OTHER INFORMATION: Amino acid sequence of the light chain variable
      region of golimumab.
```

-continued

<400> SEQUENCE: 7

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys
            100                 105

<210> SEQ ID NO 8
<211> LENGTH: 118
<212> TYPE: PRT
<213> ORGANISM: Artificial Sequence
<220> FEATURE:
<223> OTHER INFORMATION: Amino acid sequence of the heavy chain variable
      region of certolizumab pegol.

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Val Phe Thr Asp Tyr
            20                  25                  30

Gly Met Asn Trp Val Arg Gln Ala Pro Gly Lys Gly Leu Glu Trp Met
        35                  40                  45

Gly Trp Ile Asn Thr Tyr Ile Gly Glu Pro Ile Tyr Ala Asp Ser Val
    50                  55                  60

Lys Gly Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Tyr Arg Ser Tyr Ala Met Asp Tyr Trp Gly Gln Gly Thr
            100                 105                 110

Leu Val Thr Val Ser Ser
        115

<210> SEQ ID NO 9
<211> LENGTH: 107
<212> TYPE: PRT
<213> ORGANISM: Artificial Sequence
<220> FEATURE:
<223> OTHER INFORMATION: Amino acid sequence of the light chain variable
      region of certolizumab pegol.

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Ala Leu Ile
        35                  40                  45

```
Tyr Ser Ala Ser Phe Leu Tyr Ser Gly Val Pro Tyr Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ile Tyr Pro Leu
                85                  90                  95

Thr Phe Gly Gln Gly Thr Lys Val Glu Ile Lys
                100                 105

<210> SEQ ID NO 10
<211> LENGTH: 353
<212> TYPE: PRT
<213> ORGANISM: Homo sapiens

<400> SEQUENCE: 10

Ala Ser Pro Thr Ser Pro Lys Val Phe Pro Leu Ser Leu Cys Ser Thr
1               5                   10                  15

Gln Pro Asp Gly Asn Val Val Ile Ala Cys Leu Val Gln Gly Phe Phe
                20                  25                  30

Pro Gln Glu Pro Leu Ser Val Thr Trp Ser Glu Ser Gly Gln Gly Val
            35                  40                  45

Thr Ala Arg Asn Phe Pro Pro Ser Gln Asp Ala Ser Gly Asp Leu Tyr
50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Ser Thr Pro Pro Thr Pro Ser Pro
                100                 105                 110

Ser Thr Pro Pro Thr Pro Ser Pro Ser Cys Cys His Pro Arg Leu Ser
            115                 120                 125

Leu His Arg Pro Ala Leu Glu Asp Leu Leu Leu Gly Ser Glu Ala Asn
130                 135                 140

Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Gln Gly Pro Pro Glu
                165                 170                 175

Arg Asp Leu Cys Gly Cys Tyr Ser Val Ser Ser Val Leu Pro Gly Cys
            180                 185                 190

Ala Glu Pro Trp Asn His Gly Lys Thr Phe Thr Cys Thr Ala Ala Tyr
        195                 200                 205

Pro Glu Ser Lys Thr Pro Leu Thr Ala Thr Leu Ser Lys Ser Gly Asn
210                 215                 220

Thr Phe Arg Pro Glu Val His Leu Leu Pro Pro Pro Ser Glu Glu Leu
225                 230                 235                 240

Ala Leu Asn Glu Leu Val Thr Leu Thr Cys Leu Ala Arg Gly Phe Ser
                245                 250                 255

Pro Lys Asp Val Leu Val Arg Trp Leu Gln Gly Ser Gln Glu Leu Pro
            260                 265                 270

Arg Glu Lys Tyr Leu Thr Trp Ala Ser Arg Gln Glu Pro Ser Gln Gly
        275                 280                 285

Thr Thr Thr Phe Ala Val Thr Ser Ile Leu Arg Val Ala Ala Glu Asp
    290                 295                 300

Trp Lys Lys Gly Asp Thr Phe Ser Cys Met Val Gly His Glu Ala Leu
305                 310                 315                 320
```

```
Pro Leu Ala Phe Thr Gln Lys Thr Ile Asp Arg Leu Ala Gly Lys Pro
                325                 330                 335

Thr His Val Asn Val Ser Val Val Met Ala Glu Val Asp Gly Thr Cys
            340                 345                 350

Tyr

<210> SEQ ID NO 11
<211> LENGTH: 340
<212> TYPE: PRT
<213> ORGANISM: Homo sapiens

<400> SEQUENCE: 11

Ala Ser Pro Thr Ser Pro Lys Val Phe Pro Leu Ser Leu Asp Ser Thr
1               5                   10                  15

Pro Gln Asp Gly Asn Val Val Ala Cys Leu Val Gln Gly Phe Phe
            20                  25                  30

Pro Gln Glu Pro Leu Ser Val Thr Trp Ser Glu Ser Gly Gln Asn Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Pro Asp Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Pro Pro Pro Cys Cys His Pro
            100                 105                 110

Arg Leu Ser Leu His Arg Pro Ala Leu Glu Asp Leu Leu Leu Gly Ser
        115                 120                 125

Glu Ala Asn Leu Thr Cys Thr Leu Thr Gly Leu Arg Asp Ala Ser Gly
    130                 135                 140

Ala Thr Phe Thr Trp Thr Pro Ser Ser Gly Lys Ser Ala Val Gln Gly
145                 150                 155                 160

Pro Pro Glu Arg Asp Leu Cys Gly Cys Tyr Ser Val Ser Ser Val Leu
                165                 170                 175

Pro Gly Cys Ala Gln Pro Trp Asn His Gly Glu Thr Phe Thr Cys Thr
            180                 185                 190

Ala Ala His Pro Glu Leu Lys Thr Pro Leu Thr Ala Asn Ile Thr Lys
        195                 200                 205

Ser Gly Asn Thr Phe Arg Pro Glu Val His Leu Leu Pro Pro Pro Ser
    210                 215                 220

Glu Glu Leu Ala Leu Asn Glu Leu Val Thr Leu Thr Cys Leu Ala Arg
225                 230                 235                 240

Gly Phe Ser Pro Lys Asp Val Leu Val Arg Trp Leu Gln Gly Ser Gln
                245                 250                 255

Glu Leu Pro Arg Glu Lys Tyr Leu Thr Trp Ala Ser Arg Gln Glu Pro
            260                 265                 270

Ser Gln Gly Thr Thr Thr Phe Ala Val Thr Ser Ile Leu Arg Val Ala
        275                 280                 285

Ala Glu Asp Trp Lys Lys Gly Asp Thr Phe Ser Cys Met Val Gly His
    290                 295                 300

Glu Ala Leu Pro Leu Ala Phe Thr Gln Lys Thr Ile Asp Arg Leu Ala
305                 310                 315                 320

Gly Lys Pro Thr His Val Asn Val Ser Val Val Met Ala Glu Val Asp
                325                 330                 335
```

```
Gly Thr Cys Tyr
            340

<210> SEQ ID NO 12
<211> LENGTH: 340
<212> TYPE: PRT
<213> ORGANISM: Homo sapiens

<400> SEQUENCE: 12

Ala Ser Pro Thr Ser Pro Lys Val Phe Pro Leu Ser Leu Asp Ser Thr
1               5                   10                  15

Pro Gln Asp Gly Asn Val Val Ala Cys Leu Val Gln Gly Phe Phe
            20                  25                  30

Pro Gln Glu Pro Leu Ser Val Thr Trp Ser Glu Ser Gly Gln Asn Val
        35                  40                  45

Thr Ala Arg Asn Phe Pro Ser Gln Asp Ala Ser Gly Asp Leu Tyr
    50                  55                  60

Thr Thr Ser Ser Gln Leu Thr Leu Pro Ala Thr Gln Cys Pro Asp Gly
65                  70                  75                  80

Lys Ser Val Thr Cys His Val Lys His Tyr Thr Asn Ser Ser Gln Asp
                85                  90                  95

Val Thr Val Pro Cys Arg Val Pro Pro Pro Pro Cys Cys His Pro
            100                 105                 110

Arg Leu Ser Leu His Arg Pro Ala Leu Glu Asp Leu Leu Leu Gly Ser
            115                 120                 125

Glu Ala Asn Leu Thr Cys Thr Leu Thr Gly Leu Arg Asp Ala Ser Gly
130                 135                 140

Ala Thr Phe Thr Trp Thr Pro Ser Ser Gly Lys Ser Ala Val Gln Gly
145                 150                 155                 160

Pro Pro Glu Arg Asp Leu Cys Gly Cys Tyr Ser Val Ser Ser Val Leu
                165                 170                 175

Pro Gly Cys Ala Gln Pro Trp Asn His Gly Thr Phe Thr Cys Thr
            180                 185                 190

Ala Ala His Pro Glu Leu Lys Thr Pro Leu Thr Ala Asn Ile Thr Lys
            195                 200                 205

Ser Gly Asn Thr Phe Arg Pro Glu Val His Leu Leu Pro Pro Pro Ser
    210                 215                 220

Glu Glu Leu Ala Leu Asn Glu Leu Val Thr Leu Thr Cys Leu Ala Arg
225                 230                 235                 240

Gly Phe Ser Pro Lys Asp Val Leu Val Arg Trp Leu Gln Gly Ser Gln
                245                 250                 255

Glu Leu Pro Arg Glu Lys Tyr Leu Thr Trp Ala Ser Arg Gln Glu Pro
            260                 265                 270

Ser Gln Gly Thr Thr Thr Tyr Ala Val Thr Ser Ile Leu Arg Val Ala
        275                 280                 285

Ala Glu Asp Trp Lys Lys Gly Asp Thr Phe Ser Cys Met Val Gly His
    290                 295                 300

Glu Ala Leu Pro Leu Ala Phe Thr Gln Lys Thr Ile Asp Arg Met Ala
305                 310                 315                 320

Gly Lys Pro Thr His Ile Asn Val Ser Val Val Met Ala Glu Ala Asp
                325                 330                 335

Gly Thr Cys Tyr
            340
```

<210> SEQ ID NO 13
<211> LENGTH: 340
<212> TYPE: PRT
<213> ORGANISM: Homo sapiens

<400> SEQUENCE: 13

Ala Ser Pro Thr Ser Pro Lys Val Phe Pro Leu Ser Leu Asp Ser Thr
1               5                   10                  15

Pro Gln Asp Gly Asn Val Val Ala Cys Leu Val Gln Gly Phe Phe
            20                  25                  30

Pro Gln Glu Pro Leu Ser Val Thr Trp Ser Glu Ser Gly Gln Asn Val
            35                  40                  45

Thr Ala Arg Asn Phe Pro Pro Ser Gln Asp Ala Ser Gly Asp Leu Tyr
50                  55                  60

Thr Thr Ser Ser Gln Leu Thr Leu Pro Ala Thr Gln Cys Pro Asp Gly
65                  70                  75                  80

Lys Ser Val Thr Cys His Val Lys His Tyr Thr Asn Ser Ser Gln Asp
                85                  90                  95

Val Thr Val Pro Cys Arg Val Pro Pro Pro Pro Cys Cys His Pro
            100                 105                 110

Arg Leu Ser Leu His Arg Pro Ala Leu Glu Asp Leu Leu Leu Gly Ser
            115                 120                 125

Glu Ala Asn Leu Thr Cys Thr Leu Thr Gly Leu Arg Asp Ala Ser Gly
130                 135                 140

Ala Thr Phe Thr Trp Thr Pro Ser Ser Gly Lys Ser Ala Val Gln Gly
145                 150                 155                 160

Pro Pro Glu Arg Asp Leu Cys Gly Cys Tyr Ser Val Ser Ser Val Leu
            165                 170                 175

Pro Gly Cys Ala Gln Pro Trp Asn His Gly Glu Thr Phe Thr Cys Thr
            180                 185                 190

Ala Ala His Pro Glu Leu Lys Thr Pro Leu Thr Ala Asn Ile Thr Lys
            195                 200                 205

Ser Gly Asn Thr Phe Arg Pro Glu Val His Leu Leu Pro Pro Pro Ser
210                 215                 220

Glu Glu Leu Ala Leu Asn Glu Leu Val Thr Leu Thr Cys Leu Ala Arg
225                 230                 235                 240

Gly Phe Ser Pro Lys Asp Val Leu Val Arg Trp Leu Gln Gly Ser Gln
            245                 250                 255

Glu Leu Pro Arg Glu Lys Tyr Leu Thr Trp Ala Ser Arg Gln Glu Pro
            260                 265                 270

Ser Gln Gly Thr Thr Thr Phe Ala Val Thr Ser Ile Leu Arg Val Ala
            275                 280                 285

Ala Glu Asp Trp Lys Lys Gly Asp Thr Phe Ser Cys Met Val Gly His
290                 295                 300

Glu Ala Leu Pro Leu Ala Phe Thr Gln Lys Thr Ile Asp Arg Leu Ala
305                 310                 315                 320

Gly Lys Pro Thr His Val Asn Val Ser Val Val Met Ala Glu Val Asp
                325                 330                 335

Gly Thr Cys Tyr
            340

<210> SEQ ID NO 14
<211> LENGTH: 107
<212> TYPE: PRT
<213> ORGANISM: Homo sapiens

<400> SEQUENCE: 14

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 15
<211> LENGTH: 106
<212> TYPE: PRT
<213> ORGANISM: Homo sapiens

<400> SEQUENCE: 15

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 16
<211> LENGTH: 106
<212> TYPE: PRT
<213> ORGANISM: Homo sapiens

<400> SEQUENCE: 16

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

```
                    100                 105

<210> SEQ ID NO 17
<211> LENGTH: 106
<212> TYPE: PRT
<213> ORGANISM: Homo sapiens

<400> SEQUENCE: 17

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
                20                  25                  30

Phe Tyr Pro Gly Ala Val Thr Val Ala Trp Lys Ala Asp Ser Ser Pro
            35                  40                  45

Ala Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Lys Ser Tyr Ser Cys Gln Val Thr His Glu Gly Ser Thr Val
                85                  90                  95

Glu Lys Thr Val Ala Pro Thr Glu Cys Ser
                100                 105

<210> SEQ ID NO 18
<211> LENGTH: 106
<212> TYPE: PRT
<213> ORGANISM: Homo sapiens

<400> SEQUENCE: 18

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
                20                  25                  30

Phe Tyr Pro Gly Ala Val Lys Val Ala Trp Lys Ala Asp Gly Ser Pro
            35                  40                  45

Val Asn Thr Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Ala Glu Cys Ser
                100                 105

<210> SEQ ID NO 19
<211> LENGTH: 106
<212> TYPE: PRT
<213> ORGANISM: Homo sapiens

<400> SEQUENCE: 19

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Val Ser Asp
                20                  25                  30

Phe Tyr Pro Gly Ala Val Thr Val Ala Trp Lys Ala Asp Gly Ser Pro
            35                  40                  45

Val Lys Val Gly Val Glu Thr Thr Lys Pro Ser Lys Gln Ser Asn Asn
    50                  55                  60
```

```
Lys Tyr Ala Ala Ser Ser Tyr Leu Ser Leu Thr Pro Glu Gln Trp Lys
 65                  70                  75                  80

Ser His Arg Ser Tyr Ser Cys Arg Val Thr His Glu Gly Ser Thr Val
                 85                  90                  95

Glu Lys Thr Val Ala Pro Ala Glu Cys Ser
            100                 105

<210> SEQ ID NO 20
<211> LENGTH: 137
<212> TYPE: PRT
<213> ORGANISM: Homo sapiens

<400> SEQUENCE: 20

Gln Glu Asp Glu Arg Ile Val Leu Val Asp Asn Lys Cys Lys Cys Ala
  1               5                  10                  15

Arg Ile Thr Ser Arg Ile Ile Arg Ser Ser Glu Asp Pro Asn Glu Asp
                 20                  25                  30

Ile Val Glu Arg Asn Ile Arg Ile Ile Val Pro Leu Asn Asn Arg Glu
             35                  40                  45

Asn Ile Ser Asp Pro Thr Ser Pro Leu Arg Thr Arg Phe Val Tyr His
 50                  55                  60

Leu Ser Asp Leu Cys Lys Lys Cys Asp Pro Thr Glu Val Glu Leu Asp
 65                  70                  75                  80

Asn Gln Ile Val Thr Ala Thr Gln Ser Asn Ile Cys Asp Glu Asp Ser
                 85                  90                  95

Ala Thr Glu Thr Cys Tyr Thr Tyr Asp Arg Asn Lys Cys Tyr Thr Ala
            100                 105                 110

Val Val Pro Leu Val Tyr Gly Gly Glu Thr Lys Met Val Glu Thr Ala
            115                 120                 125

Leu Thr Pro Asp Ala Cys Tyr Pro Asp
            130                 135

<210> SEQ ID NO 21
<211> LENGTH: 585
<212> TYPE: PRT
<213> ORGANISM: Homo sapiens

<400> SEQUENCE: 21

Lys Ser Pro Ile Phe Gly Pro Glu Val Asn Ser Val Glu Gly Asn
  1               5                  10                  15

Ser Val Ser Ile Thr Cys Tyr Tyr Pro Pro Thr Ser Val Asn Arg His
                 20                  25                  30

Thr Arg Lys Tyr Trp Cys Arg Gln Gly Ala Arg Gly Gly Cys Ile Thr
             35                  40                  45

Leu Ile Ser Ser Glu Gly Tyr Val Ser Lys Tyr Ala Gly Arg Ala
 50                  55                  60

Asn Leu Thr Asn Phe Pro Glu Asn Gly Thr Phe Val Val Asn Ile Ala
 65                  70                  75                  80

Gln Leu Ser Gln Asp Asp Ser Gly Arg Tyr Lys Cys Gly Leu Gly Ile
                 85                  90                  95

Asn Ser Arg Gly Leu Ser Phe Asp Val Ser Leu Glu Val Ser Gln Gly
            100                 105                 110

Pro Gly Leu Leu Asn Asp Thr Lys Val Tyr Thr Val Asp Leu Gly Arg
            115                 120                 125

Thr Val Thr Ile Asn Cys Pro Phe Lys Thr Glu Asn Ala Gln Lys Arg
            130                 135                 140
```

```
Lys Ser Leu Tyr Lys Gln Ile Gly Leu Tyr Pro Val Leu Val Ile Asp
145                 150                 155                 160

Ser Ser Gly Tyr Val Asn Pro Asn Tyr Thr Gly Arg Ile Arg Leu Asp
            165                 170                 175

Ile Gln Gly Thr Gly Gln Leu Leu Phe Ser Val Val Ile Asn Gln Leu
        180                 185                 190

Arg Leu Ser Asp Ala Gly Gln Tyr Leu Cys Gln Ala Gly Asp Asp Ser
            195                 200                 205

Asn Ser Asn Lys Lys Asn Ala Asp Leu Gln Val Leu Lys Pro Glu Pro
        210                 215                 220

Glu Leu Val Tyr Glu Asp Leu Arg Gly Ser Val Thr Phe His Cys Ala
225                 230                 235                 240

Leu Gly Pro Glu Val Ala Asn Val Ala Lys Phe Leu Cys Arg Gln Ser
            245                 250                 255

Ser Gly Glu Asn Cys Asp Val Val Asn Thr Leu Gly Lys Arg Ala
            260                 265                 270

Pro Ala Phe Glu Gly Arg Ile Leu Leu Asn Pro Gln Asp Lys Asp Gly
        275                 280                 285

Ser Phe Ser Val Val Ile Thr Gly Leu Arg Lys Glu Asp Ala Gly Arg
290                 295                 300

Tyr Leu Cys Gly Ala His Ser Asp Gly Gln Leu Gln Glu Gly Ser Pro
305                 310                 315                 320

Ile Gln Ala Trp Gln Leu Phe Val Asn Glu Glu Ser Thr Ile Pro Arg
            325                 330                 335

Ser Pro Thr Val Val Lys Gly Val Ala Gly Gly Ser Val Ala Val Leu
        340                 345                 350

Cys Pro Tyr Asn Arg Lys Glu Ser Lys Ser Ile Lys Tyr Trp Cys Leu
            355                 360                 365

Trp Glu Gly Ala Gln Asn Gly Arg Cys Pro Leu Leu Val Asp Ser Glu
    370                 375                 380

Gly Trp Val Lys Ala Gln Tyr Glu Gly Arg Leu Ser Leu Leu Glu Glu
385                 390                 395                 400

Pro Gly Asn Gly Thr Phe Thr Val Ile Leu Asn Gln Leu Thr Ser Arg
            405                 410                 415

Asp Ala Gly Phe Tyr Trp Cys Leu Thr Asn Gly Asp Thr Leu Trp Arg
            420                 425                 430

Thr Thr Val Glu Ile Lys Ile Ile Glu Gly Glu Pro Asn Leu Lys Val
        435                 440                 445

Pro Gly Asn Val Thr Ala Val Leu Gly Glu Thr Leu Lys Val Pro Cys
    450                 455                 460

His Phe Pro Cys Lys Phe Ser Ser Tyr Glu Lys Tyr Trp Cys Lys Trp
465                 470                 475                 480

Asn Asn Thr Gly Cys Gln Ala Leu Pro Ser Gln Asp Glu Gly Pro Ser
            485                 490                 495

Lys Ala Phe Val Asn Cys Asp Glu Asn Ser Arg Leu Val Ser Leu Thr
            500                 505                 510

Leu Asn Leu Val Thr Arg Ala Asp Glu Gly Trp Tyr Trp Cys Gly Val
        515                 520                 525

Lys Gln Gly His Phe Tyr Gly Glu Thr Ala Ala Val Tyr Val Ala Val
    530                 535                 540

Glu Glu Arg Lys Ala Ala Gly Ser Arg Asp Val Ser Leu Ala Lys Ala
545                 550                 555                 560
```

Asp Ala Ala Pro Asp Glu Lys Val Leu Asp Ser Gly Phe Arg Glu Ile
            565                 570                 575

Glu Asn Lys Ala Ile Gln Asp Pro Arg
            580                 585

<210> SEQ ID NO 22
<211> LENGTH: 22
<212> TYPE: PRT
<213> ORGANISM: Homo sapiens

<400> SEQUENCE: 22

Met Lys Asn His Leu Leu Phe Trp Gly Val Leu Ala Val Phe Ile Lys
1               5                   10                  15

Ala Val His Val Lys Ala
            20

<210> SEQ ID NO 23
<211> LENGTH: 19
<212> TYPE: PRT
<213> ORGANISM: Artificial Sequence
<220> FEATURE:
<223> OTHER INFORMATION: Amino acid sequence for a signal peptide (heavy
      chain secretion signal).

<400> SEQUENCE: 23

Met Glu Leu Gly Leu Cys Trp Val Phe Leu Val Ala Ile Leu Glu Gly
1               5                   10                  15

Val Gln Cys

<210> SEQ ID NO 24
<211> LENGTH: 22
<212> TYPE: PRT
<213> ORGANISM: Artificial Sequence
<220> FEATURE:
<223> OTHER INFORMATION: Amino acid sequence for a signal peptide (light
      chain secretion signal).

<400> SEQUENCE: 24

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 25
<211> LENGTH: 20
<212> TYPE: PRT
<213> ORGANISM: Artificial Sequence
<220> FEATURE:
<223> OTHER INFORMATION: Amino acid sequence for a signal peptide (SC
      chain secretion signal).

<400> SEQUENCE: 25

Met Ala Met Leu Leu Phe Val Leu Thr Cys Leu Leu Ala Val Phe Pro
1               5                   10                  15

Ala Ile Ser Thr
            20

<210> SEQ ID NO 26
<211> LENGTH: 31
<212> TYPE: PRT
<213> ORGANISM: Artificial Sequence
<220> FEATURE:
<223> OTHER INFORMATION: Amino acid sequence for rice alpha-amylase
      signal peptide (secretion signal).

<400> SEQUENCE: 26

Met Gln Val Leu Asn Thr Met Val Asn Lys His Phe Leu Ser Leu Ser
1               5                   10                  15
Val Leu Ile Val Leu Leu Gly Leu Ser Ser Asn Leu Thr Ala Gly
            20                  25                  30

<210> SEQ ID NO 27
<211> LENGTH: 1440
<212> TYPE: DNA
<213> ORGANISM: Artificial Sequence
<220> FEATURE:
<223> OTHER INFORMATION: DNA sequence for infliximab heavy chain
      IgA2m(n) optimized for maize.

<400> SEQUENCE: 27

```
atggagctgg gcctgtgctg gtgttcctg gtggccatcc tcgagggcgt ccagtgcgag    60
gtgaagctcg aggagtccgg cggcggcctg gtccagcctg gcggctccat gaagctgtcc   120
tgcgtggcct ccggcttcat cttctccaac cactggatga actgggtgcg ccagtccccc   180
gagaagggcc tcgagtgggt ggccgagatc cgctccaagt ccatcaactc cgccacccac   240
tacgccgagt ccgtcaaggg caggttcacc atctcccgcg acgactccaa gtccgccgtg   300
tacctccaga tgaccgacct cgcaccgag gacaccggcg tgtactactg ctcccgcaac   360
tactacggct ccacctacga ctactggggc cagggcacca ccctgaccgt gtcctccgct   420
agccccacct ccccaaggt gttccccctg tccctggact cacccccca ggacggcaac    480
gtggtggtgg cctgcctggt ccagggcttc ttcccccagg agccctgtc cgtcacctgg   540
agcgagtccg gccagaacgt gaccgcccgc aacttccccc cctcccagga cgcttccggc   600
gacctgtaca ccacctcctc ccagctgacc ctgcccgcta cccagtgccc cgacggcaag   660
tccgtgacct gccacgtgaa gcactacacc aactccagcc aggacgtgac cgtgccctgc   720
cgcgtgcctc ctcccctcc ctgctgccac cccaggctgt ccctgcacag gcccgctctc   780
gaggacctgc tgctgggctc cgaggccaac ctgacctgca ccctgaccgg cctgagggac   840
gcctccggcg ctaccttcac ctggacccc tcctccggca agtccgctgt ccaaggccca   900
cctgagcgtg atctctgcgg ctgctactcc gtgtccagcg tgctgcccgg ctgcgcccag   960
ccctggaacc acggcgagac cttcacctgc accgccgctc accccgagct taagaccccc  1020
ctgaccgcca acatcaccaa gtccggcaac accttccgcc ccgaggtgca cctgctgccc  1080
cctcccctccg aggagctggc cctgaacgag ctggtgaccc tgacctgcct cgccaggggc  1140
ttctcccga aggacgtgct tgtgcgctgg ctccagggct cccaggagct gccccgcgag  1200
aagtacctga cctgggcctc caggcaggag ccttcccagg caccaccac cttcgccgtg  1260
acctccatcc tgagggtggc cgccgaggac tggaagaagg cgacaccttt cagctgcatg  1320
gtgggtcacg aggctctgcc cctggccttc acccaaaaga ccatcgaccg cctggctggc  1380
aagcccaccc acgtgaacgt gtccgtggtg atggccgagg tggacggcac ctgctactga  1440
```

<210> SEQ ID NO 28
<211> LENGTH: 6910
<212> TYPE: DNA
<213> ORGANISM: Artificial Sequence
<220> FEATURE:
<223> OTHER INFORMATION: DNA sequence for infliximab heavy chain IgA1
      and light chain kappa optimized for HEK.

<400> SEQUENCE: 28

```
gcttcgcgat gtacgggcca gatatacgcg ttgacattga ttattgacta gttattaata    60
```

```
gtaatcaatt acggggtcat tagttcatag cccatatatg gagttccgcg ttacataact        120
tacggtaaat ggcccgcctg gctgaccgcc caacgacccc cgcccattga cgtcaataat        180
gacgtatgtt cccatagtaa cgccaatagg gactttccat tgacgtcaat gggtggagta        240
tttacggtaa actgcccact tggcagtaca tcaagtgtat catatgccaa gtacgccccc        300
tattgacgtc aatgacggta aatggcccgc ctggcattat gcccagtaca tgaccttatg        360
ggactttcct acttggcagt acatctacgt attagtcatc gctattacca tggtgatgcg        420
gttttggcag tacatcaatg ggcgtggata gcggtttgac tcacggggat ttccaagtct        480
ccaccccatt gacgtcaatg ggagtttgtt ttggcaccaa aatcaacggg actttccaaa        540
atgtcgtaac aactccgccc cattgacgca aatgggcggt aggcgtgtac ggtgggaggt        600
ctatataagc agagctctct ggctaactag agaacccact gcttactggc ttatcgaaat        660
taatacgact cactataggg agacccaagc tagcttggta ccgggccgac ctcaccatgg        720
gatggagctg tatcatcctc ttcttggtag caacagctac aggtaagggg ctcacagtag        780
caggcttgag gtctggacat atatatgggt gacaatgaca tccactttgc ctttctctcc        840
acaggtgtgc attccgaagt gaagctggag gagtctggag gcggcttggt gcaacctgga        900
ggctccatga aactctcctg tgttgcctct ggattcattt tcagtaacca ctggatgaac        960
tgggtccgcc agtctccaga aaggggcttg aatgggttgc tgaaattagt atcaaaatcc       1020
attaattctg caacacatta tgccgagtct gtgaaaggga ggttcaccat ctcaagagat       1080
gattccaaaa gtgctgtgta cctgcaaatg accgacctga aactgaagac cactggcgtt       1140
tattactgtt ccaggaatta ctacggtagt acctacgact actggggcca aggcaccact       1200
ctcacagtgt cctcaggtga gtcgtacgct agcaagcttg atgacctggg ctgagctgga       1260
ctaagctggg ctgacctggg ctgggatggg atgggctagg atgacttggg ctggactggg       1320
cgggactgag ctggactggc ctgggctgag ctgggctggg ctggactgag ctggactggc       1380
ctgggctggg ctgggcggga tgggctgagg tggctgctaa tgtgggaaag aggccgtggg       1440
ttgagtgtga ttccacctgc agagccctga gcccagctgt gttcttaggg gttctgaggg       1500
ccacgcagct ctgttgcacc atgattctgt cttctctctt gcccactgcc tgaaggaaat       1560
ttggagtggg ctgggcccag agctcccctg tatagcaggc cctgtcctgg agggcctggc       1620
agggacatgg cttagcctgt tggcctctag tcccgagacc tcataggcca caggggtcca       1680
ctgtggcttg tttgggcctg ggtgtgggct catggagtgg tgggtgttgg actgagactc       1740
tgaccaggga caggggatg gggtcacagc caagccactc caccctacc ccatgcacac        1800 agcactcaga gcccagaccc tctcctaaga gcccccacca aaatcctctc taggggcagg       1860
ggatagagca agacatgtcc cccacccaga gcagggctg cggtcaggga gctcagggga        1920
ctcagccact ccatggcaga gccctgttta atacaacttg tgtctgggat ggcctggatc       1980
agagacccta tctaaggagc atgttcagaa accatgttgc tgggatcaga cagcagggtc       2040
caactgcagg cctgtggtgc aggagctgtg tgaccatggg gctgtcacca ggcctctctg       2100
tgctgggttc ctccagtata gaggagaggc agtatagagg agagggccgc gtcctcacag       2160
tgcattctgt gttccagcat ccccgaccag ccccaaggtc ttcccgctga gcctctgcag       2220
cacccagcca gatgggaacg tggtcatcgc ctgcctggtc cagggcttct tcccccagga       2280
gccactcagt gtgacctgga gcgaaagcgg acagggcgtg accgccagaa acttcccacc       2340
cagccaggat gcctccgggg acctgtacac cacgagcagc cagctgaccc tgccggccac       2400
```

```
acagtgccta gccggcaagt ccgtgacatg ccacgtgaag cactacacga atcccagcca    2460
ggatgtgact gtgccctgcc caggtcagag ggcaggctgg ggagtggggc ggggccaccc    2520
cgtcgtgccc tgacactgcg cctgcacccg tgttccccac agggagccgc cccttcactc    2580
acaccagagt ggaccgcggg ccgagcccca ggaggtggtg gtggacaggc caggaggggc    2640
gaggcggggg catgggaag tatgtgctga ccagctcagg ccatctctcc actccagttc     2700
cctcaactcc acctacccca tctccctcaa ctccacctac cccatctccc tcatgctgcc    2760
accccgact gtcactgcac cgaccggccc tcgaggacct gctcttaggt tcagaagcga     2820
acctcacgtg cacactgacc ggcctgagag atgcctcagg tgtcaccttc acctggacgc    2880
cctcaagtgg gaagagcgct gttcaaggac cacctgagcg tgacctctgt ggctgctaca    2940
gcgtgtccag tgtcctgccg ggctgtgccg agccatggaa ccatgggaag accttcactt    3000
gcactgctgc ctaccccgag tccaagaccc cgctaaccgc caccctctca aaatccggtg    3060
ggtccagacc ctgctcgggg ccctgctcag tgctctggtt tgcaaagcat attcctggcc    3120
tgcctcctcc ctcccaatcc tgggctccag tgctcatgcc aagtacagag ggaaactgag    3180
gcaggctgag gggccaggac acagcccggg gtgcccacca gagcagaggg gctctctcat    3240
cccctgccca gccccctgac ctggctctct accctccagg aaacacattc cggcccgagg    3300
tccacctgct gccgccgccg tcggaggagc tggccctgaa cgagctggtg acgctgacgt    3360
gcctggcacg cggcttcagc cccaaggacg tgctggttcg ctggctgcag gggtcacagg    3420
agctgccccg cgagaagtac ctgacttggg catcccggca ggagcccagc cagggcacca    3480
ccaccttcgc tgtgaccagc atactgcgcg tggcagccga ggactggaag aagggggaca    3540
ccttctcctg catggtgggc cacgaggccc tgccgctggc cttcacacag aagaccatcg    3600
accgcttggc gggtaaaccc acccatgtca atgtgtctgt tgtcatggcg gaggtggacg    3660
gcacctgcta ctgagccgcc cgcctgtccc caccccctgaa taaactccat gctcccccaa    3720
gcagccccac gcttccatcc ggcgcctgtc tgtccatcct cagggtctca gcacttggga    3780
aagggccagg gcatggacag ggaagaatac cccctgccct gagcctcggg gggcccctgg    3840
caccccccatg agactttcca ccctggtgtg agtgtgagtt gtgagtgtga gagtgtgtgg    3900
tgcaggaggc ctcgctggtg tgagatccac tagttctaga ggatctcccg atcccctatg    3960
gtgcactctc agtacaatct gctctgatgc cgcatagtta agccagtatc tgctccctgc    4020
ttgtgtgttg gaggtcgctg agtagtgcgc gagcaaaatt taagctacaa caaggcaagg    4080
cttgaccgac aattaattgc atgaagaatc tgcttagggt taggcgtttt gcgctgcttc    4140
gcgatgtacg ggccagatat acgcgttgac attgattatt gactagttat taatagtaat    4200
caattacggg gtcattagtt catagcccat atatggagtt ccgcgttaca taacttacgg    4260
taaatggccc gcctggctga ccgcccaacg acccccgccc attgacgtca ataatgacgt    4320
atgttcccat agtaacgcca atagggactt tccattgacg tcaatgggtg gagtatttac    4380
ggtaaactgc ccacttggca gtacatcaag tgtatcatat gccaagtacg ccccctattg    4440
acgtcaatga cggtaaatgg cccgcctggc attatgccca gtacatgacc ttatgggact    4500
ttcctacttg gcagtacatc tacgtattag tcatcgctat taccatggtg atgcggtttt    4560
ggcagtacat caatgggcgt ggatagcggt ttgactcacg gggatttcca agtctccacc    4620
ccattgacgt caatgggagt ttgttttggc accaaaatca acgggacttt ccaaaatgtc    4680
gtaacaactc cgccccattg acgcaaatgg gcggtaggcg tgtacggtgg gaggtctata    4740
taagcagagc tctctggcta actagagaac ccactgctta ctggcttatc gaaattaata    4800
```

-continued

```
cgactcacta tagggagacc caagctagct tggtaccggg ccgacctcac catgggatgg    4860
agctgtatca tcctcttctt ggtagcaaca gctacaggta aggggctcac agtagcaggc    4920
ttgaggtctg gacatatata tgggtgacaa tgacatccac tttgcctttc tctccacagg    4980
tgtgcattcc gacatcttgc tgactcagtc tccagccatc ctgtctgtga gtccaggaga    5040
aagagtcagt ttctcctgta gggccagtca gttcgttggc tcaagcatcc actggtatca    5100
gcaaagaaca aatggttctc caaggcttct cataaagtat gcttctgagt ctatgtctgg    5160
catccctagc agatttagtg gcagtggatc agggacagat tttactctta gcatcaacac    5220
tgtggagtct gaagatattg cagattatta ctgtcaacaa agtcattcct ggccattcac    5280
gttcggcagc gggacaaatt tggaagtgaa acgtgagtag aacgtacgct agcaagcttg    5340
atatcgaatt ctaaactctg aggggtcgg atgacgtggc cattctttgc ctaaagcatt    5400
gagtttactg caaggtcaga aaagcatgca aagccctcag aatggctgca aagagctcca    5460
acaaaacaat ttagaacttt attaaggaat aggggaagc taggaagaaa ctcaaaacat    5520
caagatttta aatacgcttc ttggtctcct tgctataatt atctgggata agcatgctgt    5580
tttctgtctg tccctaacat gccctgtgat tatccgcaaa caacacaccc aagggcagaa    5640
ctttgttact taaacaccat cctgtttgct tctttcctca ggaactgtgg ctgcaccatc    5700
tgtcttcatc ttcccgccat ctgatgagca gttgaaatct ggaactgcct ctgttgtgtg    5760
cctgctgaat aacttctatc ccagagaggc caaagtacag tggaaggtgg ataacgccct    5820
ccaatcgggt aactcccagg agagtgtcac agagcaggac agcaaggaca gcacctacag    5880
cctcagcagc accctgacgc tgagcaaagc agactacgag aaacacaaag tctacgcctg    5940
cgaagtcacc catcagggcc tgagctcgcc cgtcacaaag agcttcaaca ggggagagtg    6000
ttagagggag aagtgccccc acctgctcct cagttccagc ctgaccccct cccatccttt    6060
ggcctctgac ccttttttcca caggggacct accctattg cggtcctcca gctcatcttt    6120
cacctcaccc ccctcctcct ccttggcttt aattatgcta atgttggagg agaatgaata    6180
aataaagtga atctttgcac ctgtggtttc tctctttcct catttaataa ttattatctg    6240
ttgttttacc aactactcaa tttctcttat aagggactaa atatgtagtc atcctaaggc    6300
gcataaccat ttataaaaat catccttcat tctattttac cctatcatcc tctgcaagac    6360
agtcctccct caaacccaca agccttcgt cctcacagtc ccctgggcca tggtaggaga    6420
gacttgcttc cttgttttcc cctcctcagc aagccctcat agtccttttt aagggtgaca    6480
ggtcttacag tcatatatcc tttgattcaa ttccctgaga atcaaccaaa gcaaattcct    6540
gcagcccggg ggatccacta gtaacggccg ccagtgtgct ggaattctgc agatatccat    6600
cacactggcg gccgctcgag catgcatcta gagggccta ttctatagtg tcacctaaat    6660
gctagagctc gctgatcagc ctcgactgtg ccttctagtt gccagccatc tgttgtttgc    6720
ccctcccccg tgccttcctt gaccctggaa ggtgccactc ccactgtcct ttcctaataa    6780
aatgaggaaa ttgcatcgca ttgtctgagt aggtgtcatt ctattctggg gggtggggtg    6840
gggcaggaca gcaagggga ggattgggaa gacaatagca ggcatgctgg ggatgcggtg    6900
ggctctatgg                                                          6910
```

<210> SEQ ID NO 29
<211> LENGTH: 711
<212> TYPE: DNA
<213> ORGANISM: Artificial Sequence
<220> FEATURE:

<223> OTHER INFORMATION: DNA sequence for infliximab light chain optimized for maize.

<400> SEQUENCE: 29

```
atgaagtacc tgctgcccac cgctgctgct ggcctgctgc tgctcgctgc ccagcccgct      60
atggccgaca tcctgctgac ccagtccccc gccatcctgt ccgtgtcccc aggcgagcgc     120
gtgtccttct cctgccgcgc ctcccagttc gtgggctcct ccatccactg gtatcagcag     180
cgcaccaacg gctcccccag gctgctgatc aagtacgcct ccgagtccat gtccggcatc     240
ccgtccaggt tctccggctc cggcagcggc accgacttca ccctgtccat caacaccgtg     300
gagtccgagg acatcgccga ctactactgc cagcagtccc actcctggcc cttcaccttc     360
ggctccggca ccaacctcga ggtgaagcgt acggtggctg cccccctccgt gttcatcttc     420
cccccctccg acgagcagct gaagtccggc accgcctccg ttgtctgcct ccttaacaac     480
ttctacccc gcgaggccaa ggtccagtgg aaggtggaca cgccctcca gtccggcaac     540
tcccaggagt ccgtcaccga gcaggactcc aaggacagca cctactccct gtcctccacc     600
ctgaccctgt ccaaggccga ctacgagaag cacaaggtgt acgcctgcga ggtgacccac     660
cagggcctgt cctcccccgt caccaagtcc ttcaaccgcg gcgagtgctg a              711
```

<210> SEQ ID NO 30
<211> LENGTH: 3092
<212> TYPE: DNA
<213> ORGANISM: Artificial Sequence
<220> FEATURE:
<223> OTHER INFORMATION: DNA sequence for SC- and J-chains optimized for HEK.

<400> SEQUENCE: 30

```
gcttcgcgat gtacgggcca gatatacgcg ttgacattga ttattgacta gttattaata      60
gtaatcaatt acgggtcat tagttcatag cccatatatg gagttccgcg ttacataact     120
tacggtaaat ggcccgcctg gctgaccgcc caacgacccc cgcccattga cgtcaataat     180
gacgtatgtt cccatagtaa cgccaatagg gactttccat tgacgtcaat gggtggagta     240
tttacggtaa actgcccact tggcagtaca tcaagtgtat catatgccaa gtacgccccc     300
tattgacgtc aatgacggta aatggcccgc ctggcattat gcccagtaca tgaccttatg     360
ggactttcct acttggcagt acatctacgt attagtcatc gctattacca tggtgatgcg     420
gttttggcag tacatcaatg ggcgtggata gcggtttgac tcacggggat ttccaagtct     480
ccaccccatt gacgtcaatg ggagtttgtt ttggcaccaa aatcaacggg actttccaaa     540
atgtcgtaac aactccgccc cattgacgca aatgggcggt aggcgtgtac ggtgggaggt     600
ctatataagc agagctctct ggctaactag agaacccact gcttactggc ttatcgaaat     660
taatacgact cactataggg agacccaagc tagcttggta ccgggccgac ctcaccatga     720
agaaccacct gctgttctgg ggcgtgctgg ccgtgttcat caaggccgtg cacgtgaagg     780
ctcaggagga tgagcgcatc gtcctcgtgg acaacaagtg caagtgcgcc cgcatcacct     840
cccgcatcat ccgctcctcc gaggacccca acgaggacat cgtggagcgc aacatccgca     900
tcatcgtgcc cctgaacaac cgcgagaaca tctccgaccc cacctccccc tgaggacccc     960
gcttcgtgta ccacctgtcc gacctgtgca agaagtgcga ccccaccgag gtggagctgg    1020
acaaccagat cgtgaccgcc acccagtcca acatctgcga cgaggactcc gccaccgaga    1080
cctgctacac ctacgaccgc aacaagtgct acaccgccgt ggtgccctg gtgtacggcg    1140
gcgagaccaa gatggtggag accgcccctga ccccgacgc ttgctacccc gactgataat    1200
```

```
ctagaggatc tcccgatccc ctatggtgca ctctcagtac aatctgctct gatgccgcat    1260
agttaagcca gtatctgctc cctgcttgtg tgttggaggt cgctgagtag tgcgcgagca    1320
aaatttaagc tacaacaagg caaggcttga ccgacaatta attgcatgaa gaatctgctt    1380
agggttaggc gttttgcgct gcttcgcgat gtacgggcca gatatacgcg ttgacattga    1440
ttattgacta gttattaata gtaatcaatt acggggtcat tagttcatag cccatatatg    1500
gagttccgcg ttacataact tacggtaaat ggcccgcctg gctgaccgcc caacgacccc    1560
cgcccattga cgtcaataat gacgtatgtt cccatagtaa cgccaatagg gactttccat    1620
tgacgtcaat gggtggagta tttacggtaa actgcccact tggcagtaca tcaagtgtat    1680
catatgccaa gtacgccccc tattgacgtc aatgacggta aatggcccgc ctggcattat    1740
gcccagtaca tgaccttatg ggactttcct acttggcagt acatctacgt attagtcatc    1800
gctattacca tggtgatgcg gttttggcag tacatcaatg ggcgtggata gcggtttgac    1860 tcacgggat ttccaagtct ccaccccatt gacgtcaatg ggagtttgtt ttggcaccaa    1920
aatcaacggg actttccaaa atgtcgtaac aactccgccc cattgacgca atgggcggt    1980 aggcgtgtac ggtgggaggt ctatataagc agagctctct ggctaactag agaacccact    2040
gcttactggc ttatcgaaat taatacgact cactataggg agacccaagc tagcttggta    2100
ccgggccgac ctcaccatga agtacctgct gcccaccgct gctgctggcc tgctgctgct    2160
cgctgcccag cccgctatgg ccgacatcct gctgacccag tcccccgcca tcctgtccgt    2220
gtccccaggc gagcgcgtgt ccttctcctg ccgcgcctcc cagttcgtgg gctcctccat    2280
ccactggtat cagcagcgca ccaacggctc ccccaggctg ctgatcaagt acgcctccga    2340
gtccatgtcc ggcatcccgt ccaggttctc cggctccggc agcggcaccg acttcacccl    2400 gtccatcaac accgtggagt ccgaggacat cgccgactac tactgccagc agtcccactc    2460
ctggcccttc accttcggct ccggcaccaa cctcgaggtg aagcgtacgg tggctgcccc    2520
ctccgtgttc atcttccccc cctccgacga gcagctgaag tccggcaccg cctccgttgt    2580
ctgcctcctt aacaacttct accccgcgca ggccaaggtc cagtggaagg tggacaacgc    2640
cctccagtcc ggcaactccc aggagtccgt caccgagcag gactccaagg acagcaccta    2700
ctccctgtcc tccaccctga ccctgtccaa ggccgactac gagaagcaca aggtgtacgc    2760
ctgcgaggtg acccaccagg gcctgtcctc ccccgtcacc aagtccttca accgcggcga    2820
gtgctgataa tctagagggc ccgtttaaac ccgctgatca gcctcgactg tgccttctag    2880
ttgccagcca tctgttgttt gcccctcccc cgtgccttcc ttgaccctgg aaggtgccac    2940
tcccactgtc ctttcctaat aaaatgagga aattgcatcg cattgtctga gtaggtgtca    3000
ttctattctg gggggtgggg tggggcagga cagcaagggg gaggattggg aagacaatag    3060
caggcatgct ggggatgcgg tgggctctat gg                                 3092
```

<210> SEQ ID NO 31
<211> LENGTH: 1515
<212> TYPE: DNA
<213> ORGANISM: Artificial Sequence
<220> FEATURE:
<223> OTHER INFORMATION: DNA sequence for adalimumab heavy chain IgA1
      optimized for Lemna.

<400> SEQUENCE: 31

```
atgcaggtcc tgaacacgat ggtcaacaag cacttcctct ccctgtccgt cctcatcgtc      60
ctcctcgggc tgagcagcaa cctcaccgcc ggcgaggtcc agctggtgga gtccggcggg     120
```

```
ggcctggtcc agcccgggcg ctccctgcgc ctcagctgcg cggccagcgg cttcaccttc      180
gacgattacg ccatgcactg ggtcagacag gccccgggga agggcctcga gtgggtgtcc      240
gccatcactt ggaacagcgg ccacatcgac tacgccgact ccgtggaggg gcggttcacg      300
atcagccggg acaacgccaa gaactccctg tacctgcaga tgaactccct cagagcggag      360
gacactgcgg tctactattg cgccaaggtg agctacctga gcaccgcgtc cagcttggac      420
tactgggggc agggcaccct ggtgacggtg tcctcagcct cgcccacgtc gccgaaggtc      480
ttccccctca gcctctgctc gacgcagccc gacgggaacg ttgtcatcgc ctgcctcgtg      540
cagggcttct tcccgcagga gccgctctcc gtgacctggt ccgagagcgg ccagggcgtt      600
accgctcgga acttcccgcc ctcccaggac gcgagcggcg atctctacac tacgtcctcg      660
cagcttacgc tccggcgac gcaatgcctc gccggcaaga gcgtgacgtg ccacgtcaag      720
cactacacca atccctcgca ggacgtgacc gtgccctgcc cggtgccttc cacgcctccg      780
acgccgagcc cgtccacgcc gccgacccct cgcccagct gctgtcaccc gcgcctctcc      840
ctccaccggc ccgccctgga ggacctgttg ctcgggagcg aggcgaacct cacctgcacg      900
ctcacgggcg tgcgcgacgc ctctggcgtt accttcacct ggacgccctc ttccgggaag      960
agcgccgtgc agggcccgcc cgagagagac ctctgcggtt gctactccgt gtcgagcgtg     1020
ctccggggt gcgcggagcc gtggaaccac gggaagacct caacctgcac cgcggcctac     1080
cctgagtcca agacgcccct gaccgccacc ctgtccaagt ccgggaacac cttccgcccg     1140
gaggtgcact gctgccacc gcccagcgag gaactcgccc tgaacgagct ggtcacgctc     1200
acctgcctgg ctagggcctt ctcgcccaag gacgtgctgg tccgctggtt gcaaggcagc     1260
caggagctgc cgcgcgagaa gtacctcacc tgggcctcta ggcaggagcc ctcgcagggc     1320
accactacgt tcgcggtgac ctccatcctc agggtcgccg ctgaggactg gaagaaaggc     1380
gacaccttct cctgcatggt cggccacgag gcgctgcccc tcgccttcac ccagaagacc     1440
atcgaccggc tggccgggaa gcccacccac gtcaacgtca gcgtcgttat ggctgaggtt     1500
gacgggacgt gctac                                                      1515
```

<210> SEQ ID NO 32
<211> LENGTH: 735
<212> TYPE: DNA
<213> ORGANISM: Artificial Sequence
<220> FEATURE:
<223> OTHER INFORMATION: DNA sequence for adalimumab light chain kappa
      optimized for Lemna.

<400> SEQUENCE: 32

```
atgcaggtcc tgaacacgat ggtcaacaag cacttcctct ccctgtccgt cctcatcgtc       60
ctcctcgggc tgagcagcaa cctcaccgcc ggcgacatcc agatgacgca gagcccgtcg      120
agcctgtccg cctccgtcgg ggacagggtc acgatcacct gcagagccag ccagggcatc      180
cgcaactacc tggcctggta tcaacagaag cccgggaagg ctccgaagct cctgatctac      240
gcggccagca ccctccagag cggcgtcccg agccggttct ccgcagcgg ctccggcacc      300
gacttcaccc tcaccatcag ctcgctccag ccgaggacg tcgccaccta ctactgccag      360
aggtacaacc gcgcgccgta cacgttcggg cagggcacga aggtggagat caagcgcacg      420
gtggccgcgc ccagcgtctt catcttcccg ccctcggacg agcagctgaa gtccggcact      480
gcctccgtgt gtctgctgct caacaacttc taccccgcg aagccaaggt gcagtggaag      540
gttgacaacg cgctccagag cgggaactcc caggagtccg tgaccgagca ggactccaag      600
```

```
gactccacct acagcctgtc cagcaccctc accctctcca aggccgacta cgagaagcac    660
aaggtgtacg cctgcgaggt gacccaccag ggcctctcct ccccggtgac caagtccttc    720
aaccgcggtg agtgc                                                    735
```

<210> SEQ ID NO 33
<211> LENGTH: 480
<212> TYPE: DNA
<213> ORGANISM: Artificial Sequence
<220> FEATURE:
<223> OTHER INFORMATION: DNA sequence for J-chain optimized for maize.

<400> SEQUENCE: 33

```
atgaagaacc acctgctgtt ctggggcgtg ctggccgtgt tcatcaaggc cgtgcacgtg     60
aaggctcagg aggatgagcg catcgtcctc gtggacaaca agtgcaagtg cgcccgcatc    120
acctcccgca tcatccgctc ctccgaggac cccaacgagg acatcgtgga gcgcaacatc    180
cgcatcatcg tgcccctgaa caaccgcgag aacatctccg accccacctc ccccctgagg    240
acccgcttcg tgtaccacct gtccgacctg tgcaagaagt gcgaccccac cgaggtggag    300
ctggacaacc agatcgtgac cgccacccag tccaacatct cgacgagga ctccgccacc    360 gagacctgct acacctacga ccgcaacaag tgctacaccg ccgtggtgcc cctggtgtac    420
ggcggcgaga ccaagatggt ggagaccgcc ctgaccccg acgcttgcta ccccgactga    480
```

<210> SEQ ID NO 34
<211> LENGTH: 504
<212> TYPE: DNA
<213> ORGANISM: Artificial Sequence
<220> FEATURE:
<223> OTHER INFORMATION: DNA sequence for J-chain optimized for Lemna.

<400> SEQUENCE: 34

```
atgcaggtcc tgaacacgat ggtcaacaag cacttcctct ccctgtccgt cctcatcgtc     60
ctcctcgggc tgagcagcaa cctcaccgcc ggccaggagg acgagcgcat cgtcctcgtg    120
gacaacaagt gcaagtgcgc gcgcatcacc agccgcatca tccggtccag cgaggacccc    180
aacgaggaca tcgtcgagcg caacatccgc atcatcgtgc ccctgaacaa ccgcgagaac    240
atctccgacc cgacctcccc gctgaggacc cgcttcgtgt accacctgag cgacctctgc    300
aagaagtgcg accccaccga ggtggaactc gacaaccaga tcgtcacggc cacccagagc    360
aacatctgcg acgaggactc cgccaccgag acgtgctaca cctacgacag gaacaagtgc    420
tacacggccg tcgtgcccct cgtgtacggc ggggagacca agatggtcga cggccctg     480 accccggacg cgtgctaccc cgac                                          504
```

<210> SEQ ID NO 35
<211> LENGTH: 1818
<212> TYPE: DNA
<213> ORGANISM: Artificial Sequence
<220> FEATURE:
<223> OTHER INFORMATION: DNA sequence for SC-chain optimized for maize.

<400> SEQUENCE: 35

```
atggctatgc tgctgttcgt gctgacctgc ctgctggccg tgttccccgc catctccacc     60
aagtccccca tcttcggccc cgaggaggtg aactccgtgg agggcaactc cgtgtccatc    120
acctgctact accccccac ctccgtgaac cgccacacta ggaagtactg gtgcaggcag    180
ggcgctaggg gcggctgcat cacccctgatc tcctccgagg gctacgtttc tagcaagtac    240
```

```
gctggcaggg ccaacctgac caacttcccc gagaacggca ccttcgtggt gaacatcgcc      300
cagctgtccc aggacgactc cggccgctac aagtgcggcc tgggcatcaa ctccaggggc      360
ctgtccttcg acgtgtccct cgaggtgtcc cagggcccag gcctgctgaa cgacaccaag      420
gtgtacaccg tggacctcgg tcgcaccgtc accatcaact gccccttcaa gaccgagaac      480
gcccagaagc gcaagtccct gtacaagcag atcggcctgt accccgtgct ggtgatcgac      540
tcctccggct acgtgaaccc caactacacc ggccgcatcc gcctggacat ccagggcact      600
ggccagctgc tgttctccgt ggtgatcaac cagctgcgcc tgtccgatgc tggccaatac      660
ctgtgccaag ctggcgacga ctccaactcc aacaagaaga cgccgacct ccaggtgctg       720 aagcccgagc ccgagctggt gtacgaggac ctgcgcggct ccgtgacctt ccactgcgct      780
ctgggccccg aggtggcgaa cgttgcgaag ttcctctgca ggcagtcctc cggcgagaac      840
tgcgacgtgg tggtgaacac cctgggcaag cgcgctcccg ctttcgaggg ccgcatcctg      900
ctgaaccccc aggacaagga cggctccttc tccgtcgtca tcaccggcct gcgcaaggag      960
gacgctggcc gctacctctg cggcgctcac tccgacggca gctccagga gggctccccc     1020 atccaggcct ggcagctgtt cgtgaacgag gagtccacca tccccaggtc ccccaccgtg     1080 gtgaaggcg tggctggcgg ctccgtggct gtgctgtgcc cctacaaccg caaggagtcc     1140
aagtccatca gtactggtg cctgtgggag ggcgctcaga acggcaggtg ccccctgctc     1200
gtggactccg agggctgggt gaaggcccag tacgagggca ggctgtccct gctcgaggag     1260
cccggcaacg gcaccttcac cgtgatcctg aaccagctga cctcccgcga cgccggcttc     1320
tactggtgcc tcaccaacgg cgacaccctg tggaggacca ccgtggagat caagatcatc     1380
gagggcgagc ccaacctgaa ggtcccaggg aacgtgaccg ctgtgctggg cgagaccctg     1440
aaggtcccct gccacttccc ctgcaagttc tcctcctacg agaagtactg gtgcaagtgg     1500
aacaacaccg gctgccaggc tctgccctcc caggacgagg gcccctccaa ggccttcgtg     1560
aactgcgacg agaactcccg cctggtgtcc ctgaccctga acctggtgac cagggccgac     1620
gagggctggt actggtgcgg cgtgaagcag ggccacttct acggcgagac cgccgctgtg     1680
tacgtggccg tggaggagag gaaggccgct ggctctaggg atgtttctct tgccaaggct     1740
gacgctgccc ccgacgagaa ggtgctggac tccggcttcc gcgagatcga gaacaaggcc     1800
atccaggacc cccgctga                                                    1818

<210> SEQ ID NO 36
<211> LENGTH: 1848
<212> TYPE: DNA
<213> ORGANISM: Artificial Sequence
<220> FEATURE:
<223> OTHER INFORMATION: DNA sequence for SC-chain optimized for Lemna.

<400> SEQUENCE: 36
atgcaggtcc tgaacacgat ggtcaacaag cacttcctct ccctgtccgt cctcatcgtc       60
ctcctcgggc tgagcagcaa cctcaccgcc ggcaagtccc cgatcttcgg gccggaggaa      120
gtgaactcgg tggaggggaa ctccgtcagc atcacctgct actatcctcc gacgagcgtg      180
aaccggcaca cgaggaagta ctggtgcagg caagggccag aggcgggtg catcacccctc      240 atctccagcg aggggtacgt ctcgtccaag tacgccggtc gcgccaacct cacgaacttc      300
cccgagaacg ggacgttcgt tgtgaacatc gcccagctgt cgcaggacga cagcggccgc      360
tacaagtgtg gcctcgggat caacagccgc gggctctcct tcgacgtctc gctgagggtg      420
tcccagggcc ccggcctcct gaacgacacg aaagtgtaca ccgttgacct cggccggacg      480
```

```
gtcactatca actgcccgtt caagaccgag aacgcccaga agcgcaagag cctctacaag    540
cagatcggcc tctaccggt cctggtgatc gactcctcgg gctacgtcaa cccgaactac    600
accggccgca tccggctgga catccagggg accgggcagc tgctcttctc cgtggtcatc    660
aaccagctcc gcctgagcga cgccgggcag tacctgtgcc aggccgggga cgatagcaac    720
tccaacaaga gaacgccga cctccaagtg ctgaagcccg agccggagct ggtctacgag    780
gacctccgcg gtccgtgac cttccactgc gccctgggcc ggaggtcgc caacgtggcg    840 aagttcctgt gccggcagtc ctcgggtgag aactgcgacg tggtcgtgaa caccctcggg    900
aagcgcgcgc cgccttcga gggccgcatc ctgctcaatc cccaggacaa ggacgggtcc    960
ttcagcgtgg tcatcacggg cctccgcaag gaagacgcgg gccgctacct ctgcggcgcc    1020
cactcggacg gccagctcca ggaggggagc cccatccagg cctggcagct gttcgtcaac    1080
gaggagtcca cgatccccag aagccccacc gtggttaagg gcgtcgccgg tggctccgtg    1140
gcggtgctgt gcccgtacaa ccgcaaggag agcaagtcca tcaagtactg gtgcctgtgg    1200
gagggcgccc agaacgggag atgcccgctc ctggtggact ccgaggggtg ggtgaaggcg    1260
cagtacgagg ccgcctctc gctcctggag gagcccggca acggcacctt caccgtcatc    1320
ctcaaccagc tgacgtcgcg ggacgccggc ttctactggt gcctcaccaa cggcgacacc    1380
ctctggagga ccacggtgga gatcaagatc atcgagggcg agccgaacct gaaagtccct    1440
gggaacgtga ccgctgtcct cggcgagacc ctgaaggtgc cctgccactt cccctgcaag    1500
ttctccagct acgagaagta ctggtgcaag tggaacaaca ccggctgtca ggccctcccc    1560
tcgcaggacg aggggccgtc caaggcgttc gtgaactgcg acgagaacag ccgcctcgtg    1620
tccctcaccc tcaacctcgt gacccgcgcc gacgagggct ggtactggtg cggggtgaag    1680
cagggccact tctacgggga gaccgccgcg gtctacgtgg cggtcgagga gcgcaaggcc    1740
gctggctccc gcgacgtcag cctggccaag gccgacgccg cgcccgacga gaaggtgctg    1800
gactccgggt tccgggagat cgagaacaag gccatccagg atccccgg                1848
```

<210> SEQ ID NO 37
<211> LENGTH: 119
<212> TYPE: PRT
<213> ORGANISM: Artificial Sequence
<220> FEATURE:
<223> OTHER INFORMATION: Amino acid sequence of the heavy chain variable
      region of ustekinumab (CTNO-1275).

<400> SEQUENCE: 37

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Thr Tyr
            20                  25                  30

Trp Leu Gly Trp Val Arg Gln Met Pro Gly Lys Gly Leu Asp Trp Ile
        35                  40                  45

Gly Ile Met Ser Pro Val Asp Ser Asp Ile Arg Tyr Ser Pro Ser Phe
    50                  55                  60

Gln Gly Gln Val Thr Met Ser Val Asp Lys Ser Ile Thr Thr Ala Tyr
65                  70                  75                  80

Leu Gln Trp Asn Ser Leu Lys Ala Ser Asp Thr Ala Met Tyr Tyr Cys
                85                  90                  95

Ala Arg Arg Arg Pro Gly Gln Gly Tyr Phe Asp Phe Trp Gly Gln Gly
            100                 105                 110
```

Thr Leu Val Thr Val Ser Ser
        115

<210> SEQ ID NO 38
<211> LENGTH: 107
<212> TYPE: PRT
<213> ORGANISM: Artificial Sequence
<220> FEATURE:
<223> OTHER INFORMATION: Amino acid sequence of the light chain variable
      region of ustekinumab (CTNO-1275).

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ile Tyr Pro Tyr
                85                  90                  95

Thr Phe Gly Gln Gly Thr Lys Leu Glu Ile Lys
            100                 105

<210> SEQ ID NO 39
<211> LENGTH: 115
<212> TYPE: PRT
<213> ORGANISM: Artificial Sequence
<220> FEATURE:
<223> OTHER INFORMATION: Amino acid sequence of the heavy chain variable
      region of briakinumab (CJ-695, ABT-874).

<400> SEQUENCE: 39

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Lys Thr His Gly Ser His Asp Asn Trp Gly Gln Gly Thr Met Val Thr
            100                 105                 110

Val Ser Ser
        115

<210> SEQ ID NO 40
<211> LENGTH: 112
<212> TYPE: PRT
<213> ORGANISM: Artificial Sequence
<220> FEATURE:
<223> OTHER INFORMATION: Amino acid sequence of the light chain variable
      region of briakinumab (J-695, ABT-874).

<400> SEQUENCE: 40

```
Gln Ser Val Leu Thr Gln Pro Pro Ser Val Ser Gly Ala Pro Gly Gln
1               5                   10                  15

Arg Val Thr Ile Ser Cys Ser Gly Ser Arg Ser Asn Ile Gly Ser Asn
            20                  25                  30

Thr Val Lys Trp Tyr Gln Gln Leu Pro Gly Thr Ala Pro Lys Leu Leu
        35                  40                  45

Ile Tyr Tyr Asn Asp Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Tyr Asp Arg Tyr Thr
                85                  90                  95

His Pro Ala Leu Leu Phe Gly Thr Gly Thr Lys Val Thr Val Leu Gly
            100                 105                 110
```

<210> SEQ ID NO 41
<211> LENGTH: 1509
<212> TYPE: DNA
<213> ORGANISM: Artificial Sequence
<220> FEATURE:
<223> OTHER INFORMATION: Lemna-optimized complete SILA heavy chain IgA1
      DNA (including signal peptide SEQ ID NO:26).

<400> SEQUENCE: 41

```
atgcaggtcc tgaacacgat ggtcaacaag cacttcctct ccctgtccgt cctcatcgtc      60
ctcctcgggc tgagcagcaa cctcaccgcc ggcgaggtcc agctggtgca gtccggcgcg     120
gaggtcaaga agcctgggga atccctgaag atcagctgca agggcagcgg gtacagcttc     180
accacttact ggtcggctg gtgcgccag atgccgggca aggggctgga ctggatcggg       240
atcatgtccc ccgtggactc cgacatccgg tactccccga gcttccaggg ccaggtcact     300
atgtccgtgg acaagagcat caccacggcc tacttgcagt ggaactccct gaaggcgagc     360
gataccgcga tgtactattg cgcgagacgg agacccgggc agggctactt cgacttctgg     420
gggcagggca ccctggtgac ggtgtcctca gcctcgccca gtcgccgaa ggtcttcccc      480 ctcagcctct gctcgacgca gcccgacggg aacgttgtca tcgcctgcct cgtgcagggc     540
ttcttcccgc aggagccgct ctccgtgacc tggtccgaga gcggccaggg cgttaccgct     600
cggaacttcc cgcctccca ggacgcgagc ggcgatctct acactacgtc ctcgcagctt      660
acgctcccgg cgacgcaatg cctgccggc aagagcgtga cgtgccacgt caagcactac      720
accaatccct cgcaggacgt gaccgtgccc tgcccggtgc cttccacgcc tccgacgccg     780
agcccgtcca cgccgccgac cccttcgccc agctgctgtc accgcgcct ctccctccac      840 cggcccgccc tggaggacct gttgctcggg agcgaggcga acctcacctg cacgctcacg     900
ggcctgcgcg acgcctctgg cgttaccttc acctggacgc cctcttccgg aagagcgcc      960 gtgcagggcc cgcccgagag agacctctgc ggttgctact ccgtgtcgag cgtgctcccg    1020
gggtgcgcgg agccgtggaa ccacgggaag accttcacct gcaccgcggc ctaccctgag    1080
tccaagacgc ccctgaccgc cacccctgtcc aagtccggga acaccttccg cccggaggtg    1140
cacttgctgc caccgccag cgaggaactc gccctgaacg agctggtcac gctcacctgc     1200
ctggctaggg gcttctcgcc caaggacgtg ctggtccgct ggttgcaagg cagccaggag    1260
ctgccgcgcg agaagtacct cacctgggcc tctaggcagg agcccctcgca gggcaccact    1320 acgttcgcgg tgacctccat cctcagggtc gccgctgagg actggaagaa aggcgacacc    1380
```

```
ttctcctgca tggtcggcca cgaggcgctg cccctcgcct tcacccagaa gaccatcgac    1440
cggctggccg ggaagcccac ccacgtcaac gtcagcgtcg ttatggctga ggttgacggg    1500
acgtgctac                                                            1509
```

<210> SEQ ID NO 42
<211> LENGTH: 735
<212> TYPE: DNA
<213> ORGANISM: Artificial Sequence
<220> FEATURE:
<223> OTHER INFORMATION: Lemna-optimized complete SILA light chain DNA
      (including signal peptide SEQ ID NO:26).

<400> SEQUENCE: 42

```
atgcaggtcc tgaacacgat ggtcaacaag cacttcctct ccctgtccgt cctcatcgtc     60
ctcctcgggc tgagcagcaa cctcaccgcc ggcgacatcc agatgacgca gagcccgtcg    120
agcctgtccg cctccgtcgg ggacagggtc acgatcacct gcagagccag ccagggcatc    180
tcgtcctggc tggcctggta tcaacagaag cccgagaagg ctccgaagtc cctgatctac    240
gcggccagct ccctccagag cggcgtcccg agccggttct ccggcagcgg ctccggcacc    300
gacttcaccc tcaccatcag ctcgctccag cccgaggact tcgccaccta ctactgccag    360
cagtacaaca tctacccgta cacgttcggg cagggcacga agctggagat caagcgcacg    420
gtggccgcgc ccagcgtctt catcttcccg ccctcggacg agcagctgaa gtccggcact    480
gcctccgtgg tctgcctgct caacaacttc taccccgcg aagccaaggt gcagtggaag    540
gttgacaacg cgctccagag cgggaactcc caggagtccg tgaccgagca ggactccaag    600
gactccacct acagcctgtc cagcaccctc accctctcca aggccgacta cgagaagcac    660
aaggtgtacg cctgcgaggt gacccaccag ggcctctcct cccggtgac caagtccttc    720 aaccgcggtg agtgc                                                    735
```